(12) United States Patent
Cottarel et al.

(10) Patent No.: US 9,155,792 B2
(45) Date of Patent: *Oct. 13, 2015

(54) RECA INHIBITORS WITH ANTIBIOTIC ACTIVITY, COMPOSITIONS AND METHODS OF USE

(75) Inventors: Guillaume Cottarel, Lexington, MA (US); Jamey Wierzbowski, Stoneham, MA (US); Kollol Pal, Needham, MA (US); Michael Kohanski, Allston, MA (US); Daniel Dwyer, Watertown, MA (US); James Collins, Newton, MA (US); Michael Almstetter, Grasbrunn (DE); Michael Thormann, Martinsried (DE); Andreas Treml, Bodenmais (DE)

(73) Assignee: Trustees of Boston University, Boston, MA (US)

( * ) Notice: Subject to any disclaimer, the term of this patent is extended or adjusted under 35 U.S.C. 154(b) by 939 days.

This patent is subject to a terminal disclaimer.

(21) Appl. No.: 12/279,243

(22) PCT Filed: Feb. 13, 2007

(86) PCT No.: PCT/US2007/003712
§ 371 (c)(1),
(2), (4) Date: Feb. 27, 2009

(87) PCT Pub. No.: WO2007/097940
PCT Pub. Date: Aug. 30, 2007

(65) Prior Publication Data
US 2010/0029597 A1      Feb. 4, 2010

Related U.S. Application Data

(60) Provisional application No. 60/772,648, filed on Feb. 13, 2006, provisional application No. 60/835,596, filed on Aug. 4, 2006.

(51) Int. Cl.
| | | |
|---|---|---|
| *A61K 49/00* | (2006.01) | |
| *C07H 19/16* | (2006.01) | |
| *A61K 38/00* | (2006.01) | |
| *A61K 45/06* | (2006.01) | |
| *A61K 38/12* | (2006.01) | |
| *C12Q 1/18* | (2006.01) | |
| *G01N 33/50* | (2006.01) | |

(52) U.S. Cl.
CPC .............. *A61K 45/06* (2013.01); *A61K 38/12* (2013.01); *C12Q 1/18* (2013.01); *G01N 33/5023* (2013.01)

(58) Field of Classification Search
CPC ....... A61K 38/00; A61K 38/04; A61K 49/00; A01N 43/04; A01N 35/00; A01N 57/00; C07F 9/02
USPC ............ 424/9.1, 9.2; 514/15, 45, 81, 85, 679; 530/326; 536/27.3; 544/243, 244
See application file for complete search history.

(56) References Cited

U.S. PATENT DOCUMENTS

| | | |
|---|---|---|
| 3,669,965 A | 6/1972 | White |
| 3,689,646 A | 9/1972 | Sevag |
| 4,382,892 A | 5/1983 | Hayakawa et al. |
| 4,514,330 A | 4/1985 | Sengupta |
| 4,563,459 A | 1/1986 | Grohe et al. |
| 4,620,007 A | 10/1986 | Grohe et al. |
| 4,680,382 A | 7/1987 | Sengupta |
| 4,952,496 A | 8/1990 | Studier et al. |
| 4,966,962 A | 10/1990 | Sengupta |
| 4,985,557 A | 1/1991 | Hayakawa et al. |
| 5,053,407 A | 10/1991 | Hayakawa et al. |
| 5,115,209 A | 5/1992 | Grace et al. |
| 5,142,046 A | 8/1992 | Hayakawa et al. |
| 5,358,713 A | 10/1994 | Shimamura |
| 5,376,371 A * | 12/1994 | Bombardelli ................. 424/745 |
| 5,773,462 A | 6/1998 | Lin et al. |
| 5,972,999 A * | 10/1999 | Murad .......................... 514/474 |
| 6,268,393 B1 | 7/2001 | Xu et al. |
| 6,436,694 B1 | 8/2002 | Tally et al. |
| 6,608,087 B1 | 8/2003 | Charifson et al. |
| 6,632,809 B2 | 10/2003 | Grillot et al. |
| 2002/0068757 A1* | 6/2002 | Lin et al. ....................... 514/340 |
| 2002/0151599 A1* | 10/2002 | Buchholz et al. ............. 514/685 |
| 2003/0096762 A1* | 5/2003 | Fischer et al. .................. 514/27 |
| 2003/0118547 A1 | 6/2003 | Vandenberg |
| 2004/0043989 A1 | 3/2004 | Grillot et al. |
| 2004/0097430 A1* | 5/2004 | Zhao et al. ....................... 514/27 |
| 2004/0152760 A1* | 8/2004 | Castillo et al. ................ 514/453 |
| 2004/0215017 A1 | 10/2004 | Gordeev et al. |
| 2004/0229825 A1* | 11/2004 | Higuchi et al. .................. 514/27 |
| 2005/0054589 A1 | 3/2005 | Johnson et al. |

(Continued)

FOREIGN PATENT DOCUMENTS

| | | |
|---|---|---|
| DE | 10205863 | 8/2003 |
| JP | 03246227 | 11/1991 |

(Continued)

OTHER PUBLICATIONS

International Search Report, PCT/US2007/03698, mailed Sep. 16, 2008.
Written Opinion, PCT/US2007/03698, mailed Nov. 3, 2006.
International Search Report, PCT/US2007/003712, mailed Sep. 29, 2008.
Written Opinion, PCT/US2007/003712, mailed Sep. 29, 2008.
International Search Report, PCT/US2007/075093, mailed May 14, 2008.
Written Opinion, PCT/US2007/075093, mailed May 14, 2008.
International Search Report, PCT/US2008/069343, mailed Nov. 13, 2009.
Written Opinion, PCT/US2008/069343, mailed Nov. 13, 2009.
Aihara et al., The N-terminal domain of the human Rad51 protein binds DNA: structure and a DNA binding surface as revealed by NMR. J Mol Biol. 1999, 290(2):495-504.
Akerley et al., Proc. Natl. Acad. Sci USA 1998, 95: 8927-32.
Alekshun, New advances in antibiotic development and discovery, Expert Opin Investig Drugs. 2005, 14(2):117-34.

(Continued)

*Primary Examiner* — Rodney P Swartz
(74) *Attorney, Agent, or Firm* — Nixon Peabody LLP

(57) ABSTRACT

The present invention is directed to the use of RecA inhibitors as antibiotic agents, and provides RecA inhibitors useful in treating infections. Also provided are various compositions and methods associated with RecA inhibition.

13 Claims, 21 Drawing Sheets

(56) References Cited

U.S. PATENT DOCUMENTS

| | | | |
|---|---|---|---|
| 2005/0054697 A1 | 3/2005 | Yager et al. |
| 2006/0111302 A1 | 5/2006 | Romesberg et al. |
| 2006/0199768 A1 | 9/2006 | Singleton |
| 2009/0264342 A1 | 10/2009 | Cottarel et al. |
| 2010/0234348 A1 | 9/2010 | Cottarel et al. |
| 2011/0015137 A1 | 1/2011 | Cottarel |

FOREIGN PATENT DOCUMENTS

| | | |
|---|---|---|
| JP | 2003171274 | 6/2003 |
| WO | 98/36750 | 8/1998 |
| WO | 9835750 | 8/1998 |
| WO | WO-98/36750 | 8/1998 |
| WO | WO-99/07667 | 7/1999 |
| WO | WO-00/01714 | 1/2000 |
| WO | WO-00/032196 | 6/2000 |
| WO | WO-02/09758 | 2/2002 |
| WO | 2006096757 | 9/2006 |
| WO | WO-2006/095757 | 9/2006 |
| WO | WO-2006/108075 | 10/2006 |
| WO | WO-2007/095187 | 8/2007 |

OTHER PUBLICATIONS

Alksne et al., Antimicrob. Agents Chemother. 2000, 44: 1418-1427.
Amundsen et al., The RecD subunit of the *Escherichia coli* RecBCD enzyme inhibits RecA loading, homologous recombination, and DNA repair. Proc Natl Acad U S A. 2000, 97(13):7399-404.
Andrea et al., Biopolymers 1998, 47: 415-433.
Arigoni et al., Nat. Biotechnol. 1998, 16(9): 851-6.
Ariza et al., Conformational flexibility revealed by the crystal structure of a crenarchaeal RadA. Nucl. Acids Res. 2005 33(5): 165-73.
Baba et al., Constructon of *Escherichia coli* K-12 in-frame, single-gene knockout mutants: the Keio collection. Mol. Syst. Biol. 2006, 2:2006,0008. Epub Feb. 21, 2006.
Bayles et al., A genetic and molecular characterization of the recA gene from *Staphylococcus aureus*. Gene. 1994, 147(1):13-20.
Bernovsky et al., Anal. Biochem, 1973, 53: 452-458.
Bisognano et al., J. Biol. Chem. 2004, 279: 9064.
Brendel et al., Evolutionary comparisons of RecA-like proteins across all major kingdoms of living organisms. J Mol Evol. 1997 44(5):528-41.
Buchmeier et al., Mol. Microbiol. 1993. 7: 933-936.
Buchmeier et al., DNA repair is more important than catalase for *Salmonella* virulence in mice. J Clin Invest. 1995, 95(3):1047-53.
Cadman et al., PriB stimulates PriA helicase via an interaction with single-stranded DNA. J Biol Chem. 2005, 280(48):39693-39700.
Cano et al., Role of the RecBCD recombination pathway in *Salmonella* virulence. J Bacteriol. 2002, 184(2):592-5.
Caruthers et al., Helicase structure and mechanism. Curr Opin Struct Biol. 2002, 12(1):123-33.
Chalker et al., Rational identification of new antibacterial drug targets that are essential for viability using a genornics-based approach. Pharmacol Ther. 2002, 95: 1-20.
Chase et al., *Escherichia coli* mutants deficient in exonuclease VII. J Bacteriol. 1977, 129(2):934-47.
Chase et al., *Escherichia coli* exonuclease VII. Cloning and seguencjng of the gene encoding the large subunit (xseA). J. Biol. Chem. 1986, 261(32): 14929-35.
Choi et al., Effects of FIS protein on rrip13 transcription in *Escherichia coli*. Mol Cells 2005, 19(2):239-45.
Chu, Recent progress in Novel Macrolides, Quinolones, and 2-pyridones to overcome bacterial Resistance, Medicinal Research Reviews, 1999, 19(6):497-520.
Cirz et al., Inhibition of mutation and combating the evolution of antibiotic resistance. PLoS Biol. 2005, 3(6):e176.
Conway et al., Crystal structure of a Rad51 filament. Nat Struct Mol Biol. 2004, 11(8):791-6.
Courcelle et al., Rec.A.-dependent recovery of arrested DNA replication forks. Annu Rev Genet. 2003 37:611-646.

Cox et al., The importance of repairing stalled repication forks. Nature 2000, 404(6773):37-41.
DaSilva et al., Biological activity and synthetic methodologies for the preparation of fluoroquinclones, a class of potent antibacterial agents. Curr Med Chem 10(1):21-39.
Database Caplus, Chemical Abstracts Service, Columbus, Ohio, US; XP002468477, retrieved from STN Database accession No. 2003:460549 abstract.
Datebase Caplus, Chemical Abstacts Service, Columbus, Ohio, US; XP002468510, retrieved from STN Database accession No. 1977:463347 abstract.
Database WPI, Derwent Publications LTD., London, GB; retrieved from EPO Database accession No. 2003-819104[77] abstract.
Datsenko et al., Proc. Natl. Acad. Sci USA 2000, 97: 6640-5.
Datta et al., Crystal structures of *Mycobacterium smegmatis* RecA and its nucleotide complexes. J Bacteriol. 2003, 185(14):4280-4.
Datta et al., Crystal structures of *Mycobacterium tuberculosis* RecA and its complex with ADPAIF(4): implications for decreased ATPase activity and molecular aggregation. Nucleic Acids Res. 2000, 28(24):4964-73.
Davis, Microbiol Rev. 1987, 51: 341-350.
Donaldson et al., RuvAB and RecG are not essential for the recovery of DNA synthesis following UV-induced DNA damage in *Escherichia coli*. Genetics 2004, 166(4):1631-40.
Drlica et al., "Mechanisms of quinolone action". In Quinolone Antimicrobial Agents, 3rd ed. 2003, Edited by Hooper and Rubistein.
Drlica et al., Microbiol. Mol. Biol. Rev. 1997, 61: 377-392.
Dutreix et al., J. Bacterol. 1989, 171: 2415.
Dwyer et al., Superoxide and hydroxyl radicals contribute to gyrase inhibitor-mediated cell death in *E. Coli*, Mol. Syst. Biol. 2007, 3: 91.
Eggler et al., The Rad51-dependent pairing of long DNA substrates is stabilized by replication protein A. J Biol Chem. 2002, 277(42):39280-8.
Esposito et al., The *Escherichia coli* Fis protein stimulates bacteriophage lambda integrative recombination in vitro. J. Bacteriol. 2003, 185(10):3076-80.
Everett et al., Contributions of individual mechanisms to fluoroquinolone resistance in 36 *Escherichia coli* strains isolated from humans and animals. Antimicrob Agents Chemother. 1996, 40:2380-2386.
Flores et al., The DNA repair helicase UvrD is essential for replication fork reversal in replication mutants. EMBO Rep. 2004, 5(10):983-8.
Flores et al., A fork-cleaning role for UvrD. Mol Microbiol. 2005, 57(6):1664-75.
Fournier et al., Selective targeting of topoisomerase IV and DNA gyrase in *Staphylococcus aaureus*: different patterns of quinolone-induced inhibition of DNA synthesis. Antimicrob Agents Chemother. 2000, 44(8):2160-5.
Fukui et al., The Structure of Hinokiflavone, a new type of bisflavonoid. J. Am. Chem. Soc. 1959, 81(23): 6331.
Greenfield et al., Current therapy and the develpoment of therapeutic options for the treatment of diseases due to bacterial agents of potential biowarfare and bioterrorism. Curr Opin Investig Drugs. 2004, 5(2):135-40.
Guzman et al., J. Bacteriol. 1995, 177: 4121-4130.
Hall et al., Helicase motifs: the engine that powers DNA unwinding. Mol Micriobiol 1999, 34: 867-877.
Hancock et al., Adv. Microb. Physiol. 1995, 37: 135-137.
Hojgaard et al., Norfloxacin-induced DNA cleavage occurs at the dif resolvase locus in *Escherichia coli* and is the result of interaction with topoisomerase IV. Mol Microbiol. 1999, 33(5):1027-36.
Howard et al., Disruption of a topoisomerase-DNA cleavage complex by a DNA helicase. Proc Natl Acad Sci U S A. 1994, 91(25):12031-5.
Husain et al., Interaction between the To1C and AcrA proteins of a multidrug efflux system of *Escherichia coli*. J Bacteriol. 2004, 186(24):8533-6.
Jude et al., Posttranscriptional control of quorum-sensing-dependent virulence genes by DksA in *Pseudomonas aeruginosa*. J. Bacteriol. 2003, 185(12):3558-66.
Karlin et al., Evolutionary conservation of RecA genees in relation to protein structure and function. J Bacteriol. 1996, 178(7):1881-94.

(56) References Cited

OTHER PUBLICATIONS

Kawabata et al., Role of recA/RAD51 family proteins in mammals. Acta Med Okayama. 2005, 59(1):1-9.
Keith et al., Multi-target lead discovery for networked systems. Curr. Drug. Discov. 2004, 19-23.
Khoudursky et al., The mechanism of inhibition of topoisomerase IV by quinolone antibacterials. J Biol Chem. 1998, 273(42):27668-77.
Kidane et al., Intracellular protein and DNA dynamics in competent *Bacillus subtilis* cells. Cell 2005, 122(1):73-84.
Kim et al., Hepatitis C virus NS3 RNA helicase domain with a bound oligonucleotide: the crystal structure provides insights into the mode of unwinding. Structure 1998, 6(1):89-100.
Kleinkauf et al., Crit. Rev. Biotechnol., 1988, 8(1): 1-32.
Ko et al., *J. Bacteriol*. 2002, 184: 3917-22.
Kohanski et al., "A common mechanism of cellular death induced by bactericidal antibiotics", Cell 2007, 130: 797-810.
Komp et al., Mutation rate and evolution of fluoroquinclone resistance in *Escherichia coli* isolates from patients with urinary tract infections. Antimicrob Agents Chemother. 2003 47:3222-3232.
Koronakis, To1C—the bacterial exit duct for proteins and drugs. FEBS Lett. 2003, 555(1):66-71.
Kosa et al., RecN and RecG are required for *Escherichia coli* survival of Bleomycin-induced damage. Mutat Res. 2004, 554(1-2):149-57.
Krejci et al., DNA helicase Srs2 disrupts the Rad51 presynaptic filment. Nature 2003, 423(6937):305-9.
Lai et al., Beta-ketoacyl carrier protein synthase III (FabH) is essential for bacterial fatty acids synthesis. J Biol Chem. 2003, 278(51):51494-503.
Lee et al., Inhibition of the *Escherichia coli* RecA protein: zinc(II), copper(II) and mercury(II) trap RecA as inactive aggregates. J Inorg Biochem. 2004, 98(11):1981-6.
Lee et al., Appl. Environ. Microbiol. 1998, 64: 4796-802.
Lee et al., Appl. Environ. Microbiol. 1999, 65: 1883-90.
Lei et al., Org. Lett. 2004, 6: 795-798.
Leonardo et al., J. Bacteriol. 1996, 178: 6013-6018.
Lesic et al., Horizional transfer of the high-pathogenicity island of *Yersinia pseudotuberculosis*. J Bacteriol. 2005, 187(10):3352-8.
Lewis, Antiretroviral combination therapy for HIV infection. Dent Update. 2003. 30(5):242-7.
Lewis, Microbiol. Mol. Biol. Rev. 2002, 64: 503-514.
Lewis et al., Compartmentalization of transcription and translation. in *Bacillus subtilis* EMBO J. 2000, 19(4):710-8.
Link et al., J. Bacteriol, 1997, 179:6228-37.
Lutz et al., Nucleic Acids Research 1997. 25: 1203-1210.
Magnusson et al., ppGpp: a global regulator in *Escherichia coli*. Trends Microbiol. 2005, 13(5):236-42.
McGrew et al., Molecular design and functional organization of the RecA protein. Crit Rev Biochem Mol Biol. 2003, 38(5):385-432. Review. Erratum in: Crit Rev Biochem Mol Biol. 2004, 39(1):69.
Meddows et al., RecN protein and transcription factor DksA combine to promote faithful recombinational repair of DNA double-strand breaks. Mol. Microbiol. 2005, 57(1):97-110.
Mei et al., Mol. Microbiol. 1997, 26: 399-407.
Metcalf et al., Plasmid 1996, 35: 1-13.
Meyn et al., A protease inhibitor blocks SOS functions in *Escheriehia coli*: antipain prevents lambda repressor inactivation, ultraviolet mutagenesis, and filamentous growth. Proc Natl Acad Sci U S A 1977, 74(3):1152-6.
Mirsalikhova et al., Khimiya Prirodnykh Soedinenii. No. 1, 1977, pp. 44-46.
Morel et al., Antipairing and strand transferase activities of *E. Coli* helicase II (UvrD). Nucleic Acids Res. 1993, 21(14):3205-9.
Murphy, J. Bacteriol. 1998, 179: 6228-37.
Nair et al., Cloning and expression in *Escherichia coli* of a recA homologue from *Mycobactrium tuberculosis*. J Gen Microbiol. 1991, 137(10):2409-14.
Nastri et al., Mutational analysis of the RecA protin LI region identifies this area as a probable part of the co-protease substrate binding site. Mol Microbiol. 1997, 25(5):967-78.

Nie et al., Structure-based design, synthesis, and study of potent inhibitors of beta-ketoacyl-acyl carrier protein synthase III as potential antimicrobial agents. J Med Chem. 2005, 48(5):1596-609.
Penkey et al., Clin. Infect. Dis. 2004, 38: 864-870.
Paul et al., DksA: a critical component of the transcription initiation machinery that potentiates the regulation of rRna promoters by ppGpp and the initiating NTP. Cell 2004, 118(3):311-22.
Paul et al., DksA potentiates direct activation of amino acid promotors by ppGpp. Proc Natl Acad Sci U S A 2005, 102(22):7823-8.
Perlman et al., Annu. Rev. Biochem. 1971, 40: 449-464.
Perron et al., DksA represses ribosomal gene transcription in *Pseudomonas aeruginosa* by interacting with RNA polymerase on ribosomal promoters. Mol. Microbiol. 2005, 56(4):1087-102.
Robu et al., Situational repair of replication forks: roles of RecG and RecA proteins. J Biol Chem. 2004, 279(12):10973-81.
Ronald and Low (Eds.), "*Fluoroquinolone Antibiotics*", Birkhauser Verlag, Basel, 2003.
Rossbach et al., Crystal structure of THEP1 from the hyperthermophile *Aquifex aeolicus*: a variation of the RecA fold. BMC Struct Biol. 2005, 5(1):7.
Saiki et al., Antimicrob. Agents Chemother. 1999, 43: 1574-1577.
Shea et al., Distinct effects of the UvrD helicase on topoisomerasequinolone-DNA ternary complexes. J Biol Chem. 2000, 275(19):14649-58.
Shea et al., The RuvAB branch migration complex can displace topoisomerase IV.quinolone.DNA ternary complexes. J Biol Chem. 2003, 278(48):48485-90.
Sheehan et al., The history of quinolones in Fluoroquinolone Antibiotics 2003. Edited by Ronald AR and Low DE.
Shen et al., *Curr. Pharm. Des.*, 3:169-176.
Shinohara et al., Rad51/RecA protein families and the associated proteins in eukaryotes Mutat Res. 1999, 435:13-21.
Singleton et al., Crystal structure of RecBCD enzyme reveals a machine for processing DNA breaks. Nature 2004, 432(7014):187-93.
Singleton et al., Strutural analysis of DNA replication fork reversal by RecG. Cell 2001, 107(1):79-89.
Spek et al., J. Bacteriol. 2001, 183: 131-138.
Steffen et al., Complete inhibition of *Streptococcus pneumoniae* RecA protein-catalyzed ATP hydrolsis by single-stranded DNA-binding protein (SSB protein). J. Biol. Chem. 2002, 277(17):14493-14500.
Stermitz et al., Planta Medica 2002, 68(12):1140-1141.
Stohl et al., *Escherichia coli* RecX inhibits RecA recombinase and coprotease activities in vitro and in vivo. J Biol Chem. 2003, 278(4):2278-85.
Story et al., Structure of the RecA protein-ADP complex. Nature 1992, 355: 374-376.
Story et al., The structure of the *E. coli* recA protein monomer and polymer. Nature 1992, 355(6358):318-25.
Suchov et al., *Mol Gen Mikrobiol Virusol*. 5: 34-9.
Sutton et al., The SOS response: recent insights into u.nruDC-dependent mutagenessis and DNA damage tolerance. Annu Rev Genet. 2000, 34:479-497.
Tanaka et al., ATPase/helicase motif mutants of *Escherichia coli* priA protein essential for recombination-dependent DNA replication. Genes Cells. 2003. 8(3):251-61.
Tatum et al., Microb. Pathog. 1993, 14: 177-185.
Thresher et al., intercalators promote the binding of RecA protein to double-stranded DNA. Proc. Natl. Acad. Sci. USA 1990, 5056-5060.
Tomasz, Annu. Rev. Microbio. 1979, 33: 113-137.
Trautinger et al., RNA polymerase modulators and DNA repair activities resolve conflicts between DNA replication and transcription. Mol Cell. 2005, 19(2):247-58.
Trucksis et al., J Bacteriol. 1991, 173(18):5864-60.
Tsuki et al., Antimicrob. Agents Chemother. 2003, 47: 2507-2512.
Umehara et al., Rational design of dual-functional aptamers that inhibit the protease and helicase activities of HVC NS3. J Biochem (Tokyo). 2005, 137(3):339-47.
Van Bambeke et al., "Quinolones in 2005: an update", *Clin Microbiol. Infect.* 2005, 11: 256-280.

(56) References Cited

OTHER PUBLICATIONS

Vanloock et al., Complexes of RecA with LexA and RecX differentiate between active and inactive RecA nucleoprotein filaments. J Mol Biol. 2003, 333(2):345-54.

Vanloock et al., ATP-mediated conformational changes in the RecA filament. Structure 2003, 11(2):187-96.

Veaute et al., UvrD helicase, unlike Rep helicase, dismantles RecA nucleoprotein filaments in *Escherichia coli*. EMBO J. 2005,24(1):180-9.

Veautre et al., The Srs2 helicase prevents recombination by disrupting Rad51 nucleoprotein filaments. Nature 2003, 423(6937):309-12.

Walsh, Nature Rev. Microbilo. 2003, 1: 65-70.

Walsh, Nature 2000, 406: 75-781.

Weber et al., Crystallization of recA protein from *Proteus mirabilis*. J Mol Biol. 1986, 188(1):109-10.

Wei et al., Testing a flexible receptor docking algorithm in a model binding site. J Mol Biol 2004, 337:1161-82.

Wright et al., Proc. Natl. Acad Sci. USA 2005, 102: 1691-1696.

Wu et al., J. Biol. Chem. 2005, 280: 722.

Wu et al., Crystal structure of archaeal recombinase RADA: a snapshot of its extended conformation. Mol Cell. 2004, 15(3):423-35.

Wu et al., Crystal structure of an ATPase-active form of Rad51 hornolog from *Methanococcus voltae*. Insights into potassium dependence. J Biol Chem. 2005, 280(1):722-8.

Xing et al., Crystal structures of *Escherichia coli* RecA in complex with MgADP and MnAMP-PNP. Biochemistry 2004, 43(51):16142-52.

Xu et al., Nuc. Acids Res. 2001, 29:5058.

Yang et al., Comparison of bacteriophage T4 UvsX and human Rad51 filaments suggests that RecA-like polymers may have eveolved independently. J Mol Biol. 2001, 312(5):999-1009.

Yu et al., The RecA hexamer is a structural homologue of ring helicases. Nat Struct Biol. 1997, 4(2):101-4.

Yu et al., Domain structure and dynamics in the helical filaments formed by RecA and Rad51 on DNA. Proc Natl Acad Sci U S A 2001, 98(15):8419-24.

Cushnie et al, "Antimicroial activity of flavonoids", Internationai J. of Antimicrobial Agents 26, pp. 343-356, 2005.

Lin et al, "Antiviral Activities of Biflavonoids", Planta Medica 65, pp. 120-125, 1999.

Pegnyemb et al, "Antimicrobial biflavonoids from the aerial parts of *Ouratea sulcata*", Phytochemistry 66, pp. 1922-1926, 2005.

Wolfson et al, "Fluoroquinolone Antimicrobial Agents", Clinical Microbiology Reviews, pp. 378-424, 1989.

Fenlon et al., Comparative In vitro Activities of Ciprofloxacin and other 4-Quinolones against *Mycobacterium tuberculosis* and *Mycobacterium intracellulare*. Antimicrobial Agents and Chemotherapy, 1986, 386-388.

Karlowsky et al., Prevalence and antimicrobial susceptibilities of bacteria isolated from blood cultures of hospitalized patients in the United States in 2002. Annuals of Clinical Microbiology and Antimicrobials, 2004, 3; 1-8.

Zeiler et al., In vitro and in vivo Activity of Ciprofloxacin. Eur. J. Clin. Microboiol., 1981, 3(4); 339-343.

\* cited by examiner

| Structure | Database ID | Chemical Name | Percent Inhibition | µg/mL | IC$_{50}$ (µg/mL) |
|---|---|---|---|---|---|
| 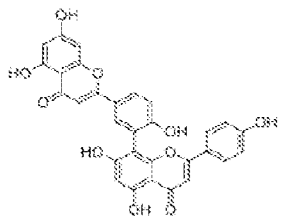 | IF_02-B09 | Amentoflavone | 109 | 100 | 5 |
| 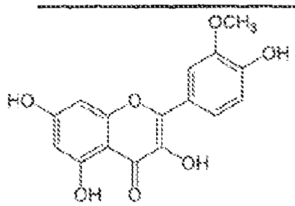 | IF_01-A06 | ISORHAMNETIN | 100 | 100 | |
| 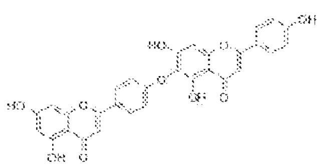 | IF_01-G05 | HINOKIFLAVONE | 90 | 100 | 1 |
| 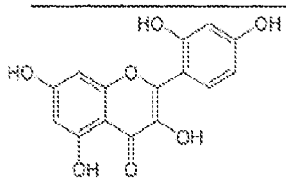 | IF_02-A10 | MORIN | 88 | 100 | 10 |
| 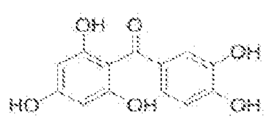 | IF_02-B08 | Maclurin | 86 | 100 | 15 |
| 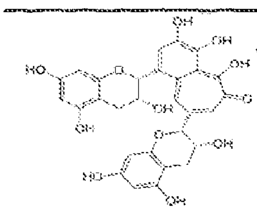 | IF_02-E07 | theaflavin | 86 | 50 | 1.5 |
| 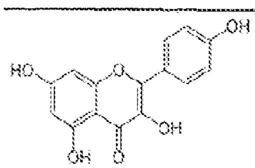 | IF_02-A06 | KAEMPFEROL | 70 | 100 | 5 |

| Structure | Database ID | Chemical Name | Percent Inhibition μg/mL | IC$_{50}$ (μg/mL) |
|---|---|---|---|---|
| (structure) | CD_01-G08 | quercetin dihydrate | 67 | 200 / 1 |
| (structure) | IF_02-A08 | 6-HYDROXYAPIGENIN | 65 | 100 / 3 |
| (structure) | IF_02-A05 | 3,7,4'-TRIHYDROXYFLAVONE | 63 | 100 / 10 |
| (structure) | CD_01-C03 | | 61 | 200 / 100 |
| (structure) | IF_02-E03 | apigenin | 56 | 50 / 3 |
| (structure) | IF_02-A03 | QUERCETAGETIN | 55 | 100 / 1.6 |
| (structure) | IF_01-A02 | APIGENIN-7-O-GLUCOSIDE | 48 | 100 / 1 |

FIG. 2B 4-oxo-1,4-dihydroquinoline 4-oxo-1,4-dihydronaphthyridine

4-Quinolone

4-oxo-1,4-dihydroquinoline 4-oxo-1,4-dihydronaphthyridine

2-Pyridone

4H-4-oxoquinolizine 6H-6-oxo-pyrido[1,2-a]pyrimidine

| R |
|---|
|  |
|  |
|  |
|  |
|  |

Novel binding site situated around

*R324*

*F270 Y271*

*R85*

*K310*

New Site

| 1xmv | 1g18 | 1ubc | 1xp8 |
|---|---|---|---|
| site detected | site detected | site detected | site detected |
| E. coli | M. tuberculosis | M. smegmatis | D. radiodurans |
| Gram- | Gram+ | Gram+ | Gram+ |

The novel site is found in all species investigated
– Gram positive and negative –

With little changes in sequence

→ Broad spectrum recA inhibitors possible

Figure 19

RECA INHIBITORS WITH ANTIBIOTIC ACTIVITY, COMPOSITIONS AND METHODS OF USE

RELATED APPLICATIONS

This application is a national phase entry application under 35 U.S.C. §371 of PCT International Application No. PCT/US2007/003712, filed on Feb. 13, 2007, which claims benefit under 35 U.S.C §119(e) of U.S. Provisional Application No. 60/772,648 filed on Feb. 13, 2006 and entitled "Compositions and Methods for Antibiotic Potentiation and Drug Discovery", and U.S. Provisional Application No. 60/835,596 filed on Aug. 4, 2006 and entitled "RecA Inhibition", the contents of each of these applications is incorporated herein by reference in their entirety.

BACKGROUND OF THE INVENTION

The emergence of resistance to antibacterial agents is a growing problem for human and animal health, and new drugs to treat infections are urgently needed. Particularly desirable are drugs that can treat infections caused by microorganisms that display resistance to currently used antibiotics. Efforts to overcome the growing problem of resistance have included modification of known antibiotics, classical screening of new compound libraries and natural product libraries, and genomic efforts to identify novel targets to which no cross resistance with existing antibiotics would be anticipated. Even with this significant antibiotic discovery effort, only a few agents that represent new chemical classes of antibiotic agents have been approved by regulatory agencies in recent years. In addition, few antibiotics that are effective against bacteria that have developed resistance to currently used antibiotics are in clinical development. Furthermore, a number of potent antibiotic agents have been found to be too toxic for clinical use or to have significant side effects that limit their therapeutic utility.

There is clearly a need in the art both for new agents to combat microbial infection and for new approaches to antibiotic drug discovery.

SUMMARY OF THE INVENTION

The present invention encompasses the recognition that RecA is a virulence factor and a stand alone target, and that certain inhibitors of RecA are uniquely useful as antibiotics. According to the present invention, certain RecA inhibitors may be used alone as antibiotics, may be used in combination with one or more other agents with antibiotic activities, or both. When RecA inhibitors are administered in combination with one or more such antibiotic agents, the antibiotic agent(s) may often be utilized at a lower dose, and/or less frequent dosing regimen than their conventional dose and/or schedule. In certain embodiments, this is employed to reduce the antibiotic(s)'s toxicity. When a RecA inhibitor is used in combination with an antibiotic agent, the RecA inhibitor and antibiotic agent may be administered substantially simultaneously using the same or different routes of administration. Alternatively, the RecA inhibitor and antibiotic agent may be administered sequentially, using the same or different routes of administration. In certain preferred embodiments, the RecA inhibitor is administered prior to administration of the antibiotic agent.

In some embodiments, inventive RecA inhibitors have broad spectrum activity in that they inhibit one or more activities of RecA (or its relevant homolog) from a wide range of different organisms (i.e., at least two different organisms or organisms from two different families). In other embodiments, inventive RecA inhibitors have a narrow spectrum activity in that they inhibit one or more activities of RecA (or its relevant homolog) from a specific family of organisms or from a specific organism. In certain preferred embodiments, inventive RecA inhibitors inhibit one or more activities of RecA (or its relevant homolog) from a disease-causing organism (in particular an organism that causes disease in a mammalian, e.g., a human). In some embodiments, however, the RecA inhibitors (which may be broad spectrum with regard to microbes) do not inhibit RecA (or the relevant RecA homolog) from one or more higher organisms (e.g., mammals, humans).

In certain embodiments of the present invention, inventive RecA inhibitors have the following structure:

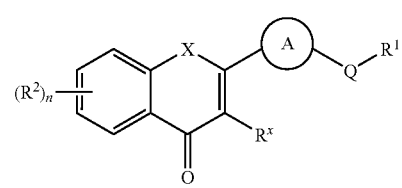

I or a pharmaceutically acceptable salt or derivative thereof, wherein:

X is oxygen, sulfur, or N(R);

n is 0 to 4;

$R^1$ is hydrogen, or an optionally substituted group selected from a $C_{1-6}$ aliphatic group, a monocyclic 3-8 membered saturated, partially unsaturated, or aryl ring having 0-4 heteroatoms independently selected from nitrogen, oxygen, or sulfur, or a bicyclic 8-10 membered saturated, partially unsaturated, or aryl ring having 0-5 heteroatoms independently selected from nitrogen, oxygen, or sulfur;

each $R^2$ is independently halogen, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, $SO_2N(R^3)_2$;

each $R^3$ is independently hydrogen or an optionally substituted group selected from a $C_{1-6}$ aliphatic group, a monocyclic 3-8 membered saturated, partially unsaturated, or aryl ring having 0-4 heteroatoms independently selected from nitrogen, oxygen, or sulfur, or a bicyclic 8-10 membered saturated, partially unsaturated, or aryl ring having 0-5 heteroatoms independently selected from nitrogen, oxygen, or sulfur;

Q is a valence bond or a bivalent, saturated or unsaturated, straight or branched $C_{1-6}$ hydrocarbon chain, wherein 0-2 methylene units of Q are independently replaced by —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—;

each R is independently hydrogen or an optionally substituted aliphatic group;

$R^x$ is R or OR; and

Ring A is an optionally substituted 3-8 membered bivalent, saturated, partially unsaturated, or aryl monocyclic ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In other embodiments, inventive RecA inhibitors have the structure of formula II:

or a pharmaceutically acceptable salt or derivative thereof, wherein:

$Cy^1$ is a an optionally substituted 5-6 membered aryl ring having 0-3 heteroatoms independently selected from nitrogen, oxygen, or sulfur;

$L^1$ is a valence bond, a $C_{1-6}$ bivalent saturated, unsaturated, straight or branched hydrocarbon chain, —N(R)—, —N(R)SO$_2$—, —N(R)SO$_2$N(R)—, —N(R)C(O)—, —C(O)N(R)—, or —N(R)C(O)N(R)—;

each R is independently hydrogen or an optionally substituted $C_{1-6}$ aliphatic group;

$Cy^2$ is an optionally substituted 6-membered aryl ring having 0-2 nitrogen atoms, an 8-10 membered bicyclic heteroaryl ring having 1-3 heteroatoms independently selected from nitrogen, oxygen, or sulfur, or an optionally substituted 5-membered heteroaryl ring having 1-2 heteroatoms independently selected from nitrogen, oxygen, or sulfur;

$L^2$ is a $C_{1-6}$ bivalent saturated, unsaturated, straight or branched hydrocarbon chain, —CH$_2$CH$_2$C(=W)N(R)N(R)C(=W)—, —N(R)C(=W)N(R)C(=W)C(R)$_2$W—, —C(=W)N(R)N(R)C(=W)N(R)—, —C(=W)N(R)N(R)C(=W)N(R)CH=CH$_2$, or —C(=W)N(R)C(=W)N(R)—, wherein each W is independently oxygen or sulfur; and $Cy^3$ is an optionally substituted 6-membered aryl ring having 0-2 nitrogen atoms.

In certain embodiments, inventive RecA inhibitors have a structure depicted in any one of FIGS. 2-4.

The present invention further provides methods and systems for identifying, making, characterizing, and/or using inventive RecA inhibitors.

BRIEF DESCRIPTION OF THE DRAWING

FIGS. 2A and 2B presents chemical structures and IC$_{50}$ data for 14 compounds that showed at least 50% inhibition of RecA ATPase activity in the luciferase assay described in Example 1.

FIG. 19 illustrates the cross-species conservation of the hinokiflavone binding site.

DEFINITIONS

Figure 1:
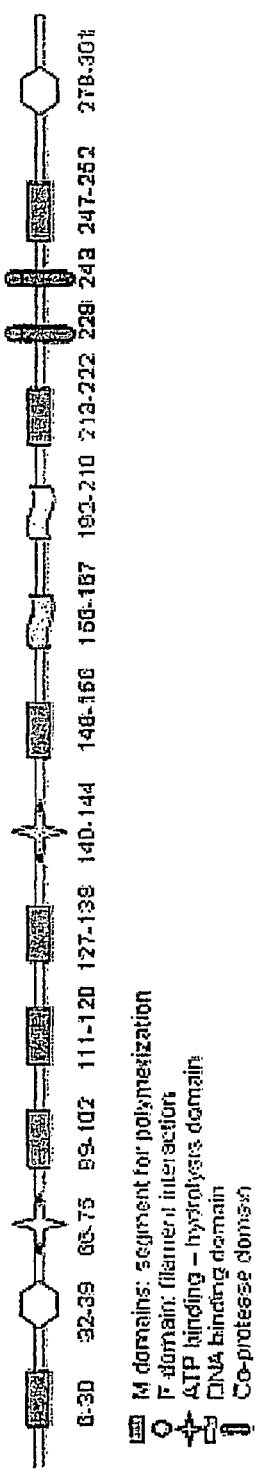
FIG. 1 is a schematic diagram showing functional modules of the *E. coli* RecA protein. Amino acid numbers bracketing modules associated with particular functional activities are shown. These modules are highly conserved among bacteria. The figure is taken from Karlin & Bricchiere, *J. Bacteriol.* 178:1881, 1996, and is not drawn to scale.

Aliphatic: The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

Antibiotic agent: The term "antibiotic agent" refers to an agent that inhibits and/or stops growth and/or proliferation of one or more species of microorganism (e.g., bacteria or fungus). An antibiotic agent may display activity in vitro (e.g., when contacted with cells in culture), in vivo (e.g., when administered to a subject at risk of or suffering from an infection), or both. The term "antibiotic agent" may be used to refer to bactericidal agents (i.e., agents that kill bacteria) and/or bacteriostatic agents (i.e., agents that inhibit or stop bacterial growth or proliferation but does not kill the cells).

Aryl: The term "aryl", used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains three to seven ring members. The term "aryl" may be used interchangeably with the term "aryl ring".

Conventional dose: A "conventional dose" of an antibiotic agent means a dose that is (i) in the case of humans or animals, approved by a regulatory body such as, for example, the United States Food and Drug Administration; (ii) recommended on the package insert; (iii) in the case of humans, recommended in Goodman and Gilman, supra; Katzung, supra, and/or *The Merck Manual of Diagnosis and Therapy*, 17$^{th}$ ed. (1999), or the 18$^{th}$ ed (2006) following its publication, Mark H. Beers and Robert Berkow (eds.), Merck Publishing Group; and/or (iv) in the case of animals, recommended in *The Merck Veterinary Manual*, 9$^{th}$ ed., Kahn, C. A. (ed.), *Merck Publishing Group*, 2005. It will be appreciated that a conventional dose may be modified appropriately for an individual subject taking into account, for example, factors such as the subject's age, diet, renal and/or hepatic function, other medications, other diseases or conditions (i.e., diseases or conditions other than the infection for which an antibiotic agent is administered), past experience with the antibiotic agent, etc.

Effective amount: In general, an "effective amount" of a biologically and/or pharmacologically active agent is an amount sufficient to achieve a desired biological and/or pharmacological effect when delivered to a cell or organism according to a selected administration form, route, and/or schedule. As will be appreciated by those of ordinary skill in this art, the absolute amount of a particular agent that is effective may vary depending on such factors as the desired biological endpoint, the agent to be delivered, the target tissue, etc. Those of ordinary skill in the art will further understand that an "effective amount" may be administered in a single dose, or may be achieved by administration of multiple doses.

For example, an effective amount of an antibiotic agent may be an amount sufficient to achieve one or more of the following: (i) inhibit microbial growth in culture or in vivo; (ii) reduce the severity of or prevent one or more symptoms or signs of an infection; (iii) significantly reduce the risk of recurrence of an infection; (iv) significantly reduce the risk of a clinically significant infection in a subject who has been exposed to an infectious agent, etc.

Comparably, an effective amount of a potentiating agent may be an amount sufficient to achieve the same level of antibiotic activity with a particular antibiotic agent as is achieved when that antibiotic agent is administered at its conventional dose, in circumstances where the antibiotic agent is administered at a reduced dose as compared with its conventional dose.

An effective amount of a RecA inhibitor according to the present invention may be, for example, (i) an amount sufficient to act as an antibiotic agent; (ii) an amount sufficient to inhibit one ore more activities of RecA (or a relevant homolog); (iii) an amount sufficient to potentiate activity of one ore more antibiotic agents (e.g., with which the RecA inhibitor is administered in combination); and/or (iv) an amount sufficient to reduce the incidence of resistance developed to another antibiotic agent (e.g., with which the RecA is administered in combination).

Growth: The term "growth", as used herein, refers to an increase in microbial biomass. "Proliferation" (see below) refers to an increase in microbial number. Since bacterial proliferation, rather than mere increase in cell mass without cell division, is usually of primary concern, and since under most circumstances of interest herein proliferation is accompanied by an increase in microbial biomass, the term "growth" is generally understood to mean "proliferation", and the two terms are used interchangeably herein although it is recognized that different assays may measure either or both of these parameters. For example, optical density reflects biomass and does not specifically reflect cell number, whereas an assay based on detecting colonies formed from individual cells reflects cell number rather than biomass.

Heteroatom: The term "heteroatom" means one or more of oxygen, sulfur, nitrogen, phosphorus, or silicon. This includes any oxidized form of nitrogen, sulfur, phosphorus, or silicon; the quaternized form of any basic nitrogen, or; a substitutable nitrogen of a heterocyclic ring including =N— as in 3,4-dihydro-2H-pyrrolyl, —NH— as in pyrrolidinyl, or =N(R$^+$)— as in N-substituted pyrrolidinyl.

In combination: The phrase "in combination", as used herein, means with respect to administration of first and second agents, administration performed such that (i) a dose of the second agent is administered before more than 90% of the most recently administered dose of the first agent has been metabolized to an inactive form or excreted from the body; or (ii) doses of the first and second agents are administered within 48 hours of each other, or (iii) the agents are administered during overlapping time periods (e.g., by continuous or intermittent infusion); or (iv) any combination of the foregoing. The agents may, but need not be, administered together as components of a single composition. The agents may be administered individually at substantially the same time (by which is meant within less than 10 minutes of one another). The agents may be administered individually within a short time of one another (by which is meant less than 3 hours, sometimes less than 1 hour, apart). The agents may, but need not, be administered by the same route of administration. When administered in combination with a second agent, the effective concentration of a first agent needed to elicit a particular biological response may be less or more than the effective concentration of the first agent when administered in the absence of the second agent, thereby allowing an adjustment of the amount dose of the first agent relative to the amount that would be needed if the first agent were administered in the absence of the second agent. In some embodiments of the invention, a lower amount of first agent (e.g., antibiotic agent) is required in the presence of the second agent (e.g., inventive RecA inhibitor). The effects of multiple agents may, but need not be, additive or synergistic. One or more of the agents may be administered multiple times.

Infection: The term "infection", as used herein, refers to the invasion of a host, whether the host is a vertebrate, invertebrate, fish, plant, bird, or mammal, by pathogenic microbes, e.g., bacteria, fungi, and protists. The term encompasses excessive growth of microbes that are normally present in or on the body of a mammal or other organism. More generally, a microbial infection can be any situation in which the presence of a microbial population(s) is damaging to a host organism. Thus, an organism is "suffering" from a microbial infection when excessive numbers of a microbial population are present in or on the organism's body, or when the effects of the presence of a microbial population(s) is damaging the cells or other tissue of an organism. The agents and compositions of certain embodiments of the invention are also useful in treating microbial growth or contamination of cell cultures or other media, or inanimate surfaces or objects, and nothing herein should limit the invention to treatment of higher organisms, except when explicitly so specified in the claims.

Isolated: As used herein, agent or entity is "isolated" if it is separated from at least some materials or components with which it is associated in nature or when initially generated. In general, such separation involves activity of the hand of man.

Minimal inhibitory concentration (MIC): The term "minimal inhibitory concentration" (MIC) are used herein consistently with its use in the art, i.e., to indicate the concentration of an agent that will inhibit bacterial proliferation (growth) (MIC). MIC values may be for example, the concentration of agent that inhibits visible growth or may be expressed as $MIC_{50}$, $MIC_{90}$ or $MIC_{99}$ values i.e., the concentration of an agent that reduces bacterial proliferation to 50% or less, 10% or less, or 1% or less, respectively, of the control value that would occur in the absence of the agent. As is well known in the art, MIC can be measured by a variety of methods, including automated and non-automated methods. Suitable methods are described in publications of the Clinical Laboratory Standards Institute (CLSI), formerly the National Committee for Clinical Laboratory Standards (NCCLS), as set forth in NCCLS: Performance Standards documents.

Pharmaceutically acceptable derivative: According to the present invention, a pharmaceutically acceptable derivative of a particular chemical compound includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof. Thus, pharmaceutically acceptable derivatives can include salts, prodrugs, and/or metabolites of relevant compounds. The phrase "pharmaceutically acceptable derivative" may also encompass quaternization of any basic nitrogen-containing groups of the compounds disclosed herein. Water or oil-soluble or dispersable products may be obtained by such quaternization.

Pharmaceutically acceptable salt: As used herein, the term "pharmaceutically acceptable salt" refers to those salts which are, within the scope of sound medical judgment, suitable for use in contact with the tissues of humans and lower animals without undue toxicity, irritation, allergic response and the like, and which are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorally active metabolite or residue thereof. As used herein, the term "inhibitorally active metabolite or residue thereof" means that a metabolite or residue thereof acts as a RecA inhibitor.

A wide variety of appropriate pharmaceutically acceptable salts are well known in the art. For example, S. M. Berge et al., describe pharmaceutically acceptable salts in detail in *J. Pharmaceutical Sciences*, 66:1, 1977, incorporated herein by reference. Pharmaceutically acceptable salts of the compounds of this invention include those derived from suitable inorganic and organic acids and bases.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Examples of pharmaceutically acceptable salts derived from appropriate bases include alkali metal, alkaline earth metal, ammonium and $N^+(C_{1-4} alkyl)_4$ salts.

Representative pharmaceutically acceptable alkali or alkaline earth metal salts include sodium, lithium, potassium, calcium, magnesium, and the like.

Further pharmaceutically acceptable salts include, when appropriate, nontoxic ammonium, quaternary ammonium, and amine cations, for example formed using counterions such as halide, hydroxide, carboxylate, sulfate, phosphate, nitrate, lower alkyl sulfonate and aryl sulfonate.

Physiologically acceptable carrier or excipient: As used herein, the term "physiologically acceptable carrier or excipient" refers to a carrier medium or excipient which does not interfere with the effectiveness of the biological activity of the active ingredients and which is not excessively toxic to the host at the concentrations at which it is administered. The term includes solvents, dispersion media, coatings, antibacterial and antifungal agents, isotonic agents, absorption delaying agents, and the like. The use of such media and agents for the formulation of pharmaceutically active substances is well-known in the art (see, for example, *"Remington's Pharmaceutical Sciences"*, E. W. Martin, $18^{th}$ Ed., 1990, Mack Publishing Co.: Easton, Pa., which is incorporated herein by reference in its entirety).

Potentiate: The term "potentiate", as used herein, means to enhance or increase at least one biological effect or activity of a biologically and/or pharmacologically active agent so that either (i) a given concentration or amount of the agent results in a greater biological effect or activity when the agent is potentiated than the biological effect or activity that would result from the same concentration or amount of the agent when not potentiated; or (ii) a lower concentration or amount of the agent is required to achieve a particular biological effect or activity when the agent is potentiated than when the agent is not potentiated; or (iii) both (i) and (ii). The biological effect or activity may be, for example, the ability to catalyze or inhibit one or more chemical reactions, the ability to activate or inhibit a biological or biochemical pathway, the ability to reduce or inhibit microbial proliferation, the ability to kill a microorganism, etc. An agent whose presence potentiates another agent may be referred to as a "potentiating agent". A potentiating agent may show biological activity by itself, or may exhibit biological activity only when used in combination with a biologically and/or pharmacologically active agent.

Proliferation: The term "proliferation" refers to an increase in microbial number. Since bacterial proliferation, rather than mere increase in cell mass without cell division, is usually of primary concern, and since under most circumstances of interest herein proliferation is accompanied by an increase in microbial biomass, the term "growth" is generally understood to mean "proliferation", and the two terms are used interchangeably herein although it is recognized that different assays may measure either or both of these parameters. For example, optical density reflects biomass and does not specifically reflect cell number, whereas an assay based on detecting colonies formed from individual cells reflects cell number rather than biomass.

Protist. The term "protist" refers to any member of a diverse group of organisms, comprising those eukaryotes that are not animals, plants or fungi. Protists can be unicellular or multicellular. Protists are grouped in three subcategories: animal-like protists, fungus-like protists, and plant-like protists.

Purified: As used herein, the term "purified" refers to agents or entities that have been separated from most of the components with which they are associated in nature or when originally generated. In general, such purification involves action of the hand of man. Purified agents or entities may be partially purified, substantially purified, or pure. Such agents or entities may be, for example, 50%, 60%, 70%, 75%, 80%, 85%, 90%, 95%, 96%, 97%, 98%, 99%, or more than 99% pure.

RecA Inhibitor: According to the present invention, an agent is a RecA inhibitor if one or more RecA activities is reduced in the agent's presence as compared with its absence, or if the level or amount of RecA protein or gene product is reduced in the agent's presence as compared with its absence. In certain embodiments, RecA inhibitors act directly on RecA in that they physically interact with RecA. In other embodiments, inhibitors act indirectly on RecA.

Small Molecule: In general, a small molecule is understood in the art to be an organic molecule that is less than about kilodaltons (KDa) in size. In some embodiments, the small molecule is less than about 3 KDa, 2 KDa, or 1 KDa. In some embodiments, the small molecule is less than about 800 daltons (Da), 600 Da, 500 Da, 400 Da, 300 Da, 200 Da, or 100 Da. In some embodiments, small molecules are non-polymeric. In some embodiments, small molecules are not amino acids. In some embodiments, small molecules are not nucleotides. In some embodiments, small molecules are not saccharides.

Subject: A "subject", as used herein, is an individual to whom an agent is to be delivered, e.g., for experimental, diagnostic, and/or therapeutic purposes. Subjects of interest herein include animals, particularly agriculturally significant animals or companion animals (e.g., cows, sheep, goats, horses, swine, dogs, cats, rabbits, birds, poultry, fish, etc.), laboratory animals (e.g., mice, rats) primates, or humans.

Sublethal: A "sublethal" concentration of an antibiotic refers to a concentration that is less than the MIC of the antibiotic. In certain embodiments of the invention a sublethal concentration is not sufficient to significantly reduce the growth rate (proliferation) of a microbial cell, e.g., the growth rate is reduced by less than 20%, preferably less than 10%. Such a concentration is referred to herein as a "non-inhibiting concentration". A "lethal" concentration of an antibiotic is one that is equal to or greater than the MIC and would ultimately result in microbial death and complete or essentially complete sterilization of a culture medium containing the microbe if continued indefinitely assuming that no resistant strains arise during the incubation period.

Substituted: As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O—(CH$_2$)$_{0-4}$C(O)OR°); —(CH$_2$)$_{0-4}$CH(OR°)$_2$; —(CH$_2$)$_{0-4}$SR°; —(CH$_2$)$_{0-4}$ Ph, which may be substituted with R°; —(CH$_2$)$_{0-4}$O(CH$_2$)$_{0-1}$ Ph which may be substituted with R°; —CH=CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°S(O)$_2$NR°$_2$; —N(R°S(O)$_2$R°; —N(OR°)R°; —C(NH)NR°$_2$; —P(O)$_2$R°; —P(O)R°$_2$; —OP(O)R°$_2$; —OP(O)(OR°$_2$; SiR°$_3$; —(C$_{1-4}$ straight or branched)alkylene)O—N(R°$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R■, -(haloR■), —(CH$_2$)$_{0-2}$OH, —(CH$_2$)$_{0-2}$OR■, —(CH$_2$)$_{0-2}$ CH(OR■)$_2$; —O(haloR■), —CN, —N$_3$, —(CH$_2$)$_{0-2}$ C(O)R■, —(CH$_2$)$_{0-2}$C(O)OH, —(CH$_2$)$_{0-2}$C(O)OR■, —(CH$_2$)$_{0-2}$ SR■, —(CH$_2$)$_{0-2}$SH, —(CH$_2$)$_{0-2}$NH$_2$, —(CH$_2$)$_{0-2}$ NHR■, —(CH$_2$)$_{0-2}$NR■$_2$, —NO$_2$, —SiR■$_3$, —OSiR■$_3$, —C(O)SR■, —(C$_{1-4}$ straight or branched alkylene)C(O)OR■, or —SSR■ wherein each R■ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0–4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R■, -(haloR■), —OH, —OR■, —O(haloR■), —CN, —C(O)OH, —C(O)OR■, —NH$_2$, —NHR■, —NR■$_2$, or —NO$_2$, wherein each R■ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R■, -(haloR■), —OH, —OR■, —O(haloR■), —CN, —C(O)OH, —C(O)OR■, —NH$_2$, —NHR■, —NR■$_2$, or —NO$_2$, wherein each R■ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Survival: The term "survival", as used herein, refers to an ability of microbial cells to grow in the presence of one or more antibiotic agent(s) present above the relevant minimum inhibitory concentration. In some embodiments, survival is assessed at a concentration that is at or above a multiple of MIC (e.g., 2×, 4×, 5×, 6×, 8×, 10×, etc)

Treatment: As used herein, the term "treatment" refers to the provision of any type of medical or surgical management to a subject. Treatment can include, but is not limited to, administering a pharmaceutical composition to a subject. Treatment is typically undertaken in an effort to alter the course of a disease, disorder, or undesirable condition in a manner beneficial to the subject. The effect of treatment can generally include reversing, alleviating, reducing severity of, delaying the onset of, inhibiting the progression of, and/or reducing the likelihood of occurrence or reoccurence of the disease, disorder, or condition to which such term applies, or one or more symptoms or manifestations of such disease, disorder or condition. A composition of this invention can be administered to a subject who has developed an infection or is at increased risk of developing an infection relative to a member of the general population. A composition of this invention can be administered prophylactically, i.e., before development of any symptom or manifestation of a condition. Typically in this case the subject will be at risk of developing the condition. For example, an inventive composition can be administered prior to exposure of the subject to an infectious agent or prior to the occurrence of a pathogenic event.

Unit Dosage Form: A "unit dosage form", as that term is used herein, refers to physically discrete units suited as unitary dosages for the subject to be treated; each unit containing a predetermined quantity of active agent(s) calculated to produce the desired therapeutic effect in association with the required pharmaceutical carrier Unsaturated: The term "unsaturated", as used herein, means that a moiety has one or more units of unsaturation.

DETAILED DESCRIPTION OF CERTAIN PREFERRED EMBODIMENTS

In certain preferred embodiments, the present invention provides RecA inhibitors, compositions containing them, systems for identifying or characterizing them, and methods of using them. In some embodiments, RecA inhibitors interact directly with RecA. For example, a RecA inhibitor may bind to RecA, inhibitors bind to RecA (e.g., to one or more binding sites). Each of these preferred embodiments, and others, is discussed in more detail below.

I—Rec A

The RecA protein is a key sensor and activator in response to DNA damage and plays a major role in inducing the SOS response pathway following such damage. It is known that RecA is also involved in other cellular processes in addition to recombination and DNA damage repair.

One fundamental event in both homologous recombination and SOS response induction is the formation of a RecA-ssDNA-ATP nucleoprotein filament. In this conformation, RecA acts as both a recombinase and co-protease. In the latter function, it activates the SOS response by cleaving the LexA repressor protein, which results in the induction of genes that are repressed by LexA under normal conditions. Over 30 SOS genes, and UmuD, a sub-unit of polymerase IV, also involved in the SOS response, are induced (Courcelle and Hanawalt, Annu Rev Genet., 2003, 37: 611-646; Sutton et al., Annu Rev Genet. 2000, 34: 479).

Another fundamental role of RecA is to maintain the integrity of the genetic material. The binding of RecA to single-stranded DNA regions that block replication forks serves as the sensor that replication is blocked and maintains the integrity of the replication fork itself until replication can resume (Courcelle and Hanawalt, Annu Rev Genet., 2003, 37: 611-646).

The RecA protein is highly conserved and is cross species functional. For example, recA homologs from *Yersinia pestis, Bacillus anthracis* and *M. tuberculosis* have been shown to complement the *E. coli*_recA− mutation (Suchkov and Mishan'kin, Mol Gen Mikrobiol Virusol., 1989 5: 34; Ko et al., J Bacteriol., 2002, 184: 3917; Nair and Steyn, J Gen Microbiol., 1991, 137: 2409). Thus, at least some inhibitors of RecA identified using the RecA protein from one species would be expected to show activity in a wide variety of bacteria.

The RecA protein has many functional features that present points of intervention to inhibit its activity in accordance with the present invention. Multiple alignment of the sequence reveals a canonical structure of RecA-like proteins consisting of distinct segments or motifs (FIG. 1). These segments or modules are highly conserved and have been assigned functional roles based on genetic, biochemical and structural studies. Such modules are involved in DNA damage recognition and binding, monomer interaction, filament formation, helicase motifs, ATP binding and hydrolysis, recombination, replication and co-protease activity. Mutational studies have identified residues that are critical to these processes.

For example, the Gly157 change generates a constitutive co-protease form of RecA and results in a lower survival in response to UV treatment, a phenotype itself associated to a low recombination competent form of RecA. The present invention makes use of this information to precisely map regions of RecA to be targeted for compound discovery, e.g., using computational approaches (see below).

For example, RecX (also called OraA) is an inhibitor of RecA for both recombinase and co-protease activities (Stohl et al., J. Biol. Chem., 2003, 278: 2278,). RecX appears to inhibit the ATPase activity of RecA. Genetic and biochemical evidence identifies sites of interaction between RecA and LexA, suggesting that amino acids at positions 67, 154-157, 229 and 243 are responsible at least in part for the binding to LexA (VanLook et al., 2003, J Mol Biol., 333: 345). Also, amino acid changes at positions 122-123 and 150-161 dramatically decrease the ability of mutant cells to survive in response to UV radiation treatment. A domain in RecA that likely forms part of the co-protease substrate binding site has also been identified (Nastri et al., Mol Microbiol., 1997, 25: 967).

According to the invention, this information may be used to select portions of RecA for computational screening against small molecule libraries, and/or to identify likely binding sites or activities of inventive RecA inhibitors. Moreover, the present invention defines two novel inhibitor binding sites on the RecA protein, and demonstrates (as discussed in more detail below) that inhibitors interacting with this site have uniquely useful antibiotic, potentiating, and/or resistance suppressing activities.

II—Inhibitors of Rec A

In general, agents that inhibit one or more activities of RecA, and/or that inhibit RecA expression levels, may be useful in accordance with the present invention. Exemplary RecA activities that may be inhibited include, but are not limited to, DNA binding, monomer interaction, helicase activity, filament formation, ATP binding and/or hydrolysis, co-protease activity (e.g., toward LexA and/or UmuD), recombinase activity, replication function, and combinations thereof. In some embodiments, inventive RecA inhibitors inhibit one or more such activities with an $IC_{50}$ below about 100 µg/ml, 50 µg/ml, 15 µg/ml; 10 µg/ml; 5 µg/ml, 3 µg/ml, or 1 µg/ml. According to the present invention, desirable RecA ATPase inhibitors may even have an $IC_{50}$ well below 1 µg/ml, or even below 500 ng/ml, 100 ng/ml, 50 ng/ml, 30 ng/ml, 25 ng/ml, 20 ng/ml, 15 ng/ml, 10 ng/ml, 5 ng/ml, 1 ng/ml, or less.

In some embodiments of the present invention, RecA inhibitors are broad spectrum antibiotics in that they inhibit RecA (or the relevant RecA homolog) from more than one different microbial source. In other embodiments, RecA inhibitors have a narrow spectrum activity in that they inhibit one or more activities of RecA (or its relevant homolog) from a specific family of organisms or from a specific organism. In certain preferred embodiments, RecA inhibitors inhibit one or more activities of RecA (or its relevant homolog) from a disease-causing organism (in particular an organism that causes disease in a mammal, e.g., a human). In some embodiments, however, the RecA inhibitors (which may be broad spectrum with regard to microbes) do not inhibit RecA (or the relevant RecA homolog) from one or more higher organisms (e.g., mammals, humans). For example, in some embodiments, RecA inhibitors do not inhibit RAD51.

In some embodiments, the present invention provides RecA inhibitors that inhibit the RecA ATPase activity. For example, the present invention demonstrates that a variety of compounds inhibit RecA ATPase activity in an in vitro luciferase assay (see, for example, Example 10). The present invention specifically provides the compounds depicted in FIGS. 2A and 2B as RecA inhibitors with the indicated $IC_{50}$s in the in vitro luciferase assay.

In some embodiments of the present invention, RecA inhibitors that inhibit the RecA ATPase activity do not inhibit certain other cellular ATPases.

In some embodiments, the present invention provides RecA inhibitors that bind directly to RecA. In some embodiments, RecA inhibitors bind to the RecA ATP binding site. However, in some embodiments, inventive RecA inhibitors do not bind to the RecA ATP binding site (even though they may inhibit the RecA ATPase activity). In certain embodiments, inventive RecA inhibitors bind to two or more different sites on the RecA protein. For example, Example 20 proposes two potential new binding sites for RecA inhibitors, including those that inhibit ATPase activity.

In some embodiments, inventive RecA inhibitors that bind directly to RecA bind to a site comprised of amino acid residues including R85, F270, Y271, K310, and/or R324 (see, for example, Example 20). According to the present invention, this site can be found on the outer surface of RecA, as positioned in a filament. According to the present invention, hinokiflavone may bind to this RecA site. Further according to the present invention, compounds that compete with hinokiflavone for binding to RecA may be desirable RecA inhibitors. As used herein, the term "competes with hinokiflavone for binding to RecA", when used to characterize a compound, refers to a compound that has binding properties to RecA similar to (i.e., similar binding site(s) than) hinokiflavone.

Certain RecA inhibitors have been found to potentiate the activity of one or more antibiotic agents (see PCT application filed on the same date as the present application). For example, hinokiflavone has been found to potentiate activity of a quinolone antibiotic (ciprofloxacin) (see, for example, Example 15), a potentiation that was only observed against cells that express RecA (see, for example, Example 17).

Certain RecA inhibitors have been found to reduce the incidence of resistance that develops to one or more antibiotic agents (see PCT application filed on the same date as the present application). For example, hinokiflavone was found to reduce the incidence of resistance to ciprofloxacin (see, for example, Example 19).

RecA inhibitors of the present invention show intrinsic antibiotic activity, even in the absence of any other antibiotic agent. The present Applicants have shown that RecA is (1) a virulence factor and (2) a stand alone target (see Example 22). For example, given that deletion of RecA dramatically reduces the ability of bacterial strains to establish and/or continue an infection in rats (see, for example, Example 8) or mice (see, for example, Example 9), according to the present invention, at least some RecA inhibitors should achieve similar results. Indeed, the present Applicants have demonstrated that hinokiflavone can reduce strain survival in vitro, even for strains that are somewhat resistant to other antibiotic agents (see, for example, Example 15). The identification of RecA inhibitors with antibiotic (i.e., killing) activity against microbial cells, and especially against resistant cells, is one particularly advantageous contribution of the present invention.

In other embodiments, RecA inhibitors can actually protect cells from death. Without wishing to be bound by any particular theory, it is noted that one possible explanation for the present findings is that RecA inhibitors effective for use as antibiotic agents or potentiating agents according to the present invention are those that can simultaneously bind to two distinct sites on RecA, for example to the ATP binding site and to another binding site, including for example one of the sites identified in Example 20. Alternatively or additionally, it may be the case that, although many agents can inhibit the RecA ATPase, most such agents also inhibit other ATPases within a cell, causing a variety of stresses and inducing protective mechanisms (e.g., shut down of DNA replication) that allow the cells to avoid the effects of antibiotic agents.

In some embodiments of the present invention, RecA inhibitors are small molecule agents, typically having some cyclic character (e.g., including one or more aryl rings). Certain RecA inhibitors according to the present invention are flavones; certain RecA inhibitors according to the present invention are bisflavones. In some embodiments of the invention, the RecA inhibitor is or includes hinokiflavone.

In some embodiments of the present invention, RecA inhibitors are small molecule compounds that have the structure of formula I:

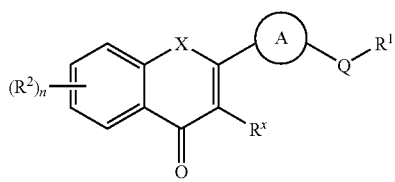

I or a pharmaceutically acceptable salt or derivative thereof, wherein:

X is oxygen, sulfur, or N(R);

n is 0 to 4;

$R^1$ is hydrogen, or an optionally substituted group selected from a $C_{1-6}$ aliphatic group, a monocyclic 3-8 membered saturated, partially unsaturated, or aryl ring having 0-4 heteroatoms independently selected from nitrogen, oxygen, or sulfur, or a bicyclic 8-10 membered saturated, partially unsaturated, or aryl ring having 0-5 heteroatoms independently selected from nitrogen, oxygen, or sulfur;

each $R^2$ is independently halogen, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, $SO_2N(R^3)_2$;

each $R^3$ is independently hydrogen or an optionally substituted group selected from a $C_{1-6}$ aliphatic group, a monocyclic 3-8 membered saturated, partially unsaturated, or aryl ring having 0-4 heteroatoms independently selected from nitrogen, oxygen, or sulfur, or a bicyclic 8-10 membered saturated, partially unsaturated, or aryl ring having 0-5 heteroatoms independently selected from nitrogen, oxygen, or sulfur;

Q is a valence bond or a bivalent, saturated or unsaturated, straight or branched $C_{1-6}$ hydrocarbon chain, wherein 0-2 methylene units of Q are independently replaced by —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—;

each R is independently hydrogen or an optionally substituted aliphatic group;

$R^x$ is R or OR; and

Ring A is an optionally substituted 3-8 membered bivalent, saturated, partially unsaturated, or aryl monocyclic ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

As defined generally above, the X group of formula I is oxygen, sulfur, or N(R). In certain embodiments, the X group of formula I is oxygen. Accordingly, the present invention provides RecA inhibitors of formula I-a:

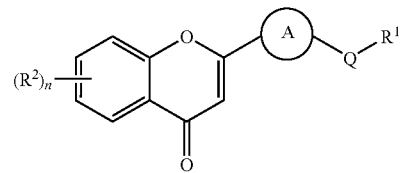

I-a or a pharmaceutically acceptable salt or derivative thereof, wherein each of Ring A, Q, n, $R^1$, and $R^2$ are as defined above and described herein.

As defined generally above, the $R^1$ group of formula I is hydrogen, or an optionally substituted group selected from a $C_{1-6}$ aliphatic group, a monocyclic 3-8 membered saturated, partially unsaturated, or aryl ring having 0-4 heteroatoms independently selected from nitrogen, oxygen, or sulfur, or a bicyclic 8-10 membered saturated, partially unsaturated, or aryl ring having 0-5 heteroatoms independently selected from nitrogen, oxygen, or sulfur.

In certain embodiments, the $R^1$ group of formula I is a bicyclic 8-10 membered saturated, partially unsaturated, or aryl bicyclic ring having 0-5 heteroatoms independently selected from nitrogen, oxygen, or sulfur. In still other embodiments, $R^1$ is a bicyclic 10 membered partially unsaturated ring having one oxygen atom optionally substituted with 1 to 3 substituents independently selected from halogen, —(CH$_2$)$_{0-4}$R°, —(CH$_2$)$_{0-4}$OR°, —(CH$_2$)$_{0-4}$SR°, —(CH$_2$)$_{0-4}$Ph, optionally substituted with R° or OR°, —(CH$_2$)$_{0-4}$O(CH$_2$)$_{0-1}$Ph optionally substituted with R° or OR°, —CH═CHPh, optionally substituted with R° or OR°, —(CH$_2$)$_{0-4}$N(R°$_2$, wherein each R° may be substituted as defined herein and is independently hydrogen, $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. According to one embodiment, $R^1$ is substituted with 1 to 3 groups independently selected from OH and OMe.

According to one embodiment of the invention, the $R^1$ group of formula I is selected from:

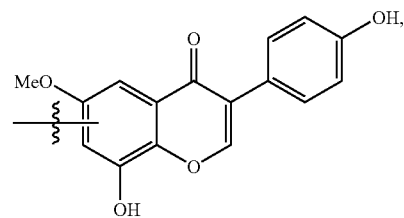

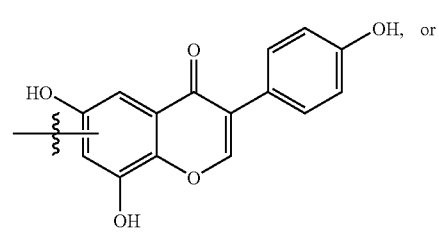

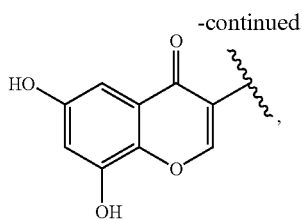

wherein each wavy line depicts the point of attachment to Q.

In certain embodiments, the $R^1$ group of formula I is a monocyclic 3-8 membered saturated, partially unsaturated, or aryl ring having 0-4 heteroatoms independently selected from nitrogen, oxygen, or sulfur. In other embodiments, the $R^1$ group of formula I is a monocyclic 5-6 membered aryl ring having 0-2 nitrogen atoms, wherein $R^1$ is optionally substituted with 1 to 3 substituents independently selected from halogen, —$(CH_2)_{0-4}R°$, —$(CH_2)_{0-4}OR°$, —$(CH_2)_{0-4}SR°$, —$(CH_2)_{0-4}Ph$, optionally substituted with $R°$ or $OR°$, —$(CH_2)_{0-4}O(CH_2)_{0-1}Ph$ optionally substituted with $R°$ or $OR°$, —CH=CHPh, optionally substituted with $R°$ or $OR°$, —$(CH_2)_{0-4}N(R°_2)$, wherein each $R°$ may be substituted as defined herein and is independently hydrogen, $C_{1-6}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. According to one embodiment of the present invention, $R^1$ is phenyl substituted with 1 to 3 groups independently selected from halogen, —$(CH_2)_{0-4}R°$, and —$(CH_2)_{0-4}OR°$. Such groups include chloro, fluoro, OH, OMe, methyl, ethyl, propyl, cyclopropyl, isopropyl, and the like. In some embodiments, OH or OMe groups are present.

According to another embodiment, the $R^1$ group of formula I is selected from:

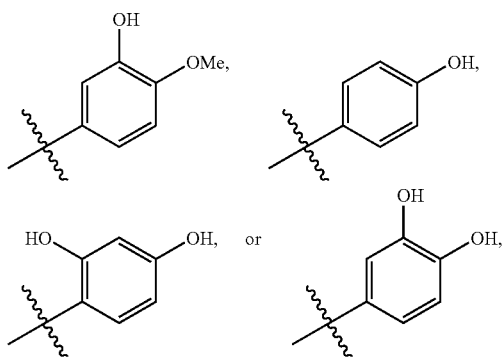

wherein each wavy line indicates the point of attachment to Q.

As defined generally above, the Q group of formula I is a valence bond or a bivalent, saturated or unsaturated, straight or branched $C_{1-6}$ hydrocarbon chain, wherein 0-2 methylene units of Q are independently replaced by —O—, —NR—, —S—, —OC(O)—, —C(O)O—, —C(O)—, —SO—, —$SO_2$—, —$NRSO_2$—, —$SO_2NR$—, —NRC(O)—, —C(O)NR—, —OC(O)NR—, or —NRC(O)O—. In certain embodiments, Q is a valence bond such that $R^1$ is directly attached to Ring A. In other embodiments, Q is a bivalent, saturated, and straight $C_{1-3}$ hydrocarbon chain, wherein 0-1 methylene units of Q is replaced by —O—, —NR—, —S—, —OC(O)—, —C(O)O—, —C(O)—, —SO—, —$SO_2$—, —$NRSO_2$—, —$SO_2NR$—, —NRC(O)—, —C(O)NR—, —OC(O)NR—, or —NRC(O)O—. In still other embodiments, Q is —O—, —NR—, —S—, —OC(O)—, —C(O)O—, —C(O)—, —SO—, —$SO_2$—, —$NRSO_2$—, —$SO_2NR$—, —NRC(O)—, —C(O)NR—, —OC(O)NR—, or —NRC(O)O—. According to another embodiment, Q is —O—.

As defined generally above, the Ring A group of formula I is an optionally substituted 3-8 membered bivalent, saturated, partially unsaturated, or aryl monocyclic ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In certain embodiments, Ring A is an optionally substituted 3-8 membered bivalent, saturated, partially unsaturated, or aryl monocyclic ring having 0-4 heteroatoms independently selected from nitrogen, oxygen, or sulfur. In other embodiments, Ring A is an optionally substituted 5-6 membered bivalent aryl ring having 0-2 nitrogen atoms. In still other embodiments, Ring A is phenylene optionally substituted with 1 to 4 groups independently selected from halogen, —$(CH_2)_{0-4}R°$, —$(CH_2)_{0-4}OR°$, —$(CH_2)_{0-4}SR°$, —$(CH_2)_{0-4}Ph$, optionally substituted with $R°$ or $OR°$, —$(CH_2)_{0-4}O(CH_2)_{0-1}Ph$ optionally substituted with $R°$ or $OR°$, —CH=CHPh, optionally substituted with $R°$ or $OR°$, —$(CH_2)_{0-4}N(R°_2)$, wherein each $R°$ may be substituted as defined herein and is independently hydrogen, $C_{1-6}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. According to another embodiment, Ring A is phenylene optionally substituted with 1-2 groups independently selected from halogen, —$(CH_2)_{0-4}R°$, and —$(CH_2)_{0-4}OR°$. Such groups include chloro, fluoro, OH, OMe, methyl, ethyl, propyl, cyclopropyl, isopropyl, and the like. In some embodiments, OH and/or OMe group(s) are present.

As defined generally above, each $R^2$ group of formula I is independently halogen, $R^3$, $OR^3$, $SR^3$, $N(R^3)_2$, $C(O)R^3$, $C(O)OR^3$, $NR^3C(O)R^3$, $C(O)NR^3$, $SO_2R^3$, $NR^3SO_2R^3$, $SO_2N(R^3)_2$, wherein each $R^3$ is independently hydrogen or an optionally substituted group selected from a $C_{1-6}$ aliphatic group, a monocyclic 3-8 membered saturated, partially unsaturated, or aryl ring having 0-4 heteroatoms independently selected from nitrogen, oxygen, or sulfur, or a bicyclic 8-10 membered saturated, partially unsaturated, or aryl ring having 0-5 heteroatoms independently selected from nitrogen, oxygen, or sulfur. In certain embodiments, each $R^2$ group is independently halogen, $R^3$, $OR^3$, $SR^3$, or $N(R^3)_2$, wherein each $R^3$ is as defined above. According to one embodiment, at least one $R^2$ group is OH. According to another embodiment, one $R^2$ group is $R^3$ wherein $R^3$ is an optionally substituted bicyclic 8-10 membered saturated, partially unsaturated, or aryl ring having 0-5 heteroatoms independently selected from nitrogen, oxygen, or sulfur. In still other embodiments, one $R^2$ group is $R^3$ wherein $R^3$ is a bicyclic 10 membered partially unsaturated ring having one oxygen atom optionally substituted with 1 to 3 substituents independently selected from halogen, —$(CH_2)_{0-4}R°$, —$(CH_2)_{0-4}OR°$, —$(CH_2)_{0-4}SR°$, —$(CH_2)_{0-4}Ph$, optionally substituted with $R°$ or $OR°$, —$(CH_2)_{0-4}O(CH_2)_{0-1}Ph$ optionally substituted with $R°$ or $OR°$, —CH=CHPh, optionally substituted with $R°$ or $OR°$, —$(CH_2)_{0-4}N(R°_2)$, wherein each $R°$ may be substituted as defined herein and is independently hydrogen, $C_{1-6}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

According to one embodiments, $R^3$ is substituted with 1 to 3 groups independently selected from OH and OMe and optionally substituted phenyl.

According to some embodiments of the invention, the $R^2$ group formula I is OH, OMe, or is selected from:

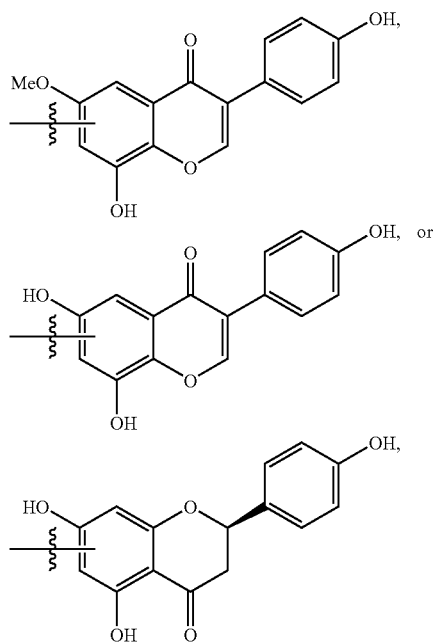

wherein each wavy line depicts the point of attachment to the phenyl group of formula I.

Figure 2A:
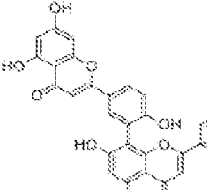
Figure 2A:
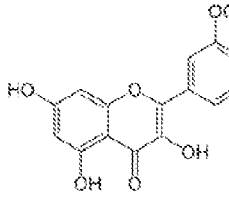
Figure 2A:
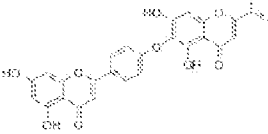
Figure 2A:
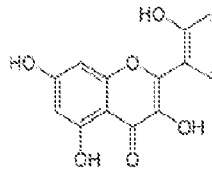
Figure 2A:
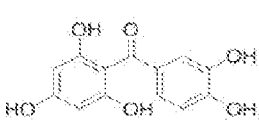
Figure 2A:
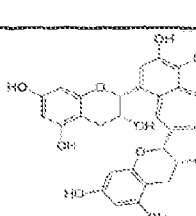
Figure 2A:
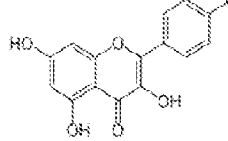
Figure 3:
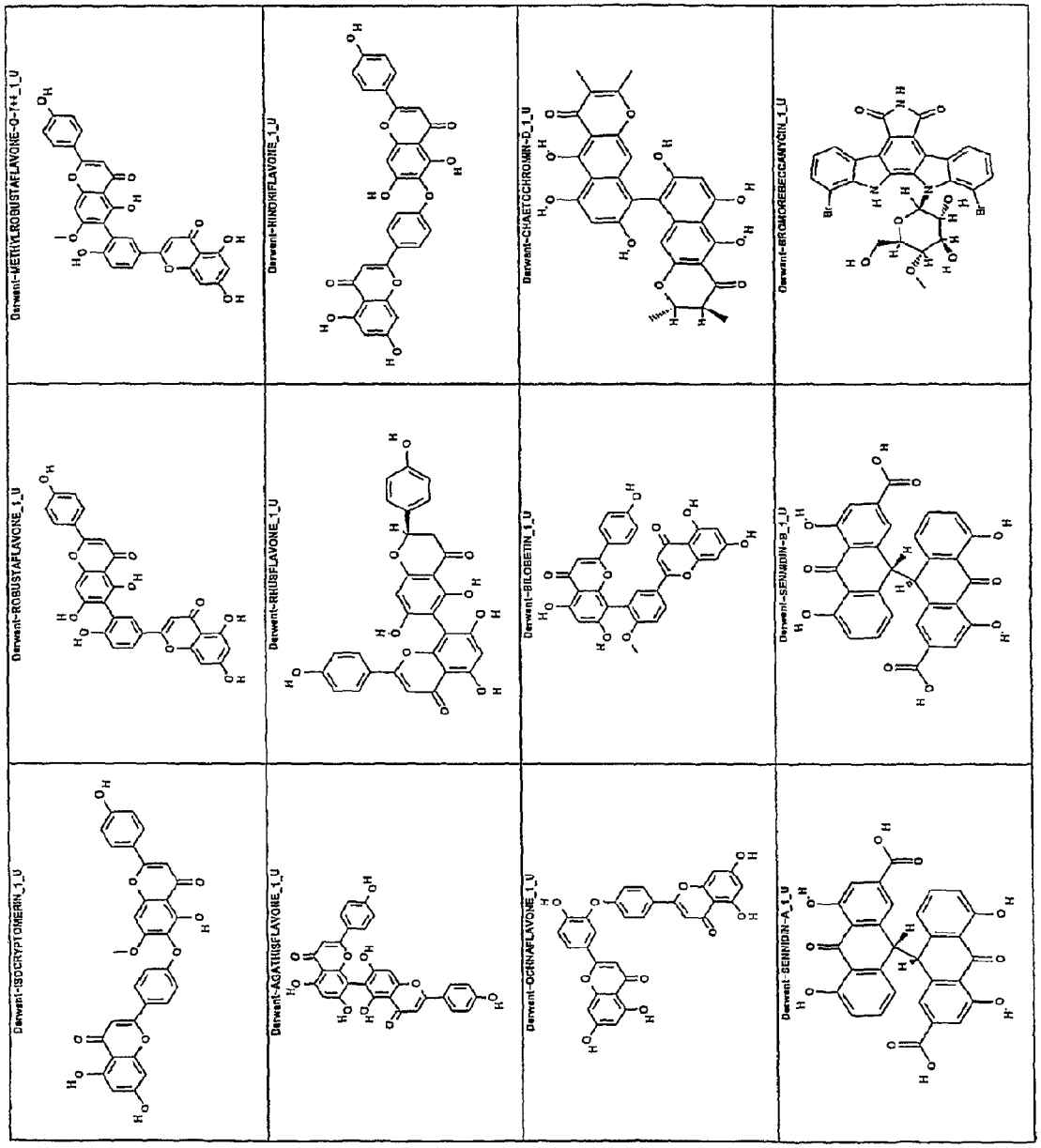
FIG. 3 presents chemical structures of potential RecA inhibitors that are structurally related to hinokiflavone.

Exemplary compounds of formula I are set forth in FIGS. 2A, 2B and 3.

The present invention specifically identifies hinokiflavone as a particularly desirable RecA inhibitor within the scope of formula I. The present invention also encompasses the recognition that compounds that share structural (see, for example, FIG. 3) and/or energetic (see, for example, FIGS. 4A and 4B) features of hinokiflavone may be useful as RecA inhibitors as described herein. Thus, according to the present invention, compounds having the structures set forth in FIG. 3 or 4A or 4B and/or having the structure of formula II may be useful as RecA inhibitors as described herein:

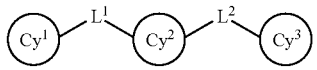

or a pharmaceutically acceptable salt or derivative thereof, wherein:
Cy$^1$ is a an optionally substituted 5-6 membered aryl ring having 0-3 heteroatoms independently selected from nitrogen, oxygen, or sulfur;
L$^1$ is a valence bond, a C$_{1-6}$ bivalent saturated, unsaturated, straight or branched hydrocarbon chain, —N(R)—, —N(R)SO$_2$—, —N(R)SO$_2$N(R)—, —N(R)C(O)—, —C(O)N(R)—, or —N(R)C(O)N(R)—;
each R is independently hydrogen or an optionally substituted C$_{1-6}$ aliphatic group;
Cy$^2$ is an optionally substituted 6-membered aryl ring having 0-2 nitrogen atoms, an 8-10 membered bicyclic heteroaryl ring having 1-3 heteroatoms independently selected from nitrogen, oxygen, or sulfur, or an optionally substituted 5-membered heteroaryl ring having 1-2 heteroatoms independently selected from nitrogen, oxygen, or sulfur;
L$^2$ is a C$_{1-6}$ bivalent saturated, unsaturated, straight or branched hydrocarbon chain, —CH$_2$CH$_2$C(=W)N(R)N(R)C(=W)—, —N(R)C(=W)N(R)C(=W)C(R)$_2$W—, —C(=W)N(R)N(R)C(=W)N(R)—, —C(=W)N(R)N(R)C(=W)N(R)CH=CH$_2$, or —C(=W)N(R)C(=W)N(R)—, wherein each W is independently oxygen or sulfur; and
Cy$^3$ is an optionally substituted 6-membered aryl ring having 0-2 nitrogen atoms.

It should be understood that, unless otherwise stated, chemical structures or formulae depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of depicted structures or formulae are within the scope of the invention. Unless otherwise stated, all tautomeric forms of the structures or formulae of the invention are within the scope of the invention. Additionally, unless otherwise stated, structures depicted herein are also meant to include compounds that differ only in the presence of one or more isotopically enriched atoms. For example, compounds having the depicted structures or formulae except for the replacement of hydrogen by deuterium or tritium, or the replacement of a carbon by a $^{13}$C- or $^{14}$C-enriched carbon are within the scope of this invention. Such compounds may be useful, for example, as analytical tools or probes in biological assays.

It should further be understood that the present invention encompasses pharmaceutically acceptable derivatives, and in particular prodrugs, metabolites, and pharmaceutically acceptable salts of the depicted compounds.

III—Antibiotic Agents

As discussed herein, inventive RecA inhibitors may be used alone or they may be utilized in combination with one or more antibiotic agents.

Exemplary structural classes of antibiotics for use in combination with RecA inhibitors according to the present invention include, but are not limited to, aminoglycosides, aminomethylcyclines, amphenicols, ansamycins, β-lactams (e.g., penicillins or cephalosporins), carbapenems, dapsones, 2,4-diaminopyrimidines, glycopeptides, glycycyclines, ketolides, lincomycins, lincosamides, macrolides, nitrofurans, oxazolidinones, peptides, polymyxins, quinolones, rifabutins, streptogramins, sulfonamides, sulfones, tetracyclines, and combinations thereof.

Exemplary mechanistic classes of antibiotics for use in combination with RecA inhibitors according to the present invention include, but are not limited to, those that inhibit protein synthesis, cell wall synthesis, DNA replication, transcription, and/or cell division. It will be appreciated that biological and biochemical pathways are not mutually exclusive and that some biological or biochemical pathways may be considered to be subsets or sub-pathways of other biological or biochemical pathways. Mechanisms of action more specifically include, but are not limited to, inhibiting protein synthesis (e.g., by binding ribosomal RNA or proteins, blocking tRNA binding to ribosome-mRNA complex, inhibiting peptidyl transferase), inhibiting or interfering with synthesis of a cell wall component (e.g., inhibition of peptidoglycan synthesis, disruption of peptidoglycan cross-linkage, disruption of movement of peptidoglycan precursors, disruption of mycolic acid or arabinoglycan synthesis), cell membrane disruption, inhibiting or interfering with nucleic acid synthesis or processing, acting as "antimetabolites" and either inhibiting an essential bacterial enzyme or competing with a substrate of an essential bacterial enzyme, inhibiting or interfering with cell division.

It is understood by those of ordinary skill in the art that antibiotic agents of a particular structural class typically (though not necessarily) fall within the same mechanistic class.

Examples of antibiotics that can be used in combination with a RecA inhibitor according to the present invention include, but are not limited to bacitracin; cephalosporins (such as cefadroxil, cefazolin, cephalexin, cephalothin, cephapirin, cephradine, cefaclor, cefamandole, cefonicid, ceforanide, cefoxitin, cefuroxime, cefoperazone, cefotaxime, cefotetan, ceftazidime, ceftizoxime, ceftriaxone, and meropenem); cycloserine; fosfomycin, penicillins (such as amdinocillin, ampicillin, amoxicillin, azlocillin, bacamipicillin, benzathine penicillin G, carbenicillin, cloxacillin, cyclacillin, dicloxacillin, methicillin, mezlocillin, nafcillin, oxacillin, penicillin G, penicillin V, piperacillin, and ticarcillin); ristocetin; vancomycin; colistin; novobiocin; polymyxins (such as colistin, colistimathate, and polymyxin B); aminoglycosides (such as amikacin, gentamicin, kanamycin, neomycin, netilmicin, paromomycin, spectinomycin, streptomycin, and tobramycin), tetracyclines (such as demeclocycline, doxycycline, methacycline, minocycline, and oxytetracycline); carbapenems (such as imipenem); monobactams (such as aztreonam); chloramphenicol; clindamycin; cycloheximide; fucidin; lincomycin; puromycin; rifampicin; other streptomycins; macrolides (such as erythromycin and oleandomycin); fluoroquinolones; actinomycin; ethambutol; 5-fluorocytosine; griseofulvin; rifamycins; sulfonamides (such as sulfacytine, sulfadiazine, sulfisoxazole, sulfamethoxazole, sulfamethizole, and sulfapyridine); and trimethoprim. Other antibacterial agents include, but are not limited to, bismuth containing compounds (such as bismuth aluminate, bismuth subcitrate, bismuth subgalate, and bismuth subsalicylate); nitrofurans (such as nitrofurazone, nitrofurantoin, and furozolidone); metronidazole; tinidazole; nimorazole; and benzoic acid.

In certain embodiments, RecA inhibitors are used in combination with a quinolone antibiotic. Quinolone antibiotics are compounds that contain a quinolone or a naphthyridine nucleus with any of a variety of different side chains and substituents. Numerous modifications of the originally identified core structures have been made resulting in a large number of compounds with activity against differing groups of bacteria. Quinolone antibiotics are described, e.g., in Ronald and Low (Eds.), "Fluoroquinolone Antibiotics", Birkhäuser Verlag, Basel, 2003; DaSilva et al., Curr. Med. Chem., 2003, 10: 21; Van Bambeke et al., Clin Microbiol. Infect., 2005, 11: 256; U.S. Pat. Nos. 3,669,965; 4,563,459; 4,620,007; 4,382,892; 4,985,557 5,053,407; and 5,142,046).

Figure 5:
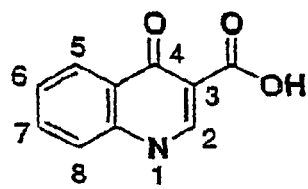
FIG. 5 depicts the core structures and numbering system of classical quinolone antibiotics (4-quinolone and 4-naphthyridine systems).
Figure 5:
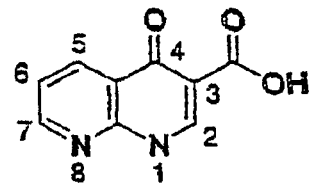

FIG. 5 depicts the core structures and numbering system of classical quinolone antibiotics (4-quinolone and 4-naphthyridine systems). It is noted that the numbering system shown herein is used for purposes of convenience and is not intended to be limiting. The invention encompasses quinolone compounds in which an alternative numbering system is used.

Exemplary quinolone antibiotics include, but are not limited to, any of the antibacterial agents disclosed in the foregoing references including, but not limited to, ciprofloxacin, oxolinic acid, cinoxacin, flumequine, miloxacin, rosoxacin, pipemidic acid, norfloxacin, enoxacin, moxifloxacin, gatifloxacin, ofloxacin, lomefloxacin, temafloxacin, fleroxacin, pefloxacin, amifloxacin, sparfloxacin, levofloxacin, clinafloxacin, nalidixic acid, enoxacin, grepafloxacin, levofloxacin, lomefloxacin norfloxacin, ofloxacin, trovafloxacin, olamufloxacin, cadrofloxacin, alatrofloxacin, gatifloxacin, rufloxacin, irloxacin, prulifloxacin, pazufloxacin, gemifloxacin, sitafloxacin, tosulfloxacin, amifloxacin, nitrosoxacin-A, DX-619, and ABT-492. Quinolone antibiotics include fluoroquinolones (e.g., having a fluorine substituent at the C-6 position), and non-fluoroquinolones. Also included within the scope of quinolone antibiotics are derivatives in which a quinolone is conjugated with, e.g., covalently bound to, another core structure. For example, U.S. Pub. No. 2004-0215017 discloses compounds in which an oxazolidinone, isoxazolinone, or isoxazoline is covalently bonded to a quinolone.

Figure 6:
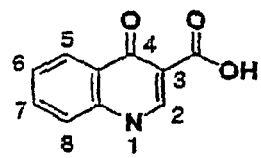
FIG. 6 illustrates core structures of quinolone antibiotics related to the 4-oxo-1,4-dihydroquinoline and 4-oxo-1,4 dihydronapthyridine systems FIG. 7, Panels A and B depict particular core structures of certain quinolone antibiotics.
Figure 6:
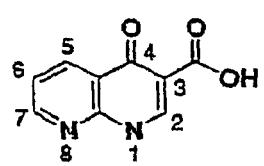
Figure 6:
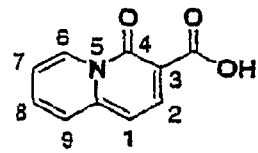
Figure 6:
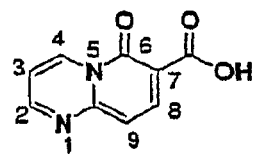
Figure 7A:
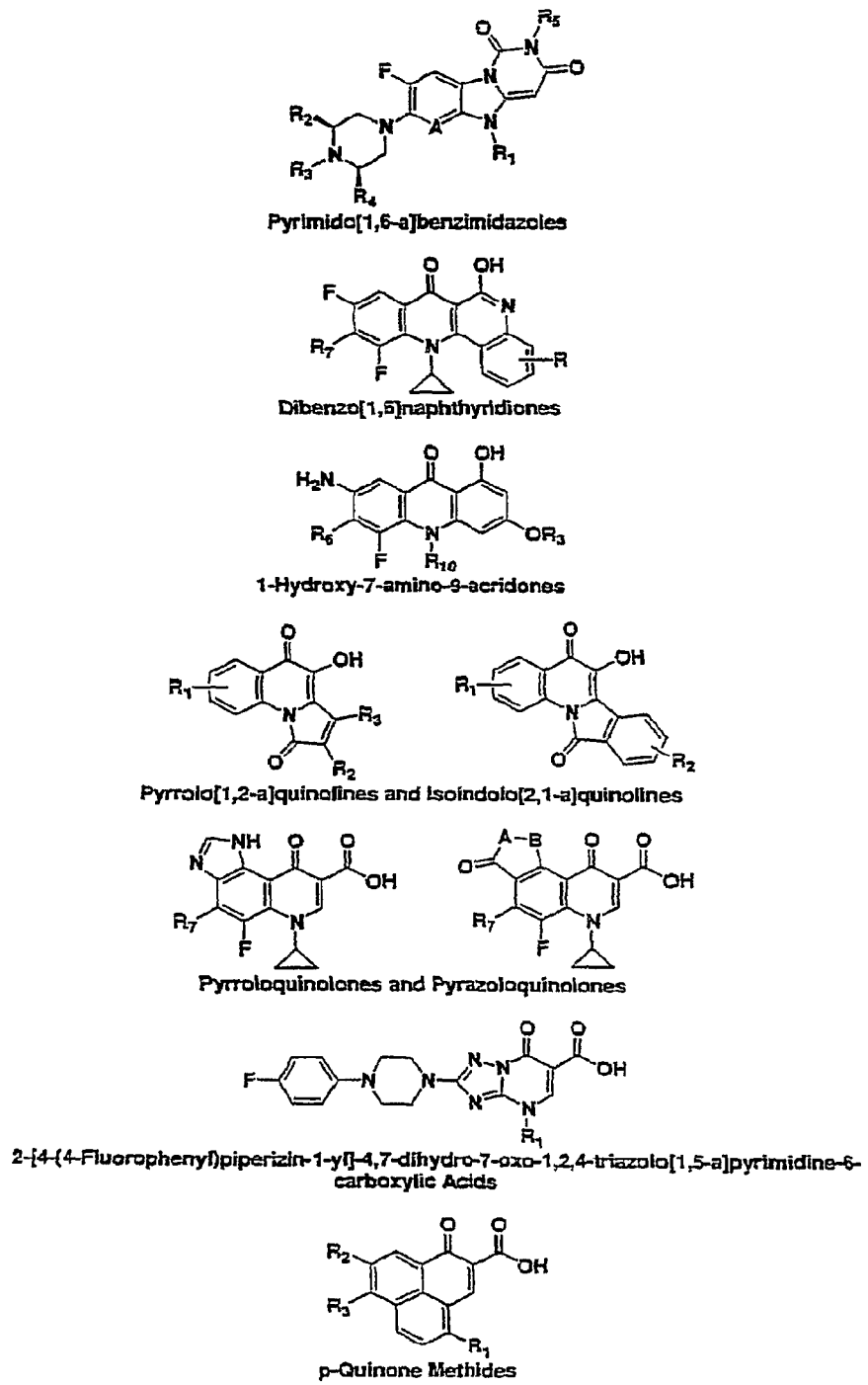
Figure 7B:
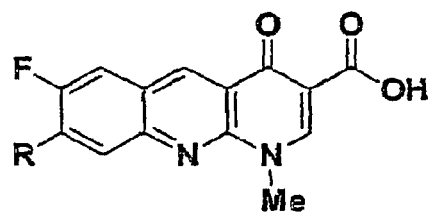
Figure 7B:
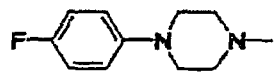
Figure 7B:
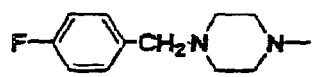
Figure 7B:
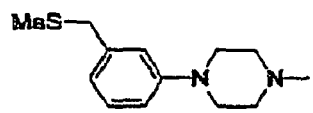
Figure 7B:
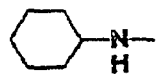
Figure 7B:

Included within the scope of quinolone antibiotics that can be utilized in accordance with the present invention are compounds that have a core structure related to the 4-oxo-1,4-dihydroquinoline and 4-oxo-1,4 dihydronapthyridine systems, e.g., 2-pyridones, 2-naphthyridinones, and benzo[b] naphthyridones. 2-pyridones are potent inhibitors of bacterial type II topoisomerases (Saiki et al., Antimicrob. Agents Chemother., 1999, 43: 1574). The core structures are depicted in FIG. 6. Also included within the scope of quinolone antibiotics are compounds that have core structures related to the quinolone core structures depicted in FIG. 5 or 6. Certain of these core structures are shown in FIG. 7A or 7B and references thereto are provided in Ronald and Low (Eds.), "Fluoroquinolone Antibiotics", Birkhäuser Verlag, Basel, 2003; DaSilva et al., Curr. Med. Chem., 2003, 10: 21.

IV—Pharmaceutical Compositions and Kits

The present invention provides pharmaceutical compositions comprising an effective amount of one or more inventive RecA inhibitors. In some embodiments, the pharmaceutical compositions further comprise one or more antibiotic agents other than the inventive RecA inhibitors.

Suitable preparations, e.g., substantially pure preparations, of inventive RecA inhibitors and/or antibiotic agents may be combined with pharmaceutically acceptable carriers or excipients, etc., to produce an appropriate pharmaceutical composition. The invention therefore provides a variety of pharmaceutically acceptable compositions for administration to a subject comprising (i) an inventive RecA inhibitor; and (ii) a pharmaceutically acceptable carrier or excipient. The invention further provides a pharmaceutically acceptable composition comprising (i) an inventive RecA inhibitor; (ii) an antibiotic agent; and (iii) a pharmaceutically acceptable carrier or excipient. The invention also provides a pharmaceutically acceptable unit dosage form containing a predetermined amount of an inventive RecA inhibitor, optionally further including a predetermined amount of an antibiotic agent.

Pharmaceutical compositions of the present invention may be provided as immediate release formulations or as sustained release formulations. A variety of strategies are known in the art for achieving sustained release, e.g., by prolonging residence time in the stomach (such as through the use of swellable polymers), providing pH or enzyme-sensitive coatings, employing bioadhesive coatings that stick to the walls of the stomach or intestine, etc. See, e.g., U.S. Pub. No. 2004-0024018 and references therein.

Furthermore, inventive pharmaceutical compositions may be formulated for any desirable route of delivery including, but not limited to, intravenous, intramuscular, by inhalation (e.g., as an aerosol), by catheter, intraocularly, oral, rectal, intradermal, by application to the skin, etc.

It is to be understood that the pharmaceutical compositions of the invention, when administered to a subject, are preferably administered for a time and in an amount sufficient to treat the disease or condition for which they are administered, e.g., a bacterial infection.

In certain embodiments of the pharmaceutical compositions of the invention, one or more of the inventive RecA inhibitors and/or antibiotic agents is provided in the form of a pharmaceutically acceptable derivative (e.g., a prodrug), by which is meant any non-toxic salt, ester, salt of an ester or other derivative of a agent of this invention that, upon administration to a recipient, directly or indirectly provides the relevant RecA inhibitor or antibiotic agent, or an inhibitorily active metabolite or residue thereof. As used herein, the term "inhibitorily active metabolite or residue thereof" means that a metabolite or residue thereof exhibits inhibitory activity towards a protein (e.g., RecA) or microorganism, as appropriate.

As is understood in the art, pharmaceutically acceptable carriers or excipients generally refer to non-toxic components that are appropriate for administration to a subject and that do not destroy the pharmacological activity of the RecA inhibitor(s) and/or antibiotic agent(s) with which they are combined. Appropriate pharmaceutically acceptable carriers or excipients are known in the art and include, for example, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Solvents, dispersion media, coatings, isotonic and absorption delaying agents, and the like, compatible with pharmaceutical administration may be included. Supplementary active agents, e.g., agents independently active against the disease or clinical condition to be treated, or agents that enhance availability and/or activity of an inventive RecA inhibitor or an antibiotic agent, can also be incorporated into the compositions.

Pharmaceutically acceptable salts of inventive RecA inhibitors and/or antibiotic agents include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the inventive RecA inhibitors or antibiotic agents and their pharmaceutically acceptable acid addition salts.

Salts derived from appropriate bases include alkali metal (e.g., sodium and potassium), alkaline earth metal (e.g., magnesium), ammonium and NNo(C1-4 alkyl)4 salts. This invention also envisions the quaternization of any basic nitrogen-containing groups of the compounds disclosed herein. Water or oil-soluble or dispersible products may be obtained by such quaternization.

A pharmaceutical composition is formulated to be compatible with its intended route of administration. Solutions or suspensions used for parenteral (e.g., intravenous), intramuscular, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. Such parenteral preparations can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), phosphate buffered saline (PBS), or Ringer's solution.

Sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

It is generally desirable that pharmaceutical compositions, particularly for injection, be sterile, if possible, and should be fluid to the extent that easy syringability exists.

Pharmaceutical formulations are desirably stable under the conditions of manufacture and storage and should be preserved against the contaminating action of microorganisms such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. A desired fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of injectable compositions can be brought about by including in the composition an agent which delays absorption, for example, aluminum monostearate and gelatin. Prolonged absorption of oral compositions can be achieved by various means including encapsulation.

Sterile injectable solutions can be prepared by incorporating the active agent(s) (i.e., inventive RecA inhibitor(s) and/or antibiotic agent(s)) in a required amount in an appropriate solvent with one or a combination of ingredients enumerated above, as required, followed by filtered sterilization. Preferably solutions for injection are free of endotoxin. Generally, dispersions are prepared by incorporating the active agent(s) into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active agent(s) can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, inventive compositions may desirably be delivered in the form of an aerosol spray from a pressured container or dispenser which contains a suitable propellant, e.g., a gas such as carbon dioxide, or a nebulizer. Liquid or dry aerosol (e.g., dry powders, large porous particles, etc.) can be used. The present invention also contemplates delivery of compositions using a nasal spray. Pharmaceutical compositions to be administered by nasal aerosol or inhalation may be prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

For topical applications, inventive pharmaceutical compositions may be formulated in a suitable ointment containing the active component suspended or dissolved in one or more carriers. Carriers for topical administration of the agents of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For local delivery to the eye, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Inventive pharmaceutical compositions may be formulated for transmucosal or transdermal delivery. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active agents are formulated into ointments, salves, gels, or creams as generally known in the art.

Inventive pharmaceutical compositions may be formulated as suppositories (e.g., with conventional suppository bases such as cocoa butter and other glycerides) or as retention enemas for rectal delivery.

In some embodiments, inventive pharmaceutical compositions include one or more agents intended to protect the active agent(s) against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polyethers, and polylactic acid. Methods for preparation of such formulations will be apparent to those skilled in the art. Certain of the materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811 and other references listed herein. Liposomes, including targeted liposomes (e.g., antibody targeted liposomes) and pegylated liposomes have been described (C. B. Hansen et al., Biochim. Biophys. Acta, 1995, 1239: 133-144; V. P. Torchilin et cd., Biochim. Biophys. Acta, 2001, 1511: 397-411; T. Ishida et al., FEBS Lett., 1999, 460: 129-133).

It is often desirable to formulate pharmaceutical compositions, particularly those for oral or parenteral compositions, in unit dosage form for ease of administration and uniformity of dosage. Unit dosage form, as that term is used herein, refers to physically discrete units suited as unitary dosages for the subject to be treated; each unit containing a predetermined quantity of active agent(s) calculated to produce the desired therapeutic effect in association with the required pharmaceutical carrier.

In general, pharmaceutical compositions are formulated to contain an amount of active agent(s) (i.e., inventive RecA inhibitors and/or antibiotic agents) sufficient to achieve a desired biological or pharmacological effect while minimizing any associated toxicity. Toxicity and therapeutic efficacy of active agents can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents which exhibit high therapeutic indices are preferred. While agents that exhibit toxic side effects can be used, care should be taken to design a delivery system that targets such agents to the site of affected tissue in order to minimize potential damage to uninfected cells and, thereby, reduce side effects.

The data obtained from cell culture assays and animal studies can be used in formulating a range of dosage for use in humans. The dosage of such agents lies preferably within a range of circulating concentrations that include the $ED_{50}$ with little or no toxicity. The dosage can vary within this range depending upon the dosage form employed and the route of administration utilized. For any agent used in accordance with the present invention, the therapeutically effective amount (e.g., the amount that is therapeutically effective to achieve a desired degree of antibiotic activity) can typically be estimated initially from cell culture assays. However, it is generally more desirable to establish dosing based on studies in animal models, where amounts required to achieve a circulating plasma concentration range that includes the $IC_{50}$ (e.g., the concentration of the test agent which achieves a half-maximal inhibition of symptoms, half-maximal inhibition of growth or survival of an infectious agent, etc.) can be determined. Such information can be used to more accurately determine useful doses in humans. Levels in plasma can be measured, for example, by high performance liquid chromatography.

A therapeutically effective amount of an active agent in a pharmaceutical composition typically ranges from about 0.001 to about 100 mg/kg body weight, about 0.01 to about 25 mg/kg body weight, about 0.1 to about 20 mg/kg body weight, about 1 to about 10 mg/kg, about 2 to about 9 mg/kg, about 3 to about 8 mg/kg, about 4 to about 7 mg/kg, or about 5 to about 6 mg/kg body weight. Other exemplary doses include, for example, about 1 µg/kg to about 500 mg/kg, about 100 µg/kg to about 5 mg/, about 1 µg/kg to about 50 µg/kg). In general, smaller doses are typically required for local administration as contrasted with systemic administration. Furthermore, it is understood by those of ordinary skill in the art that appropriate doses in any particular circumstance depend upon the potency of the agent(s) utilized, and may optionally be tailored to the particular recipient, for example, through administration of increasing doses until a preselected desired response is achieved. It is particularly understood that the specific dose level for any particular subject may depend upon a variety of factors including the activity of the specific agent(s) employed, the age, body weight, general health, gender, and diet of the subject, the time of administration, the route of administration, the rate of excretion, etc.

Inventive pharmaceutical compositions may be administered according to any desired schedule, typically selected to achieve optimal therapeutic effect. For instance, inventive pharmaceutical compositions can be administered at various intervals and over different periods of time as required, e.g., multiple times per day, daily, every other day, once a week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous treatments, the general health and/or age of the subject, and other diseases present. Generally, treatment of a subject with an inventive composition can include a single treatment or, in many cases, can include a series of treatments. It will be appreciated that a range of different dosage combinations (e.g., doses of inventive RecA inhibitor and/or antibiotic agent) can be used.

The present invention also provides pharmaceutical packs or kits comprising one or more containers (e.g., vials, ampoules, test tubes, flasks, or bottles) containing one or more ingredients of the inventive pharmaceutical compositions, for example, allowing for the simultaneous or sequential administration of the RecA inhibitors and antibiotic agent(s). Optionally associated with such container(s) can be a notice in the form prescribed by a governmental agency regulating the manufacture, use or sale of pharmaceutical products, which notice reflects approval by the agency of manufacture, use or sale for human administration. Different ingredients may be supplied in solid (e.g., lyophilized) or liquid form. Each ingredient will generally be suitable as aliquoted in its respective container or provided in a concentrated form. Kits may also include media for the reconstitution of lyophilized ingredients. The individual containers of the kit are preferably maintained in close confinement for commercial sale.

IV—Use of Rec A Inhibitors

In general, according to the present invention, inhibition of RecA has several important effects on cells. First, cells in which RecA is inhibited have a reduced ability to repair damage to their DNA, and also have a reduced ability to infect a host. Thus, inhibition of RecA reduces pathogen virulence.

In particular, cells (e.g., those of an infectious organism) in which RecA is inhibited are particularly susceptible to the oxidative burst that occurs within phagocytes. Thus, when microbial organisms and/or pathogens are ingested by phagocytes, they are exposed to a variety of lethal factors, including oxidative radicals, acidic pH, and destructive enzymes. Oxidative radicals in particular cause DNA damage. Cells with reduced RecA activity have reduced ability to recover from such DNA damage and therefore succumb more readily to phagocytotic attack.

Furthermore, many types of microbial infections are initiated by the adherence of pathogens to host tissues. This process requires interaction of microbial surface proteins called adhesions with proteins, such as fibronectin, on the surface of host cells. RecA has been shown to participate in the fibronectin-binding pathway in some bacteria (e.g., *S. aureus*; Bisognano et al., J. Biol. Chem., 2004, 279: 9064). Thus, inhibition of RecA can also reduce virulence by reducing adhesion of microbial cells to host cells.

Thus, the present invention provides RecA inhibitors that are useful in the treatment of microbial infection. Such RecA inhibitors may be utilized alone (i.e., in the absence of any other antibiotic agent) to treat infection, or alternatively may be utilized together with one or more other antibiotic agents. In certain embodiments, the combination of an antibiotic agent with a RecA inhibitor for the treatment of microbial infection allows the antibiotic agent to be used at a dose below its convention dose, and/or on a less frequent dosing schedule. This can be advantageously used to reduce drug toxicity observed with certain antibiotic agents.

Inventive RecA inhibitors are useful to inhibit growth of a wide variety of microbial types including, for example, gram negative bacteria, gram positive bacteria and/or acid fast bacteria. Particular examples of bacteria whose growth or proliferation can be inhibited include, but are not limited to, members of the following genuses: *Actinomyces, Staphylococcus, Streptococcus, Enterococcus, Erysipelothrix, Neisseria, Branhamella, Listeria, Bacillus, Corynbacterium, Erysipelothrix, Gardnerella, Mycobacterium, Nocardia, Enterobacteriaceae, Escherichia, Salmonella, Shigella, Yersinia, Enterobacter, Klebsiella, Citrobacter, Serratia, Providencia, Proteus, Morganella, Edwardsiella, Erwinia, Vibrio, Aeromonas, Helicobacter, Campylobacter, Eikenella, Pasteurella, Pseudomonas, Burkholderia, Stenotrophomonas, Acinetobacter, Ralstonia, Alcaligenes, Moraxella, Mycoplasma, Legionella, Francisella, Brucella, Haemophilus, Bordetella,*

*Clostridium, Bacteroides, Porphyromonas, Prevotella, Fusobacterium, Borrelia, Chlamydia, Rickettsia, Ehrlichia, Bartonella, Trichomonas, Treponema*, and combinations thereof (i.e., infections established by more than one bacterial strain).

In particular embodiments of the invention the bacteria are species that are causative agents of disease in humans and/or animals. Examples include, but are not limited to, *Aeromonas hydrophila, Bacillus subtilis, Escherichia coli, Enterobacter cloacae, Campylobacter jejuni, Haemophilus influenzae, Klebsiella pneumoniae, Klebsiella oxytoca, Legionella pneumophila, Pasteurella multocida, Proteus mirabilis, Proteus vulgaris, Morganella morganii, Helicobacter pylori, Neisseria gonorrhoeae, Pseudomonas aeruginosa, Salmonella enterica, Salmonella typhimurium, Staphylococcus aureus, Staphylococcus epidermidis, Streptococcus pneumoniae, Streptococcus pyogenes, Streptococcus agalactiae*, and combinations thereof.

In certain embodiments of the invention, the bacterial species or strain is one that is sensitive to a particular antibiotic agent or class of antibiotic agents.

In certain embodiments of the invention, the bacterial species or strain is one that is resistant to a particular antibiotic agent or class of antibiotic agents.

Inventive RecA inhibitors and compositions containing them can be used to inhibit microbial growth and/or survival in a variety of contexts. For example, they may be employed to inhibit growth and/or survival of organisms maintained in cell culture or inhabiting locations in the environment, e.g., inert surfaces, clothing, towels, bedding, utensils, etc. Of particular interest are fomites, i.e., inanimate objects that may be contaminated with disease-causing microorganisms and may serve to transmit disease to a human or animal. Such locations or objects can be contacted with a solution containing an inventive RecA inhibitor, and optionally including one or more other antibiotic agents. Inventive RecA inhibitors, alone or together with one or more other antibiotic agents, can be added to food or water, particularly for the prevention of microbial disease in animals.

An inventive RecA inhibitor may be administered alone or in combination with another antibiotic agent, may be administered to a subject in need thereof, e.g., a human or animal suffering from or at risk of a bacterial infection. When administered in combination, the inventive RecA inhibitor and antibiotic, may be components of a single pharmaceutical composition or may be administered as individual pharmaceutical compositions. They may be administered using the same route of administration or different routes of administration. In certain embodiments of the invention a unit dosage form containing a predetermined amount of a RecA inhibitor and optionally a predetermined amount of another antibiotic agent is administered. It will be appreciated by those of ordinary skill in the art that the predetermined about of RecA inhibitor may be different, even for the same RecA inhibitor, if it is being administered alone or in combination. In certain embodiments, the RecA inhibitor and the one or more additional antibiotic agent(s) are administered concomitantly. In other embodiments, the RecA inhibitor and the antibiotic agent(s) are administered sequentially. For example, in certain preferred embodiments, the RecA inhibitor is administered prior to administration of the antibiotic agent(s).

A therapeutic regimen that includes a RecA inhibitor and another antibiotic agent may (i) allow the use of a reduced daily dose of the antibiotic without significantly reducing efficacy; (ii) allow the use of a shorter course of administration of the antibiotic without significantly reducing efficacy; or both.

Infections and infection-related conditions that can be treated using an inventive RecA inhibitor (and optionally another antibiotic agent) include, but are not limited to, pneumonia, meningitis, sepsis, septic shock, sinusitis, otitis media, mastoiditis, conjunctivitis, keratitis, external otitis (e.g., necrotizing otitis externa and perichondritis), laryngeal infections (e.g., acute epiglottitis, croup and tuberculous laryngitis), endocarditis, infections of prosthetic valves, abscesses, peritonitis, infectious diarrheal diseases, bacterial food poisoning, sexually transmitted diseases and related conditions, urinary tract infections, pyelonephritis, infectious arthritis, osteomyelitis, infections of prosthetic joints, skin and soft tissue infections, oral infections, dental infections, nocardiosis and actinomycosis, mastitis, brucellosis, Q fever, anthrax, wound infections, etc.

In certain embodiments of the invention, a RecA inhibitor, optionally together with another antibiotic agent, is used to treat or prevent infection associated with an indwelling device. Indwelling devices include surgical implants, prosthetic devices, and catheters, i.e., devices that are introduced to the body of an individual and remain in position for an extended time. Such devices include, for example, artificial joints, heart valves, pacemakers, defibrillators, vascular grafts, vascular catheters, cerebrospinal fluid shunts, urinary catheters, continuous ambulatory peritoneal dialysis (CAPD) catheters, spinal rods, implantable pumps for medication delivery, etc. Inventive RecA inhibitors (and other antibiotic agents) can be applied to, coated on, imbedded in, or otherwise combined with an indwelling device to prophylactically treat (e.g., delay the onset of, reduce the severity of, or prevent entirely) infections. Alternatively or additionally, a RecA inhibitor (optionally together with another antibiotic agent) of the invention may be administered to a subject to achieve a systemic effect shortly before, or concomitantly with, insertion of an indwelling device. Of course, local delivery of a RecA inhibitor and/or antibiotic may also be employed. Furthermore, any RecA inhibitor and antibiotic agent may be delivered separately (e.g., by different routes and/or at different times). Treatment with inventive RecA inhibitor and/or another antibiotic agent may be continued after implantation of the device, during all or part of the time during which the device remains in the body, and, optionally, thereafter. Alternatively or additionally, inventive RecA inhibitors (and other antibiotic agents) can be used to bathe an indwelling device immediately before insertion and/or to bathe wounds or sites of insertion. Exemplary concentrations useful for these purposes typically range between about 1 µg/ml and 10 µg/ml.

RecA inhibitors (and other antibiotic agents) of this invention may be used before, during, or after dental treatment or surgery.

Any of a variety of methods may be employed to identify a subject in need of treatment (e.g., a subject at risk of or suffering from a microbial infection) according to the present invention. For example, such methods include clinical diagnosis based at least in part on symptoms, imaging studies, immunodiagnostic assays, nucleic acid based diagnostics, and/or isolation and culture of potentially causative microorganisms from samples, such as blood, urine, sputum, synovial fluid, cerebrospinal fluid, pus, or any sample of body fluid or tissue.

Inventive methods can include a step of identifying a subject suffering from or at risk of a microbial infection, a step of identifying a microorganism suspected of causing the infection, a step of selecting a therapeutic regimen based at least in part on the identity or suspected identity of the microorganism and/or the location or characteristics of the infection. In certain embodiments of the invention, the method includes determining that a subject has a significant likelihood (e.g., at least 5%) of suffering from or being at risk of infection by a microorganism that is resistant to one or more antibiotics.

A subject is "at risk of" an infection in any of a variety of circumstances. "At risk of" implies at increased risk of, relative to the risk such subject would have in the absence of one or more circumstances, conditions, or attributes of that subject, and/or (in the case of humans) relative to the risk that an average, healthy member of the population would have. Specific examples of conditions that place a subject "at risk" include, but are not limited to, immunodeficiencies (particularly those affecting the humoral or non-specific (innate) immune system); prior treatment with antibiotic agent(s) that may have reduced or eliminated normal microbial flora; treatment with agent(s) that suppress the immune system (e.g., cancer chemotherapy, immunosuppressive agents); chronic diseases such as diabetes or cystic fibrosis; surgery or other trauma; infancy or old age; occupations, events, or living conditions that entail exposure to pathogenic microorganisms; etc.

While it is anticipated that inventive RecA inhibitors will find particular use for inhibiting the growth and/or survival of microorganisms, they may also be used for other purposes. For example, although many embodiments of the invention utilize RecA inhibitors that do not inhibit activities of higher organism homologs (e.g., RAD51), in some embodiments of the invention, it may be desirable to utilize inventive RecA inhibitors that do act against homologs in higher organisms. For example, such RecA inhibitors are useful specifically in order to treat disorders, diseases or defects associated with activity of such higher organism homologs, and/or to potentiate or reduce resistance to other agents being used to treat a relevant disorder, disease, or defect. Indeed, in some embodiments of the invention, it may be desirable to utilize RAD51 inhibitors that do not also inhibit RecA.

To give but one particular example, inventive RecA inhibitors that inhibit RAD51 and/or other mammalian topoisomerases may be useful in the treatment of any of a variety of cancers, either alone or in combination with one or more other anti-cancer agents. In some embodiments, the inventive RecA inhibitors are utilized in an amount effective to have anti-cancer activity, to potentiate anti-cancer activity of another agent, to reduce resistance to another agent, or combinations thereof. For instance, other agents that could be used in combination with inventive RecA inhibitors in the treatment of cancer include, but are not limited to alkylating agents, topoisomerase I inhibitors, topoisomerase II inhibitors, RNA/DNA antimetabolites, DNA antimetabolites, antimitotic agents, natural antineoplastic agents, hormonal antineoplastic agents, angiogenesis inhibitors, differentiating agents, gene therapy agents, biological response modifiers, anti-metastatic agents, and combinations thereof.

In some embodiments of the invention, RecA inhibitors are used to treat cancer in subjects receiving radiation therapy.

EXAMPLES

Example 1

RecA Activity Assay—Luciferase ATPase Assay

RecA is a DNA-dependent ATPase (i.e., it catalyzes the reaction adenosine triphosphate [ATP]→adenosine diphosphate [ADP]). An assay was developed for RecA ATPase activity based on detection of the amount of ATP remaining in a reaction mixture following incubation of RecA protein, DNA, and ATP. In the assay, *E. coli* RecA protein is incubated in reaction buffer with DNA, ATP, and any test compound or compounds for a measured amount of time. The quantity of ATP remaining after the RecA reaction is quantitated using a subsequent luciferase assay. The amount of ATP remaining can be compared to controls containing either a known inhibitor (full inhibition control) or no test compound (full activity control).

Materials

Kinase glo, Adenosine triphosphate, Adenosine 5'-O-(3-thiotriphosphate) plus and 384 well plates were obtained from Fisher, M13mp18 Single-stranded DNA, RecA protein, and T4 polynucleotide kinase reaction buffer (70 mM Tris-HCl pH7.5; 10 mM $MgCl_2$; 5 mM DTT) were obtained from New England Biolabs.

Methods

Final reaction mixture contains: 0.5 μl of M13 single stranded DNA (250 μg/ml); 1.0 μl of 10×PHK buffer; 0.25 μl of RecA (2 mg/ml); 0.25 μl of 1 mM ATP; 0.25 μl of test compound in DMSO; and 12.0 μl of $H_2O$.

Test compounds are incubated at room temperature in the presence of RecA protein and DNA prior to addition of ATP. This can be achieved by the preparation of two mixes, as indicated below. Desirably, both a no-DNA and a DNA/DMSO-only (i.e., no test compound) control were included.

| Component | Mix 1 (in μl) | ATP Mix (in μl) |
|---|---|---|
| M13 | 0.5 | 0.0 |
| 10X PNK Buffer | 1.0 | 0.25 |
| RecA | 0.25 | 0.0 |
| 1 mM ATP | 0.0 | 0.25 |
| 1 mM ATP-G or Test compound | 0.5 | 0.0 |
| $H_2O$ | 7.75 | 2.0 |
| Total each | 10 | 2.5 |

The following steps are then performed: (1) Add 7.75 μl of mix 1 to the well of a 384 well plate; (2) Add 0.5 μl of the compound of interest; (3) Incubate at room temperature for 5 minutes; (4) Add 2.5 μl of the ATP mix. Incubate at room temperature for 30 minutes; (5) Add 12.5 μl of Promega Kinase glo plus; (6) Incubate at room temp for 10 minutes or more; and (7) Measure luminescence of the reaction.

Example 2

RecA Activity Assay—DNA Binding Assay

This assay measures RecA DNA binding activity, and can be used to identify or characterize RecA inhibitors according to the present invention.

The plasmid pUC19 contains 5 HpyCH4 IV sites, including one at position 374. A 60 mer oligonucleotide was designed having complementarity to the region in pUC19 that centers around the HpyCH4 IV site at position 374. The following reaction components were combined in 40 μL RecA Reaction Buffer: 1 μg of pUC19; 0.18 μg of 60 mer; 0.3 mM ATP γ-S; and 4 μg of RecA, and were incubated at 37° C. for 10 minutes, so that a stable triple helix was formed. Unprotected sites were methylated using 8 units of SSS I supplemented with 160 μM SAM for 10 minutes at 37° C. The reaction was stopped and the triple helix was disrupted by incubation at 65° C. for 15 minutes. The reaction was cooled and 10 units of HpyCH4 IV were added. Digestion was allowed to proceed at 37° C. for 20 minutes. Greater than 90% of the product was single cut pUC19. Thus, this assay can be used to identify and/or characterize RecA inhibitors because, if they interfere with RecA DNA binding, then they will ultimately reduce the amount of single cut product observed.

Example 3

RecA Activity Assay—Cell-Based Reporter Assay for Expression and/or Activity This assay utilizes a low copy number reporter plasmid in which the recA promoter controls transcription of the mRNA encoding green fluorescence protein (GFP). This plasmid, which is known as prec::GFP and has been previously described (see, for example, Ronen et al., Proc. Natl. Acad. Sci USA, 2002, 99: 10555), contains 2821707-2821893 of the *E. coli* MG1655 genome (numbering based on the sequenced genome as reported in Blattner et al., Science, 1997, 277: 153) clones upstream of a promoterless GFPmut3 gene in a low copy pSC101 origin plasmid (see Kalir et al., Science, 2001, 292: 2080).

Cells are grown, typically to early log phase in rich medium with shaking. Various amounts of antibiotic agent and/or test agent are added at a given time point, and 60 minutes later, fluorescence due to GFP expression from the reporter plasmid is measured using a spectrophotometer. Compounds that inhibit expression from the RecA promoter or that inhibit one or more RecA activities including, for example, DNA binding (including to its own promoter), monomer interaction, helicase activity, filament formation, ATP binding and/or hydrolysis, co-protease activity (e.g., toward LexA and/or UmuD), recombinase activity, replication function, and combinations thereof, decrease fluorescence in this assay.

Example 4

RecA Activity Assay—Biochemical Co-Protease Assay

In this assay, which is based on an assay developed by Dutreix et al., J. Bacteriol., 1989, 171: 2415), the LexA coding sequence will be fused to a HIS tag (Qiagen), and expressed from the pQE vector under control of the T5 promoter. This vector allows for expression of C-terminally 6×His-tagged proteins. The lexA ORF will be created by introducing an NcoI restriction site at the ATG codon of the insert by PCR. Identity of the insert will be confirmed by DNA sequencing. A test expression experiment will be performed and the integrity of the LexA protein will be checked using an anti-HIS antibody as described in the Qiagen kit. The QIAexpress detection reagents include high-affinity, high-specificity monoclonal Anti-His antibodies and antibody conjugates, and Ni-NTA conjugates.

The pQE-lexA plasmid will be transformed into a recA+ and recA− strains to test the assay genetically. In a recA+ background, LexA protein is expected to be seen intact unless DNA damage is induced, e.g., by exposure to an appropriate antibiotic agent (e.g., a quinolone). If DNA damage is induced, either a cleaved (shorter) LexA or no LexA protein is expected to be observed. LexA protein can be detected using a Western blot assay. In a recA− background, LexA is expected to be seen intact, whether or not DNA damage is induced.

Once the assay is validated, it can be used to assess the ability of RecA inhibitors to interfere with the RecA co-protease activity. It is expected that addition of RecA inhibitors, prior to or during DNA damage (i.e., exposure to quinolone antibiotic agent), will decrease the amount of LexA degradation, and will increase the amount of full-length LexA.

Typically, assay reactions will be performed so that 50 µg/ml of test compound is utilized in the presence of 300 ng/ml of Cipro. This amount of Cipro is enough to induce the RecA response but is not enough to kill the cells.

Typically, 2 ml of *E. coli* cells containing pQE-lexA will be grown to an $OD_{600}$ of 0.5, then exposed to Cipro or to Cipro+ test compound for 30-60 minutes. The cells will be harvested and disrupted; the protein extract will be applied on to the Ni-NTA conjugate column, aliquots will be run onto a SDS-PAGE, and LexA detection will be done using the anti-HIS antibodies. Compounds for which the LexA protein remains intact likely due to RecA inhibition will be further examined.

Example 5

Cell-Based Survival and Cell Growth Assays

Cell-Based Survival Assay.

This assay measures the number of cells that are able to form colonies (i.e., the number of colony forming units, CFU) after a culture has been treated with a particular antibiotic agent (e.g., norfloxacin or cipro). Typically, the antibiotic agent is applied to an early log phase culture at a concentration that is above the minimum inhibitory concentration ("MIC"; the minimum concentration that will inhibit growth) for the relevant strain under the relevant growth conditions. For example, the antibiotic agent may be applied at a level that is a multiple of the MIC, often 4× or 8×MIC. Samples of the cells are collected at various time points after addition of antibiotic agent (e.g., 0, 18, and 26 hours). The samples are washed and plated (e.g., in serial dilutions), typically on rich media, so that the number of CFU can be counted. CFU are then normalized to the time 0 time point, and can be plotted, for example, on a log graph.

Such a cell-based survival assay can be used to evaluate a test agent alone or in combination with another antibiotic agent. Often, a control assay is done with a known antibiotic agent, and in the absence of any test agent. Such a control assay can be compared with test agent alone and/or with known antibiotic+test agent.

Cell Growth Assay.

This assay measures the ability of cells to grow in the presence of a sublethal dose (i.e., a dose below the MIC) of an antibiotic agent (or test agent, or combination thereof). In general, cells are grown, typically to saturation, and are then diluted and inoculated onto rich medium and onto medium containing a sublethal dose of antibiotic agent. Plates are then grown overnight, and $OD_{600}$ is measured after overnight growth, as compared with blank plate. If desired, a test agent can be added to the plate, either alone or in combination with the known antibiotic agent, and the ratio of $OD_{600}$ in the presence of the test agent to $OD_{600}$ in the absence of the test agent, can be determined Additional ratios that can be useful as controls include, for example, $OD_{600}$ in the presence vs absence of antibiotic agent; $OD_{600}$ in the absence of any agent vs in the presence of both antibiotic agent and test agent; etc.

Example 6

Mutation/Resistance Assay

This assay measures the rate at which mutant cells arise in the presence of an antibiotic agent. Cells are grown in the presence of antibiotic agent at a concentration above (generally well above, e.g., 4× or 8×) its MIC, and further in the presence or absence of a test agent (that may inhibit or enhance mutation).

Every 24 hours, an aliquot is removed from the culture and is diluted so that the antibiotic agent is no longer present at a concentration above its MIC (e.g., so that the antibiotic agent is present at 0.5×MIC or less). These aliquoted samples are then assayed to determine whether they can grow in the presence of the antibiotic agent. Specifically, when growth is observed in the presence of antibiotic agent at a concentration that is 4×MIC, then resistance is said to have developed. Test compounds can therefore be assayed to assess whether or not they can reduce the incidence of resistance (e.g., by inhibiting mutation).

Example 7

In Vivo Assay of RecA Inhibitor Activity in Rats

An in vivo system has been developed for the identification and/or characterization of RecA inhibitors in rats. Specifically, the present Applicants have determined that infectious disease can be established in rats by intraperitoneal injection of an appropriate number of bacterial cells. They have further demonstrated that injection of the same number of otherwise identical cells lacking RecA (i.e., recA− mutant cells) does not establish infection. Furthermore, by isolating spleens from the infected rats and plating the colony forming units from within those spleens, they have established that recA− cells both (1) are avirulent; (2) and do not survive or grow in the animal.

For example, each of 7 rats were injected with one of the following agents in 200 μl PBS: no cells; $10^2$, $10^4$, or $10^6$ CFU *Staphylococcus aureus* RN4220 (RecA+); $10^2$, $10^4$, or $10^6$ CFU *Staphylococcus aureus* RN4220 recA−. On day 1, the rat that received $10^6$ CFU RN4220 (RecA+) was sick. On day 4, all rats were sacrificed and their spleens were recovered and processed. Cells were plated, and CFU present in the spleens were counted, with the following results:

| Pathogen | | CFU Recovered from Spleen |
|---|---|---|
| No cells | 0 cells | 0 |
| RecA+ cells | $10^2$ cells | 8 |
| | $10^4$ cells | 22 |
| | $10^6$ cells | 104 |
| recA− cells | $10^2$ cells | 1 |
| | $10^4$ cells | 0 |
| | $10^6$ cells | 1 |

These results demonstrate that inactivation of RecA in bacterial cells reduces their ability to cause sickness, and also reduces the number of CFU they can establish in rats. This system therefore can be used to identify and/or characterize inventive RecA inhibitors. The recA deletion strain can desirably be used as a positive control.

Example 9

In Vivo Assay of RecA Inhibitor Activity in Mice

This Example describes uses an in vivo system for the identification and/or characterization of RecA inhibitors in mice. Specifically, the present Applicants have determined that infectious disease can be established in mice, and indeed can kill the mice, by intraperitoneal injection of an appropriate number of bacterial cells. They have further demonstrated that all mice survive when the cells that are injected (same number of otherwise identical cells) lack RecA (i.e., are recA− mutant cells).

For example, each of 30 female CD-1 mice were injected with one of the following:>$5×10^7$ CFU *Staphylococcus aureus* grlA542 (RecA+); or >$5×10^7$ CFU *Staphylococcus aureus* grlA542recA$^{mut}$ (recA−) in 0.5 ml PBS (see Fournier et al., Antimicrob. Agents Chemother., 2000, 44: 2160). The number of dead animals was assessed at 24 hours and at 48 hours, with the following results:

| Pathogen | Number of Surviving Mice At 48 hours: |
|---|---|
| RecA+ cells | 1/15 (6.6%) |
| recA− cells | 15/15 (100%) |

These results indicate that loss of RecA function renders pathogens non-lethal in mice, and validate the inventive strategy of utilizing RecA inhibitors as antibiotic agents, even in the absence of any other antibiotic therapy.

Also, these results demonstrate that this system can be used to identify and/or characterize inventive RecA inhibitors (which, when administered prior to or during infection, should reduce lethality). The recA deletion strain can desirably be used as a positive control.

Example 10

In Vivo Assay of RecA Inhibitor Activity in Immunocompromised Mice

This Example describes an in vivo system for the identification and/or characterization of RecA inhibitors in immunocompromised mice. The experiment was similar to that described above in Example 9 except that, 4 days prior to infection, mice were rendered immunocompromised by treatment with 150 mg/kg cyclophosphamide in 0.5 ml sterile water. One day prior to infection, the mice were treated again with 100 mg/kg cyclophosphamide, again in 0. ml sterile water. Mice were then infected with RecA+ or recA− *S. aureus* as follows: $10^4$, $10^5$, or $10^6$ CFU *Staphylococcus aureus* grlA542 (RecA+); or $10^4$, $10^5$, or $10^6$ CFU *Staphylococcus aureus* grlA542recA$^{mut}$ (recA−) in 0.5 ml PBS (see Fournier et al., Antimicrob. Agents Chemother., 2000, 44: 2160). The number of dead animals was assessed at 24 hours, with the following results:

| Pathogen | | Number of Surviving Mice |
|---|---|---|
| RecA+ cells | $10^4$ cells | 2 of 5 |
| | $10^5$ cells | 1 of 5 |
| | $10^6$ cells | 0 of 5 |
| recA− cells | $10^4$ cells | 5 of 5 |
| | $10^5$ cells | 2 of 5 |
| | $10^6$ cells | 2 of 5 |

These results indicate that loss of RecA function dramatically reduces pathogenicity even in immunocompromised mice, and further validate the inventive strategy of utilizing RecA inhibitors as antibiotic agents, even in the absence of any other antibiotic therapy.

Also, these results demonstrate that this system can be used to identify and/or characterize inventive RecA inhibitors (which, when administered prior to or during infection, should reduce pathogenicity). The recA deletion strain can desirably be used as a positive control.

Example 11

Serum Binding Assay

The present Applicants have found that it can be desirable to assess the activity of RecA inhibitors in the presence of serum as an indicator of whether they are likely to retain activity when administered in vivo. Any one or more of the activity/characterization assays described herein can be performed so that a test agent/RecA inhibitor is exposed to serum for a period of time before or during assessment of its activity.

Example 12

Identification of RecA Inhibitors Using In Vitro Luciferase Assay

More than 2000 compounds were tested for their ability to inhibit RecA ATPase activity in the luciferase assay described in Example 1. Tested compounds were obtained from Boston University (1205 compounds from CMLD diversity library, available from Dr. Scott Schauss), IndoFine (66 compounds based on flavone structure), ChemdiV (48 compounds known to be ATPase inhibitors and 720 compounds structurally related to CB101 (described, for example, in U.S. Ser. No. 60/662,038), and Asinex. Five (5) tested compounds were bisflavones and 28 were predicted, based on structural modeling (see, for example, Example 20) to dock with Rec A. Many of the compounds are lipophilic, natural-product-like compounds. Others are flavones, bisflavones, flavonoids, coumarins, and/or heterocyclic compounds.

Of these compounds, 1 was found to have an $IC_{50}$ in this screen of below 100 μg/ml; 11 were found to have an $IC_{50}$ below 50 μg/ml; 9 were found to have an $IC_{50}$ below 15 μg/ml; 2 were found to have an $IC_{50}$ below 10 μg/ml; 5 were found to have an $IC_{50}$ below 5 μg/ml; 3 were found to have an $IC_{50}$ below 3 μg/ml; and 1 was found to have an $IC_{50}$ below 1 μg/ml. Structures of the 14 compounds that inhibited RecA ATPase activity by more than 50% are presented in FIGS. 2A and 2B. Percent inhibition is calculated according to the following equation:

$$\frac{(RLU \text{ in presence of compound}) - (RLU \text{ in DMSO})}{(RLU \text{ in absence of DNA}) - (RLU \text{ in DMSO})}.$$

A value of "−1" indicates higher than 50 μg/ml, therefore undetermined

FIGS. 2A and 2B presents representative structures of 14 particularly active compounds, including amentoflavone, apigenin, apigenin-7-O-glucoside, fitsetin, hinokiflavone, 6-hydroxy-apigenin, isorhamnetin, kaempferol, maclurin, morin, quercetagetin, quercetin dihydrate, 3,7,4'-trihydroxyflavone, fisetin, and theaflavin. Of these, hinokiflavone shows the lowest $IC_{50}$ (<1 μg/ml).

Example 13

Figure 8:
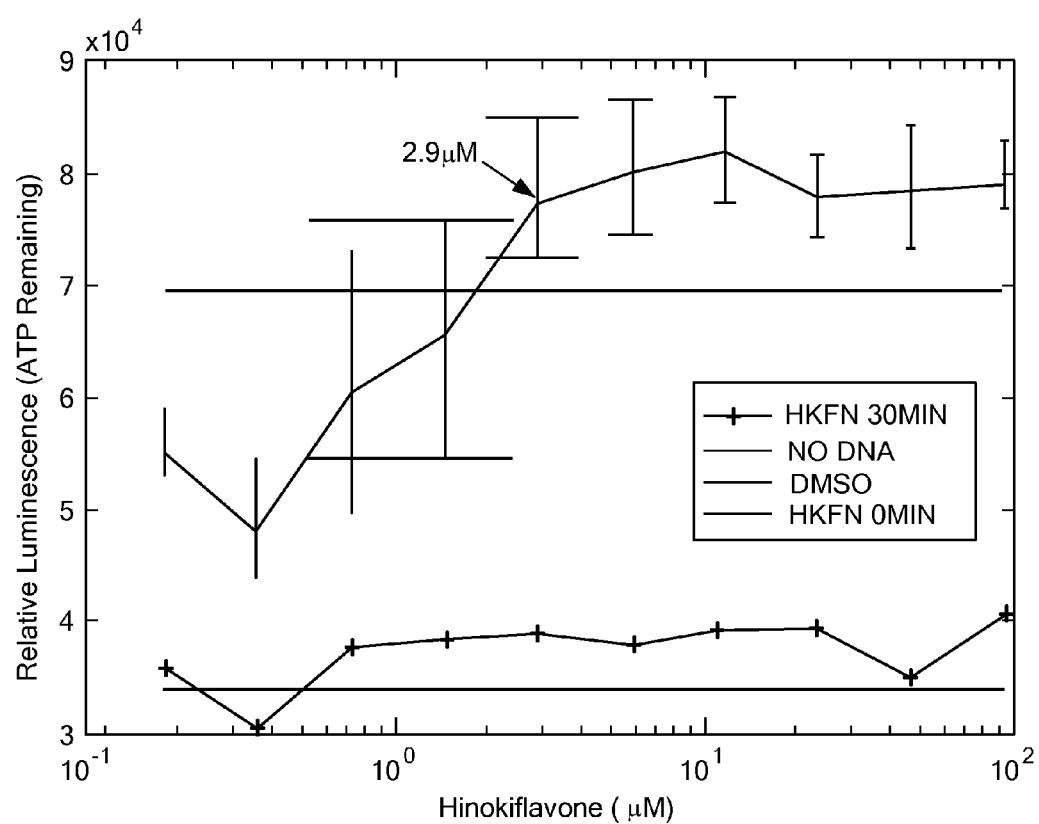
FIG. 8 is a graph showing inhibition of RecA ATPase activity by hinokiflavone.

Confirming RecA ATPase Inhibition Activity of Hinokiflavone Using In Vitro Luciferase Assay In order to confirm the result obtained in the screen, the present Applicants retested hinokiflavone in the luciferase assay described in Example 2. Hinokiflavone was added at time t=0 or at time t=30 minutes, and several different concentrations were tested. FIG. 8 shows that hinokiflavone completely inhibited RecA ATPase activity at a concentration of 2.9 μM.

Example 14

RecA Inhibitors in Survival Assay

Several RecA inhibitors that showed an ability to inhibit RecA ATPase activity in the luciferase assay of Example 2 were tested for their ability to potentiate ciprofloxacin antibiotic activity in a survival assay as described in Example 5. In particular, S. aureus strain S3 (ISP 794) was grown in the presence of 1 μg/ml ciprofloxacin and in the presence or absence of 50 μg/ml of each compound for 16 hours.

Figure 9:
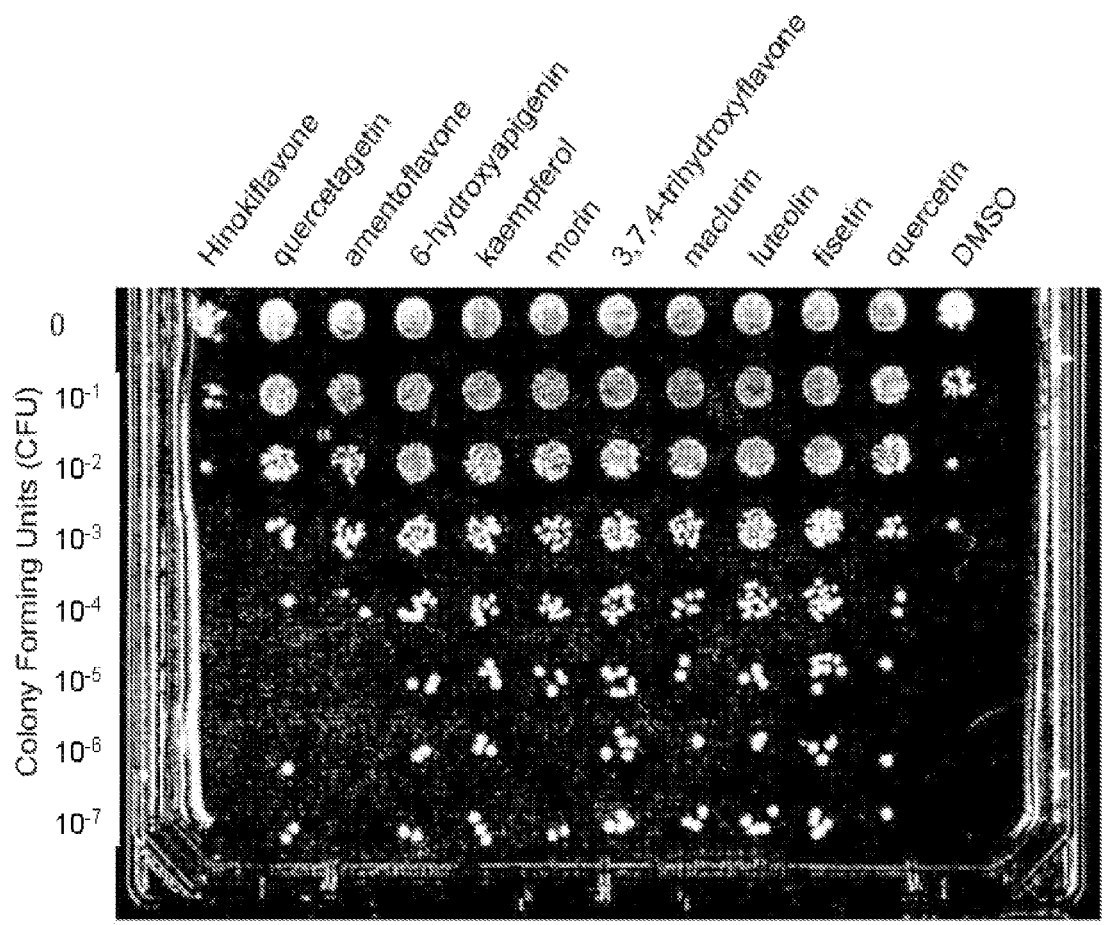
FIG. 9 is a photograph of a survival assay plate assessing the ability of various RecA inhibitors to potentiate ciprofloxacin.

FIG. 9 shows a survival assay plate of 11 different RecA inhibitors. As can be seen, only one of the compounds (hinokiflavone) potentiated ciprofloxacin activity. Indeed, each of the other compounds had a protective effect, allowing more cells to survive ciprofloxacin treatment than were able to do so in the absence of the RecA inhibitor. Without wishing to be bound by an particular theory, we note that such a protective effect might be expected, for example, if these compounds activate DNA repair, inhibit DNA gyrase, or generally have after effects in the cells.

Example 15

Hinokiflavone Activity in Survival Assay

S. aureus strain S3 was used in a survival assay as described in Example 5. The strain was grown in the presence of the following agents: DMSO alone; DMSO+1 μg/ml ciprofloxacin; DMSO+25 μg/ml hinokiflavone; or DMSO+1 μg/ml ciprofloxacin+25 μg/ml hinokiflavone.

Figure 10:
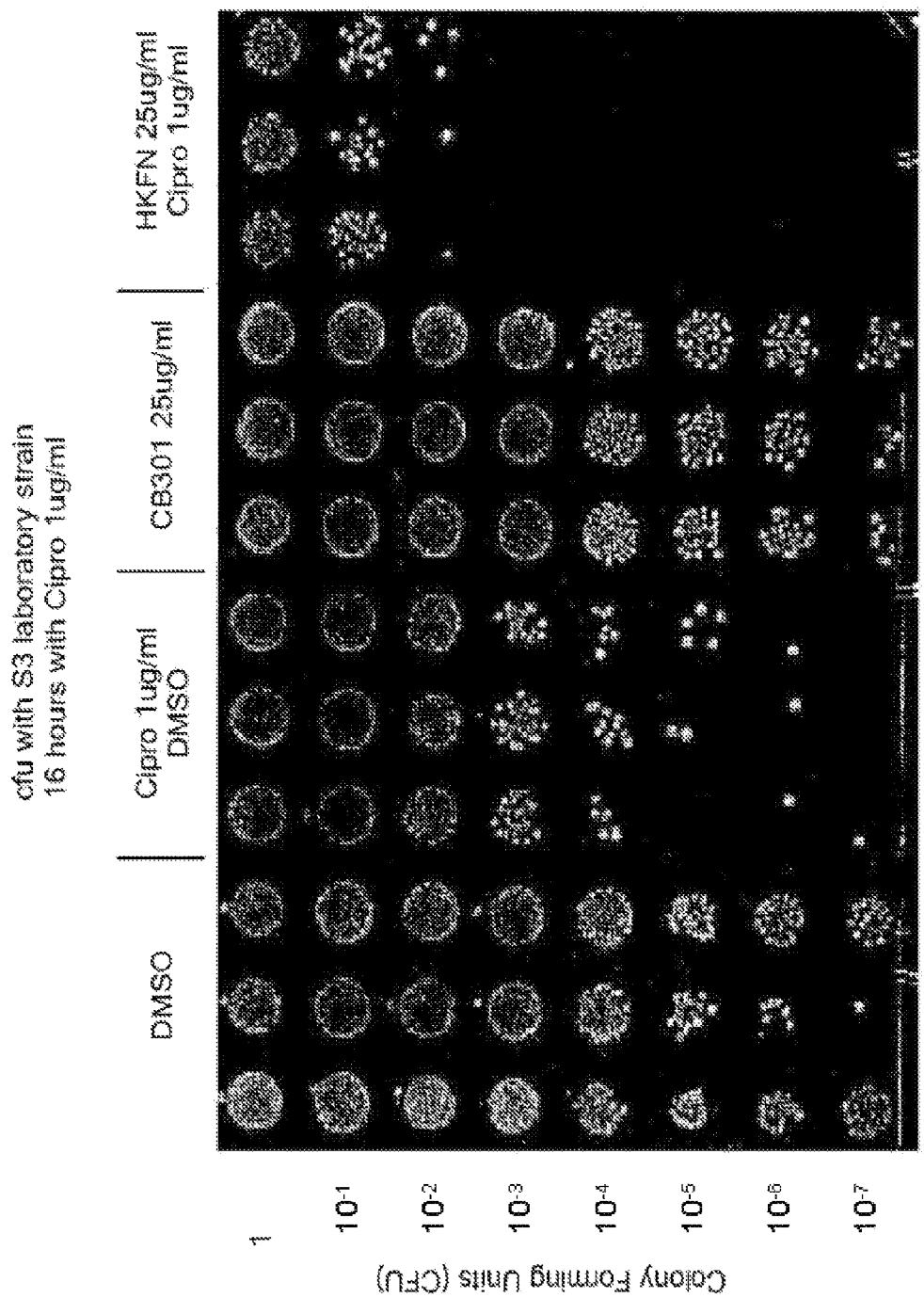
FIG. 10 is a photograph of a survival assay plate assessing the ability of hinokiflavone to kill cells, and to potentiate ciprofloxacin.

FIG. 10 shows a photo of the 16 hour growth time point. As can be seen, hinokiflavone strongly potentiates ciprofloxacin antibiotic activity. Indeed, approximately 100 fold (2 logs) fewer CFUs are observed in the presence of hinokiflavone as compared with in its absence. Although it is not immediately apparent from FIG. 10, several repeats of this experiment have also revealed modest antibiotic activity of hinokiflavone alone (i.e., in the absence of ciprofloxacin), particularly at high concentrations.

Similar results were achieved when the experiment was performed with a different S. aureus strain (S7) that is mildly resistant to ciprofloxacin. Specifically, hinokiflavone potentiated cirpofloxacin activity against this strain.

Hinokiflavone was not observed to have antibiotic activity, or an ability to potentiate ciprofloxacin when the experiment was performed with an E. coli strain rather than an S. aureus strain. Given that E. coli are gram negative whereas S. aureus are gram positive, it is possible that this different result represents differential ability of the compound to enter the cells (e.g., due to the stronger efflux pump and/or second lipid membrane found in gram negative cells), although in our hands, simple measures such as using a strain with a defective an efflux pump more permeable membranes were insufficient to reveal activity. Those of ordinary skill in the art appreciate that additional measures are commonly required to ensure effectiveness of antibiotic compounds in the treatment of gram negative infections as compared with gram positive infections.

Example 16

Hinokiflavone Activity in Growth Assay

The present Applicants have found that concentrations of hinokiflavone that potentiate the antibiotic activity of ciprofloxacin in a survival assay (i.e., that potentiate cell killing by ciprofloxacin) do not increase the MIC of ciprofloxacin in a growth assay.

Example 17

Figure 11:
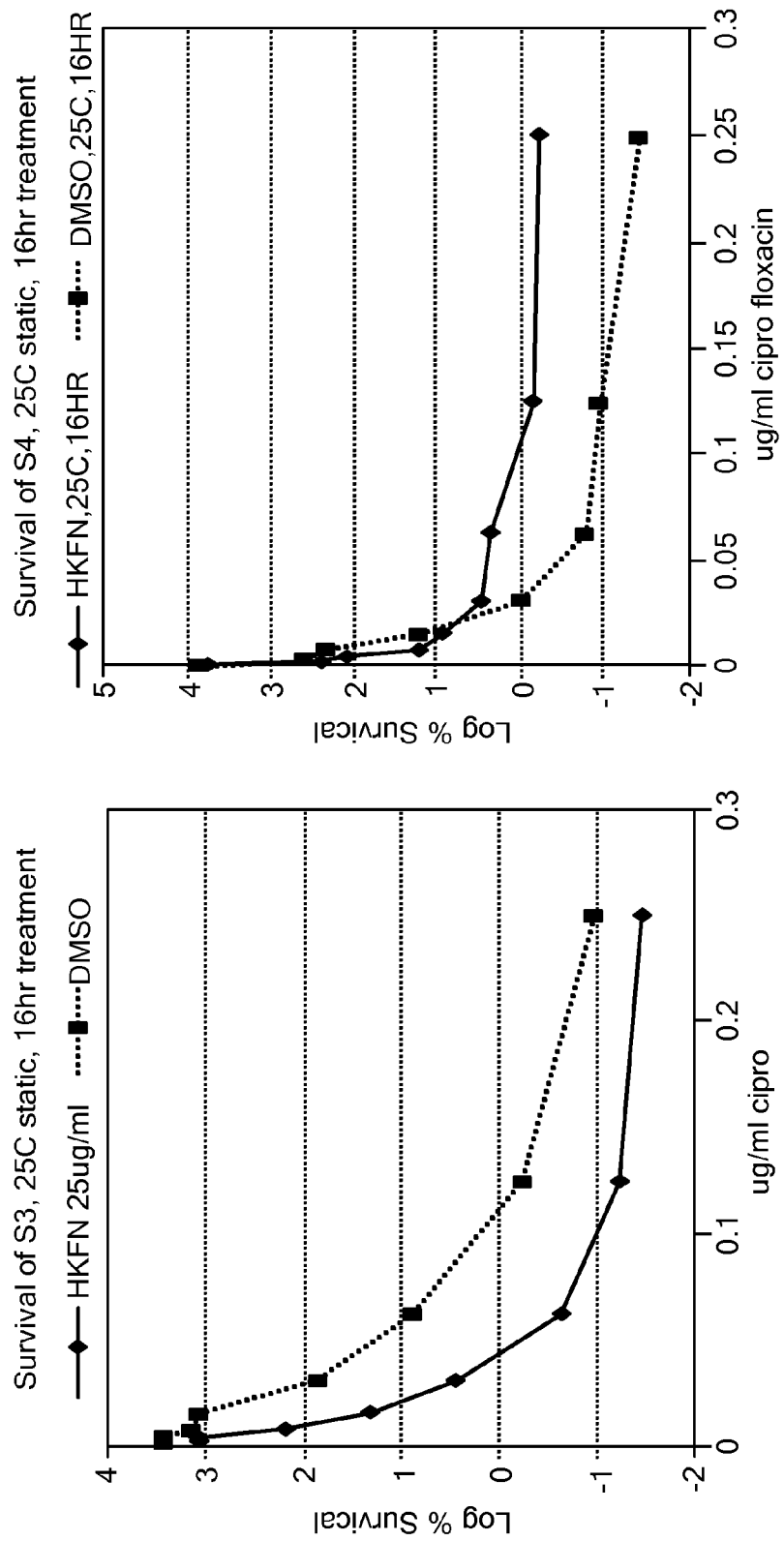
FIG. 11 is a graph comparing the ability of hinokiflavone to potentiate ciprofloxacin's activity in a survival assay against a RecA+ (S3) and recA− (S4) strain.
Figure 12:
FIG. 12 illustrates the method by which the docking site(s) of hinokiflavone on RecA were predicted, and also illustrates two potential sites.
Figure 13:
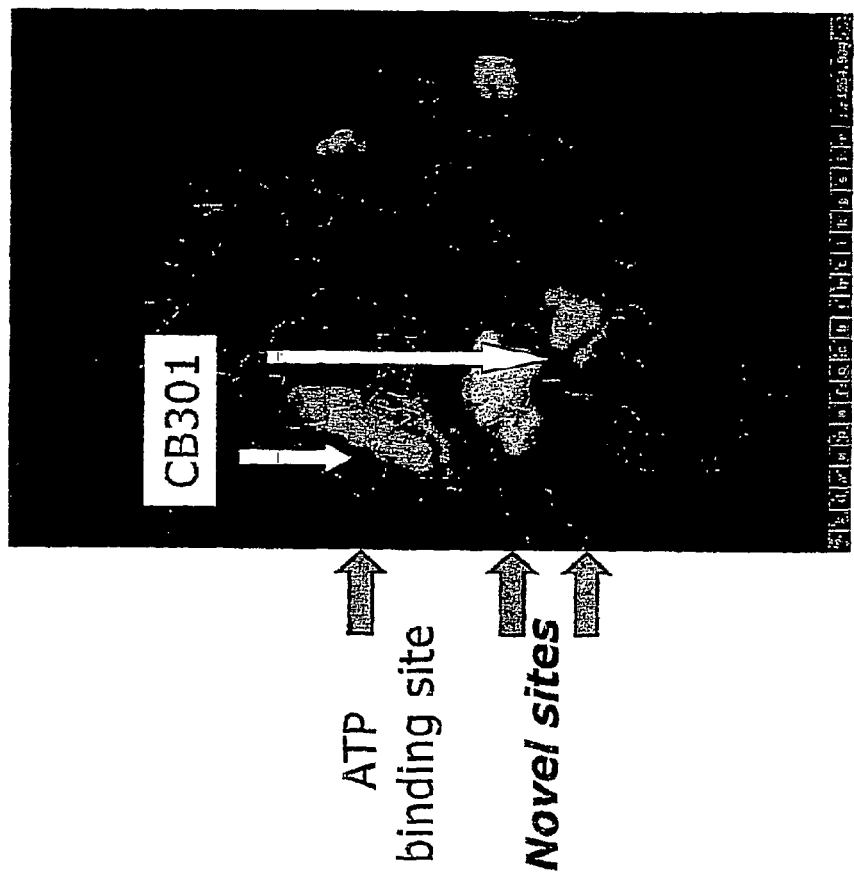
FIG. 13 is a close-up view illustrating the predicted potential hinokiflavone docking sites.
Figure 14:
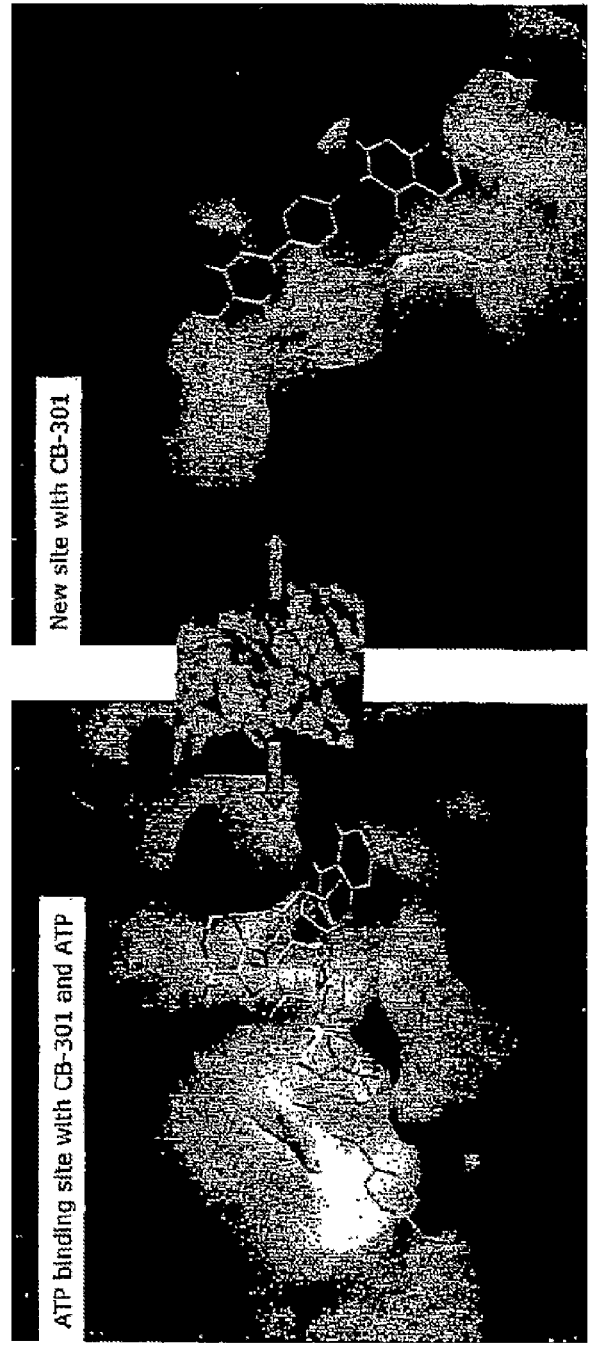
FIG. 14 summarizes the results of hinokiflavone docking study predictions.
Figure 15:
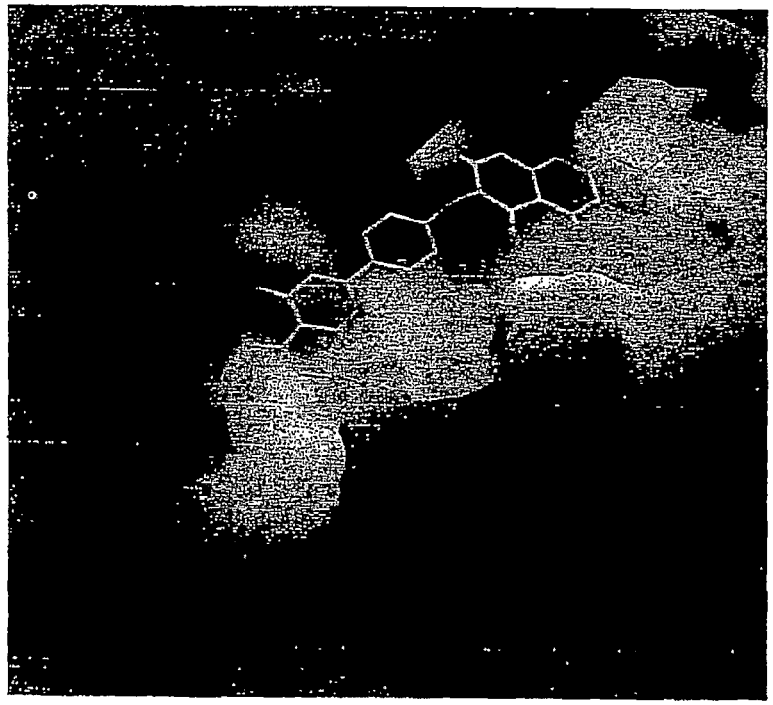
FIG. 15 highlights particular RecA residues involved in the hinokiflavone binding site.
Figure 16:
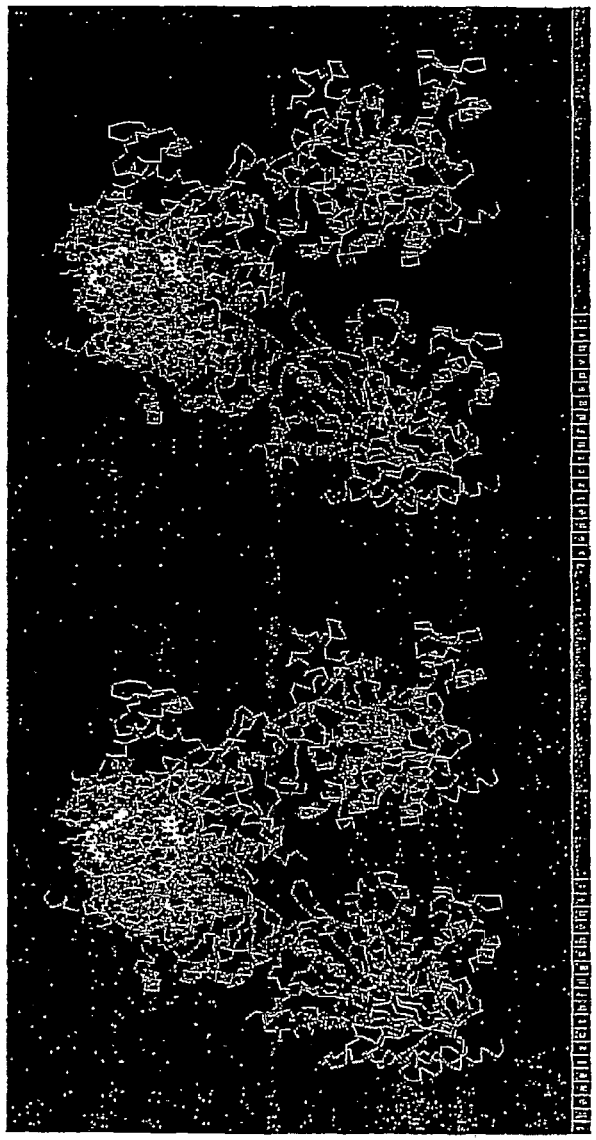
FIG. 16 illustrates the positioning of the hinokiflavone binding site in the context of a RecA filament.

Hinokiflavone Targets RecA; does not Potentiate Ciprofloxacin in the Absence of RecA S. aureus strains S3 (RecA+) and S4 (recA−) were used in a survival assay as described in Example 5. The strain was grown in the presence of the following agents: 1 µg/ml ciprofloxacin (in DMSO) or 1 µg/ml ciprofloxacin+25 µg/ml hinokiflavone (in DMSO). FIG. 11 is a graph showing that, in the absence of RecA (i.e., in the recA− strain S4), hinokiflavone does not potentiate the activity of ciprofloxacin. This finding confirms RecA as the target of hinokiflavone.

The data presented in FIG. 11, in fact, show a modest protective effect of hinokiflavone in the absence of RecA. That is, in the recA− strain S4, more cells survived in the presence of both ciprofloxacin and hinokiflavone than did in the presence of ciprofloxacin alone. One potential explanation for this finding is that the culture grown in the presence of both agents had fewer CFU at time point t=0 than did the culture grown in the presence of ciprofloxacin alone, although numbers were normalized for initial cell count. Alternatively or additionally, it is possible that the RecA+ and recA− strains have different growth rates. Thus, data points on the left hand sides of the graphs (e.g., up to about the 0.05 µg/ml ciprofloxacin data points) may well be more reliable than other data points.

Example 18

Stability of Hinokiflavone in Serum

The present Applicants have assessed the ability of hinokiflavone to potentiate ciprofloxacin's antibiotic activity in a survival assay in LB and in LB with 10% mouse serum, and found that hinokiflavone retained activity in the presence of mouse serum.

Example 19

Hinokiflavone Reduces the Incidence of Resistance to Ciprofloxacin

The present Applicants have found that the presence of hinokiflavone can reduce the ability of S. aureus cells to develop resistance to the fluoroquinolone antibiotic known as ciprofloxacin. Specifically, S. aureus cells were grown in the presence of 4×MIC of ciprofloxacin, and further in the presence or absence of hinokiflavone (25 µg/ml).

Aliquots were removed from the cultures every 24 hours, and were diluted such that the concentration of ciprofloxacin present in the culture was reduced to 0.5×MIC. These aliquoted samples were then assayed to determine whether they can grow in the presence of ciprofloxacin. Specifically, when growth is observed in the presence of ciprofloxacin at a concentration that is 4×MIC, then resistance is said to have developed. In the present experiment, the Applicants counted the number of wells in which growth was observed in the presence of ciprofloxacin at a concentration that is 4×MIC in order to assess the extent of resistance developed in our original culture. The following results were obtained:

| Number of Days Culture was Grown | Number of Wells in which Growth Observed in Presence of Ciprofloxacin at 4 × MIC | |
|---|---|---|
| | −Hinokiflavone | +Hinokiflavone |
| 0 | 0 | 0 |
| 1 | 1 | 0 |
| 5 | 2 | 0 |
| 6 | 2 | 0 |
| 7 | 3 | 3 |
| 10 | 11 | 4 |

These results demonstrate that the presence of hinokiflavone decreases the incidence of resistance to ciprofloxacin. Similar results would be expected to be obtained with other antibiotic agents, particularly with other quinolones and/or aminoglycosides.

Example 20

Defining a Binding Site for Hinokiflavone on RecA

The structure of RecA protein, in some cases bound to a substrate and/or to DNA, has been reported. For example, structures have been established for RecA from bacteria such as E. coli (Rossbach et al., BMC Struct. Biol., 2005, 20: 7; Story and Steitz, Nature, 1992, 355: 374; Story et al., Nature, 1992, 355: 37, Van Look et al., J. Mol. Biol., 2003, 333: 35; Xing and Bell, Biochemistry, 2004, 43: 1612; Yu and Edelman, Nat. Struct. Biol., 1997, 4: 101), Mycobacterium sp. (Datta et al., J. Bacteriol., 2003, 185: 4280; Datta et al., Nuc. Acid Res., 2000, 28: 4964), Proteus mirabilis (Weber and Steitz, J. Mol. Biol., 1986, 188: 109), and for RecA from Archea (Ariza et al., Nuc. Acids Res., 2005, 33: 165; Wu et al., Mol. Cell, 2004, 15: 423). The structure of the human RecA homolog, known as RAD51, has also been determined (Conway et al., Nat. Struc. Mol. Biol., 2004, 11: 791; Wu et al., J. Biol. Chem., 2005, 280: 722).

Binding interactions between particular compounds and a site or sites on a target molecule can be determined by molecular modeling programs that are known to those of ordinary skill in the art. These molecular modeling programs include, for example, QUANTA (Accelrys Inc., San Diego, Calif.) and the SYBYL suite of computational informatics software (Tripos Associates, Inc., St. Louis, Mo.).

Using the known crystal structure for E. coli RecA, the present Applicants have predicted binding sites for hinokiflavone and quercetin by using docking software to predict optimal interactions.

Figure 17:
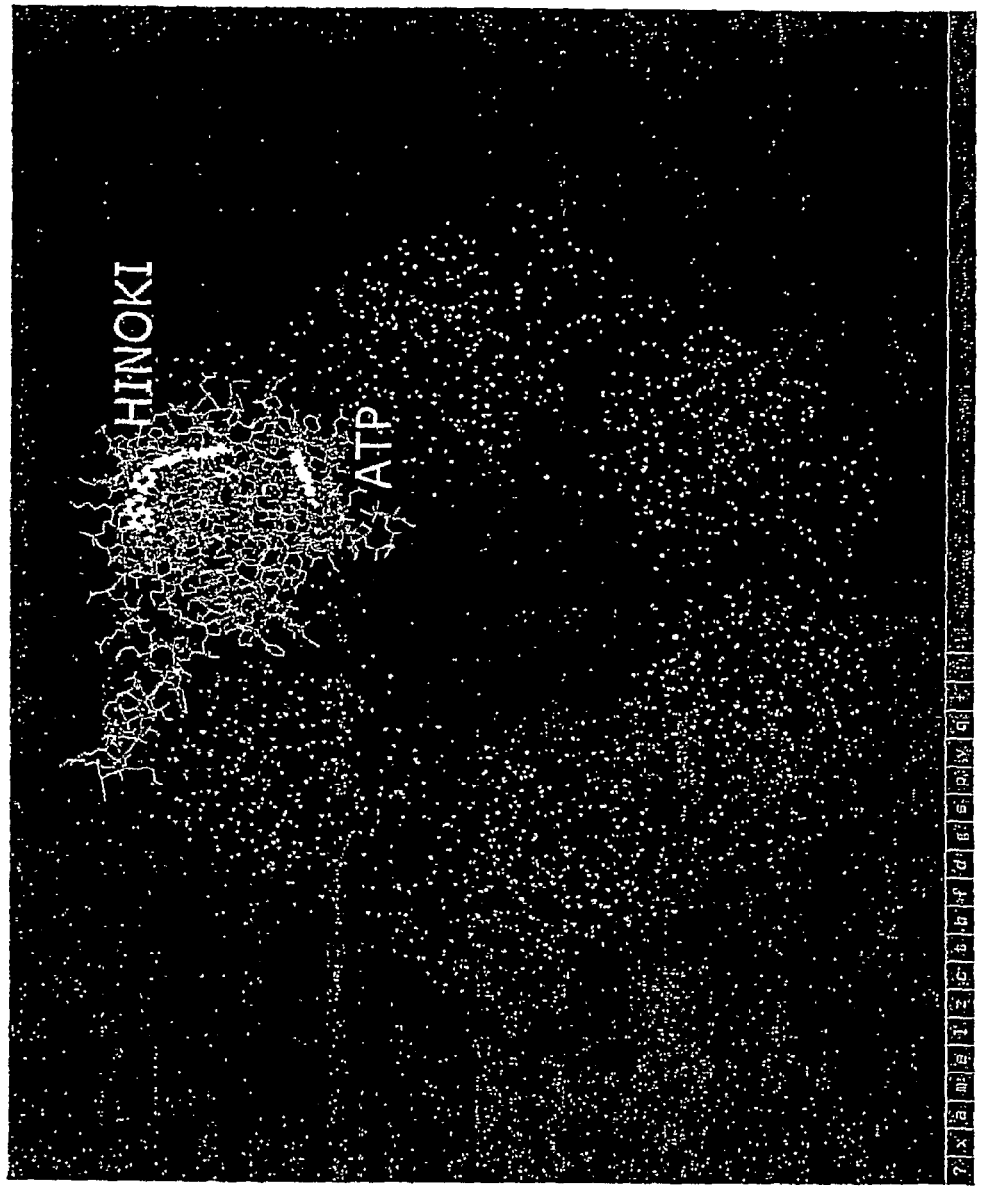
FIG. 17 represents a cross-section of a RecA filament, with the hinokiflavone binding site indicated.
Figure 18:
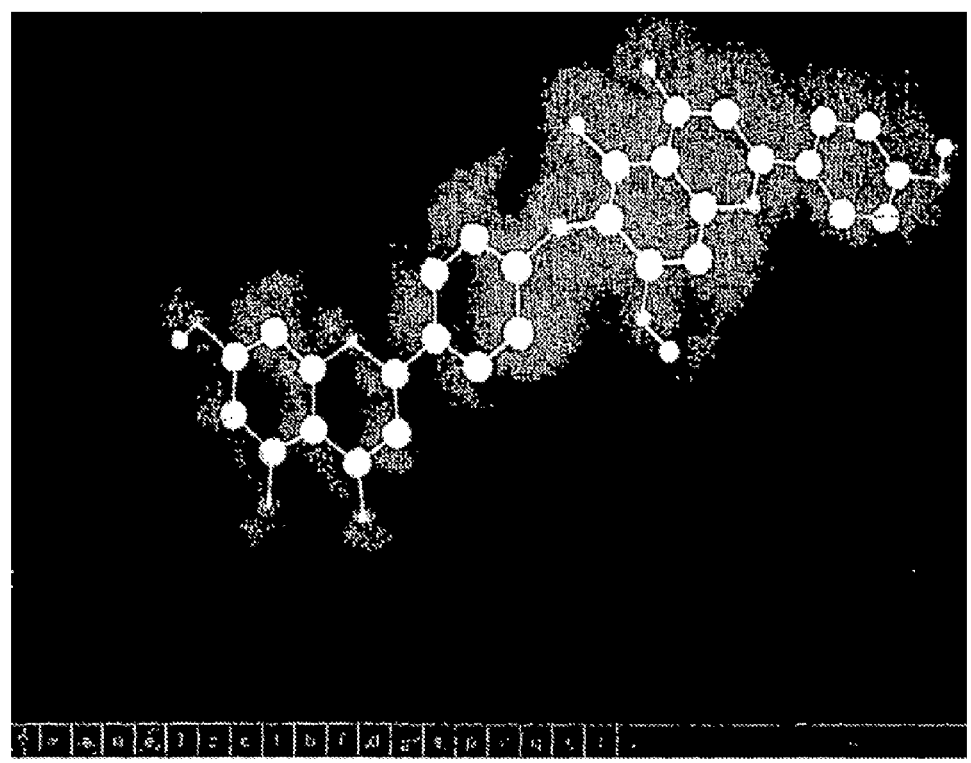
FIG. 18 illustrates attractive and repulsive interactions of hinokiflavone with its binding site.

This strategy correctly predicted the ATP binding site, as well as various other known functional sites and ion binding sites. Moreover, it defined two novel binding sites (see FIGS. 12-19), one of which involves R85, F270, Y271, K310, and R32. This site is situated on the outward surface of RecA (see FIGS. 17 and 18), and is found in all species investigated (see FIG. 19). In particular, the site is found in both gram positive and gram negative RecA proteins. Inhibitors binding such a site can act as broad-spectrum antibiotics, useful in the treatment of infections caused by both gram positive and gram negative organisms.

Work to prepare a co-crystal of RecA and hinokiflavone is in progress.

Example 21

Predicting Additional RecA Inhibitors

Having identified hinokiflavone as a particularly potent RecA inhibitor for use in accordance with the present invention, the present Applicants have assembled a collection of related compounds likely to share some or all of hinokiflavone's activities. For example, a variety of different flavones are known to inhibit helicases (see, for example, Xu et al., Nuc. Acids Res., 2001, 29: 5058). Bisflavones are of particular interest, given their structural relationship to hinokiflavone.

FIG. 3 presents a variety of exemplary potential RecA inhibitors according to the present invention that show significant structural similarity to hinokiflavone.

Figure 4A:
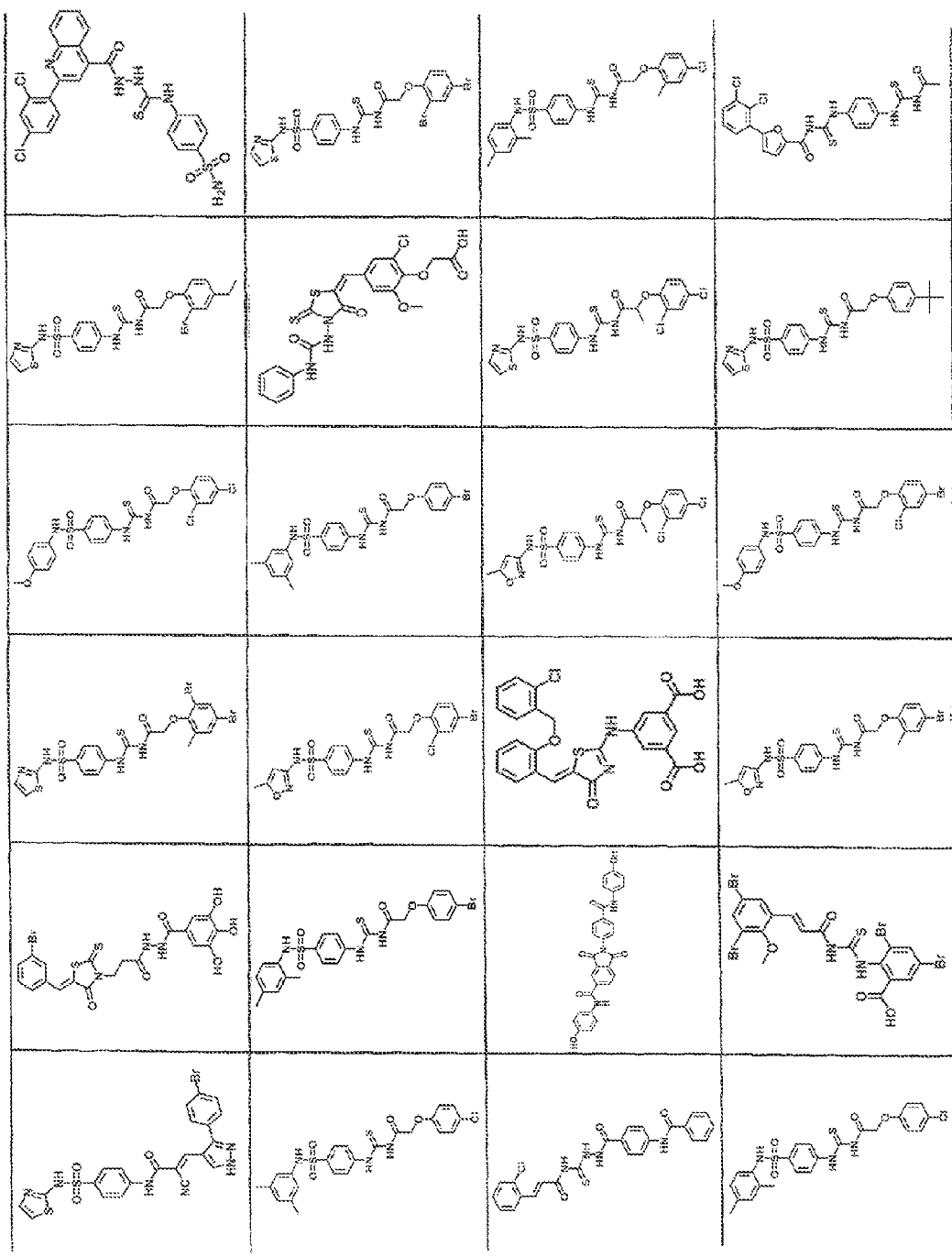
FIGS. 4A and 4B presents chemical structures of potential RecA inhibitors that are electronically related to hinokiflavone.
Figure 4B:
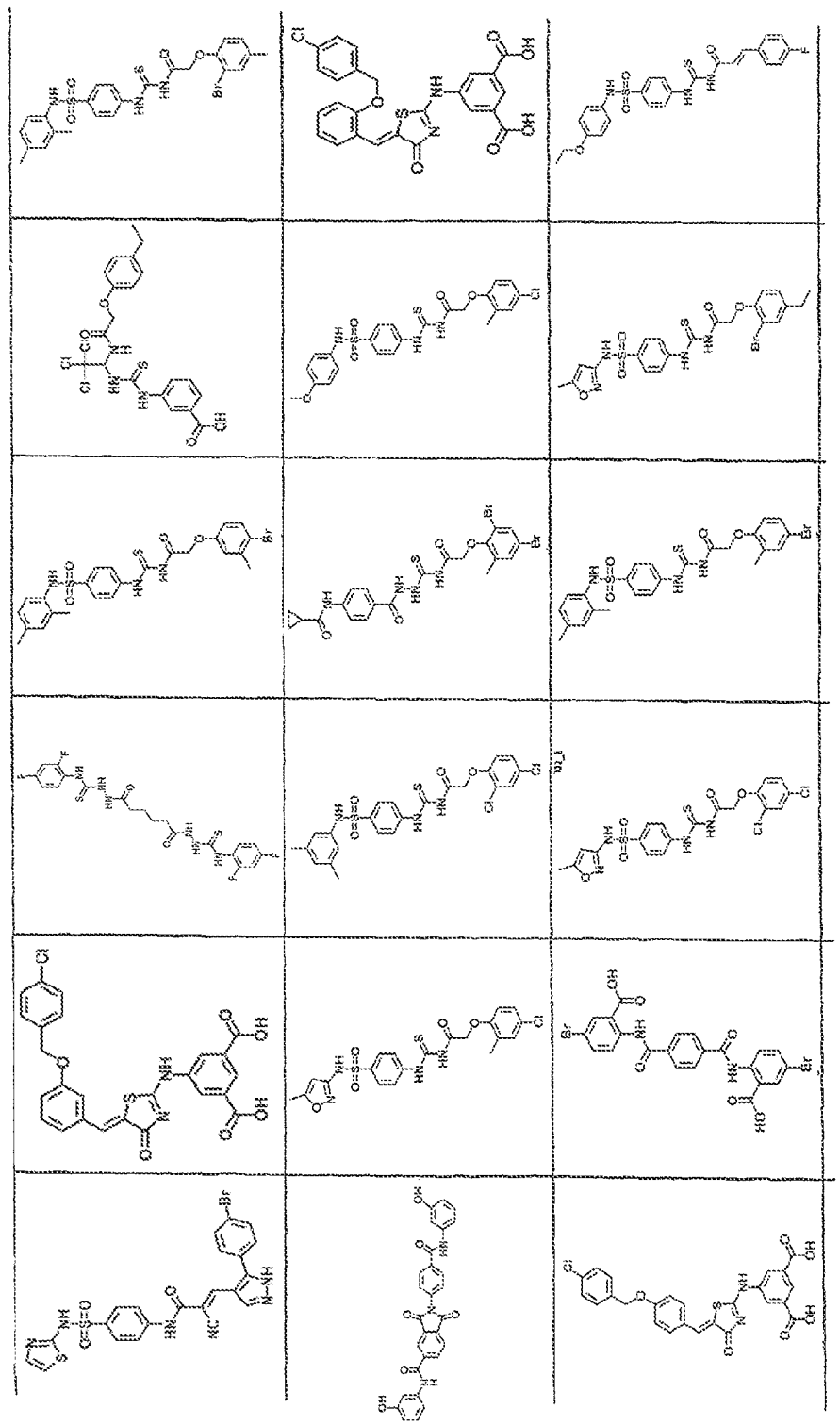

The present Applicants also considered the likelihood that compounds sharing electronic characteristics with hinokiflavone may well have similar ability to interact with RecA. FIGS. 4A and 4B present a variety of exemplary potential RecA inhibitors according to the present invention that show significant electronic similarity to hinokiflavone.

Example 22

Virulence of RecA

To further test the role of RecA in an animal environment, the present Applicants have studied the ability of *Staphylococcus aureus* strains—wild type and mutant recA—to propagate in mice. Strains MT5 (recA+) and BF12 (recA−) (as described by Fournier et al., Antimicrob. Agents Chemother., 2000, 44: 2160) were used. Both strains are mildly resistant to quinolones due to a mutation on the gyrase B subunit. CD-1 Female mice (Charles River, 20-22 g) were infected with *S. aureus* via intraperitoneal route in presence of mucin (5-8%). Mucin is known to boost infectivity of the pathogens. Inoculli of over $1 \times 10^7$ were shown to lead to close to 100% no survival using wild-type *S. aureus*.

|  | recA+ | | recA− | |
| --- | --- | --- | --- | --- |
|  | inoculum | survival | inoculum | survival |
| Experiment 1 | $8.8 \times 10^7$ | 1/10 | $1.23 \times 10^7$ | 10/10 |
| Experiment 2 | $5.5 \times 10^7$ | 0/5 | $2.12 \times 10^7$ | 5/5 |
| Total |  | 1/15 |  | 15/15 |

As shown in the previous table, all the animals infected with a recA− mutant survived the infection, while only one out of 15 survive in the case of animals infected the recA+ strain.

Another experiment was conducted using an abscess model (M. Tsuji et al., Antimicrob. Agents Chemother., 2003, 47: 2507-2512; J. S. Wright et al., Proc. Natl. Acad. Sci. USA, 2005, 102: 1691-1696). CD-1 female mice (18-20 g) was injected subcutaneously with 0.2 mL of bacteria mixed with Cytodex beads. 48 hours post injection, mice were euthanized, and the abscesses were aseptically removed, homogenized, diluted in PBS and plated onto LB solid agar plates. Colony Formation Units (CFUs) per gram of abscess were calculated. No CFUs were recovered from the mutant strain.

The table below provides a summary of the data obtained.

| Group | Inoculum CFU/mouse | Log CFU/g of abscess | Standard Deviation |
| --- | --- | --- | --- |
| recA+ | $2.35 \times 10^5$ | 6.19 | 0.55 |
|  | $2.35 \times 10^4$ | 3.75 | 0.36 |
| recA− | $6.5 \times 10^5$ | 0.00 | 0.00 |
|  | $6.5 \times 10^4$ | 0.00 | 0.00 |

This study revealed that there was full and complete clearance of the infective agent when recA is non-functional.

The fact that the cells lacking a functional recA have reduced virulence can be explained. First, phagocytes participate in immune defence by ingesting microbes and pathogens. Once ingested, pathogens are exposed to a number of lethal factors such as oxidative radicals, acidic pH and enzymes. Oxidative radicals cause DNA damage, thus recA− mutants are highly sensitive to the oxidative burst. Second, most bacterial infections are initiated by the adherence of pathogens to host tissues; this process requires the interaction of bacterial surface proteins called adhesins, with host "receptors" such as fibronectin. The RecA-LexA pathway was shown to mediate the quinolone induced fibronectin binding pathway in *S. aureus* (Bisognano et al., J. Biol. Chem., 2004, 279: 9064-9071), lack of expression of the fibronectin binding proteins likely results in the cell inability to adhere tissues in the animals.

From the results obtained by the present Applicants, which showed that *S. aureus* recA mutant is avirulent and is essential for viability in a mouse abscess infection model, it can be concluded that RecA is (1) a virulence factor, and (2) a stand alone target.

There were previous reports pointing to a virulence role of recA. Mei et al. (Mol. Microbiol., 1997, 26: 399-407) used transposon signature tagged mutagenesis in *S. aureus* to identify loci required for virulence in a murine model of bacteriemia. Out of the 1,248 mutants examined, 50 were found to have attenuated virulence; transposon insertion of the recA locus was one of them. Another study, which used *Salmonella typhirium* and *S. enterica* recombination defective mutants (recA among them), and a lethal dose 50 assay in mice, showed that the recA− strain is less virulent. The recA mutants were 3 to 4 log less virulent compared to the parent wild-type strain (N. A. Buchmeier et al., Mol. Microbiol., 1993, 7: 933-936; Cano et al., J. Bacteriol., 2002, 184: 592-595). The mutants were additionally tested for macrophages sensitivity. Results showed that these strains were more vulnerable to the oxidative burst generated by the phagocytes. A different study done using *Brucella abortus* showed that the recA mutant has reduced survival in mice (F. M. Tatum et al., Microb. Pathog., 1993, 14: 177-185). Recombinational repair was shown to be critical for bacterial cells exposed to nitric oxide (E. J. Spek et al., J. Bacteriol., 2001, 183: 131-138); nitric oxide is connected to macrophage-mediated immunity.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A pharmaceutical composition comprising a RecA inhibitor, and at least one physiologically acceptable carrier or excipient, wherein the composition further comprises at least one antibiotic and wherein the RecA inhibitor interacts directly with the RecA protein and wherein the RecA inhibitor is selected from the group consisting of: amentoflavone, hinokiflavone, isorhamnetin, maclurin, quercetagetin, quercetin dehydrate, 3,7,4'-trihydroxyflavone, theaflavin or a compound of formula (I) or formula (II) or pharmaceutical acceptable salts thereof or combinations thereof, wherein the compound of formula (I) has the following structure:

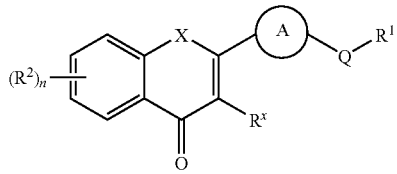
I wherein:

X is oxygen, sulfur, or N(R);

n is 0 to 4;

$R^1$ is hydrogen, or an optionally substituted group selected from a $C_{1-6}$ aliphatic group, a monocyclic 3-8 membered saturated, partially unsaturated, or aryl ring having 0-4 heteroatoms independently selected from nitrogen, oxygen, or sulfur, or a bicyclic 8-10 membered saturated, partially unsaturated, or aryl ring having 0-5 heteroatoms independently selected from nitrogen, oxygen, or sulfur;

each $R^2$ is independently halogen, $R^3$, $OR^3$, $SR^3$, $N(R^3)_2$, $C(O)R^3$, $C(O)OR^3$, $NR^3C(O)R^3$, $C(O)NR^3$, $SO_2R^3$ $NR^3SO_2R^3$ $SO_2N(R^3)_2$;

each $R^3$ is independently hydrogen or an optionally substituted group selected from a $C_{1-6}$ aliphatic group, a monocyclic 3-8 membered saturated, partially unsaturated, or aryl ring having 0-4 heteroatoms independently selected from nitrogen, oxygen, or sulfur, or a bicyclic 8-10 membered saturated, partially unsaturated, or aryl ring having 0-5 heteroatoms independently selected from nitrogen, oxygen, or sulfur;

Q is a valence bond or a bivalent, saturated or unsaturated, straight or branched $C_{1-6}$ hydrocarbon chain, wherein 0-2 methylene units of Q are independently replaced by —O—, —NR—, —S—, —OC(O)—, —C(O)O—, —C(O)—, —SO—, —SO$_2$—, —NRSO$_2$—, —SO$_2$NR—, —NRC(O)—, —C(O)NR—, —OC(O)NR—, or —NRC(O)O—;

each R is independently hydrogen or an optionally substituted aliphatic group;

$R^x$ is R or OR; and

Ring A is an optionally substituted 3-8 membered bivalent, saturated, partially unsaturated, or aryl monocyclic ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; and wherein the compound of formula (II) has the following structure:

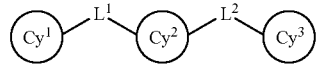
II wherein:

$Cy^1$ is a an optionally substituted 5-6 membered aryl ring having 0-3 heteroatoms independently selected from nitrogen, oxygen, or sulfur;

$L^1$ is a valence bond, a $C_{1-6}$ bivalent saturated, unsaturated, straight or branched hydrocarbon chain, —N(R)—, —N(R)SO$_2$—, —N(R)SO$_2$N(R)—, —N(R)C(O)—, —C(O)N(R)—, or —N(R)C(O)N(R)—;

each R is independently hydrogen or an optionally substituted $C_{1-6}$ aliphatic group;

$Cy^2$ is an optionally substituted 6-membered aryl ring having 0-2 nitrogen atoms, an 8-10 membered bicyclic heteroaryl ring having 1-3 heteroatoms independently selected from nitrogen, oxygen, or sulfur, or an optionally substituted 5-membered heteroaryl ring having 1-2 heteroatoms independently selected from nitrogen, oxygen, or sulfur;

$L^2$ is a $C_{1-6}$ bivalent saturated, unsaturated, straight or branched hydrocarbon chain, —CH$_2$CH$_2$C(=W)N(R) N(R)C(=W)—, —N(R)C(=W)N(R)C(=W)C(R)$_2$ W—, —C(=W)N(R)N(R)C(=W)N(R)—, —C(=W) N(R)N(R)C(=W)N(R)CH=CH$_2$, or —C(=W)N(R)C (=W)N(R)—, wherein each W is independently oxygen or sulfur; and $Cy^3$ is an optionally substituted 6-membered aryl ring having 0-2 nitrogen atoms.

2. The pharmaceutical composition of claim 1, wherein the antibiotic is a member of the group consisting of aminoglycosides, aminomethylcyclines, aminophenicols, ansamycins, β-lactams, carbapenems, dapsones, 2,4-diaminopyrimidines, glycopeptides, glycycyclines, ketolids, lincomycins, lincosamides, macrolides, nitrofurans, oxazolidinones, peptides, polymyxins, quinolones, rifabutins, streptogramins, sulfonamides, sulfones, tetracyclines, and combinations thereof.

3. The pharmaceutical composition of claim 1, wherein the RecA inhibitor binds to at least one binding site on the RecA protein.

4. The pharmaceutical composition of claim 1, wherein the RecA inhibitor competes with hinokiflavone for binding to the RecA protein.

5. The pharmaceutical composition of claim 1, wherein the RecA inhibitor binds to more than one binding site on the RecA protein.

6. The pharmaceutical composition of claim 1, wherein the RecA inhibitor inhibits at least one activity of RecA, wherein the RecA activity is a member of the group consisting of DNA binding, monomer interaction, helicase activity, filament formation, ATP binding, ATP hydrolysis, co-protease activity, recombinase activity, and replication function.

7. The pharmaceutical composition of claim 1, wherein the RecA inhibitor inhibits ATPase activity.

8. The pharmaceutical composition of claim 1, wherein the RecA inhibitor has a IC50 of less than about 100 μg/mL, less than about 50 μg/mL, less than about 15 μg/mL, less than about 10 μg/mL, less than about 5 μg/mL, less than about 3 μg/mL, or less than about 1 μg/mL.

9. The pharmaceutical composition of claim 1, wherein X is oxygen.

10. The pharmaceutical composition of claim 1, wherein $R^1$ has the following structure:

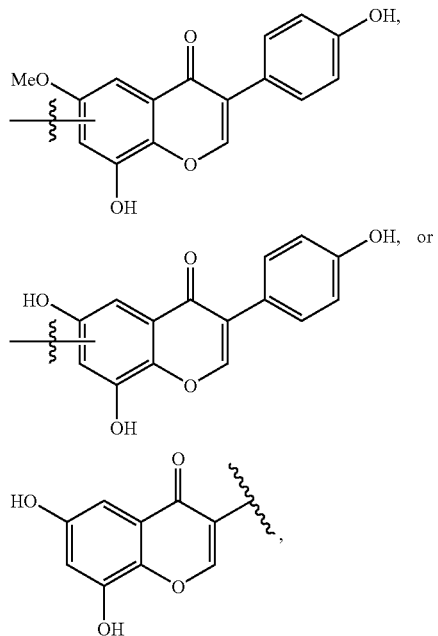

wherein each wavy line depicts the point of attachment to Q.

11. The pharmaceutical composition of claim 1, wherein $R^1$ has the following structure:

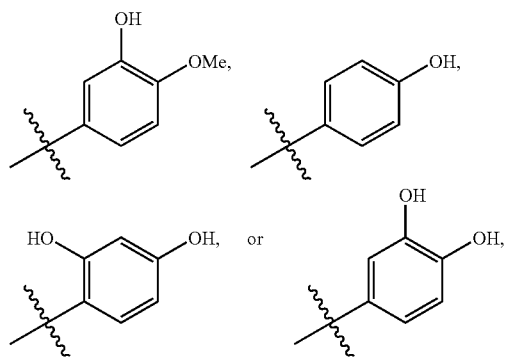

wherein each wavy line indicates the point of attachment to Q.

12. The pharmaceutical composition of claim 1, wherein $R^2$ is selected from the group consisting of: OH, OMe,

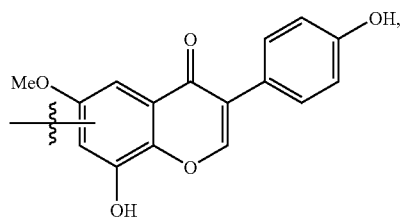

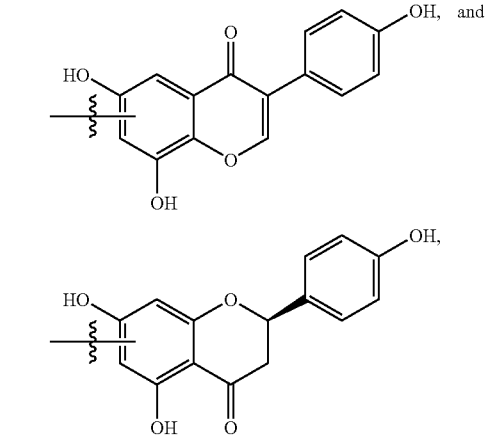

wherein each wavy line depicts the point of attachment.

13. The pharmaceutical composition of claim 1, wherein the RecA inhibitor has any one of the following structures:

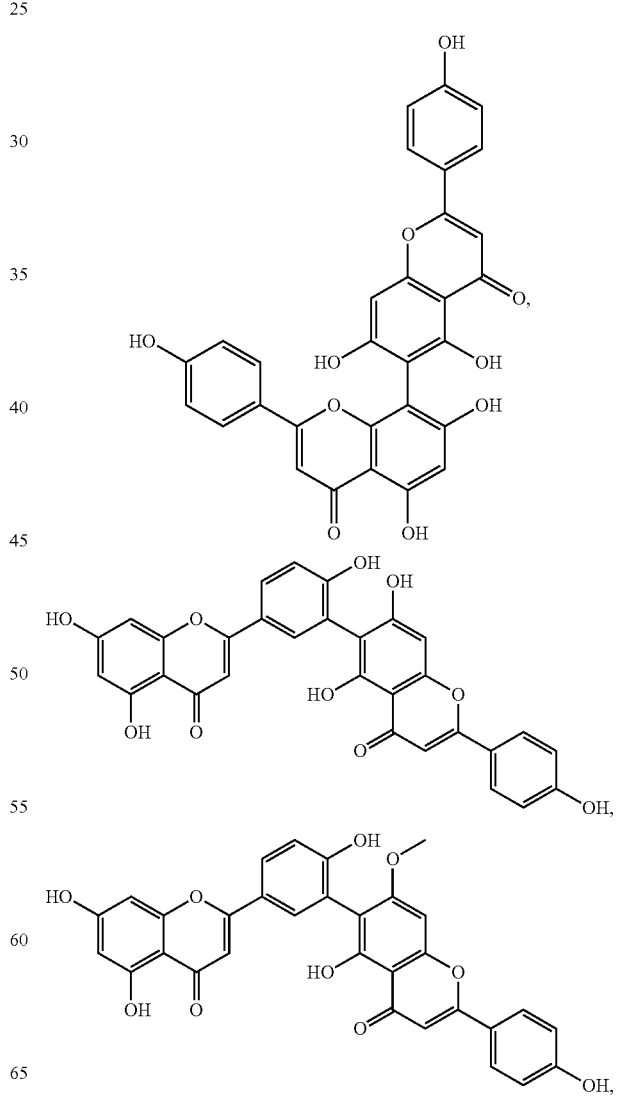

47
-continued
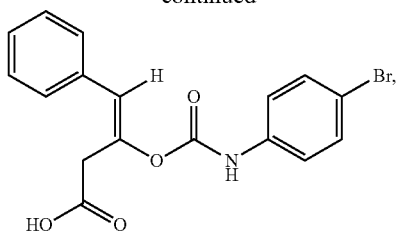
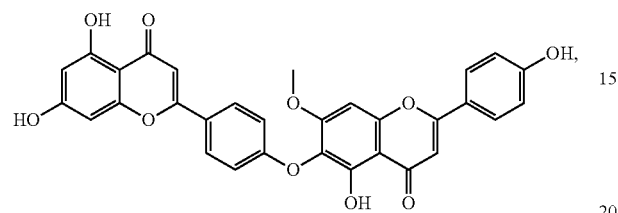
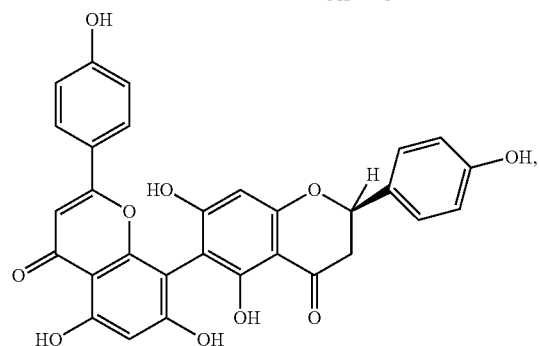
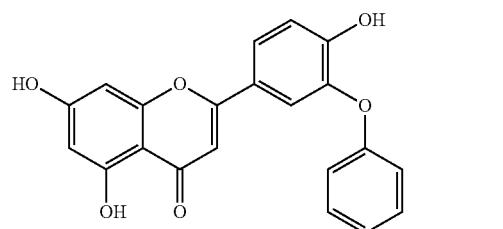
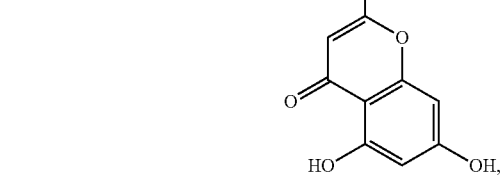
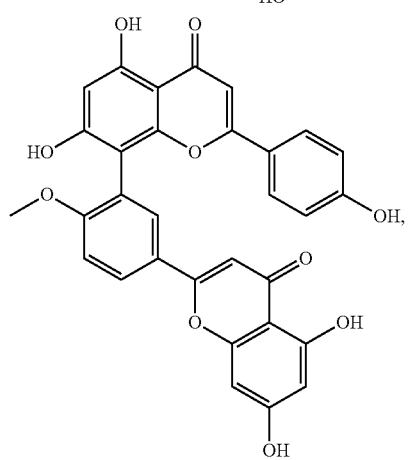
48
-continued
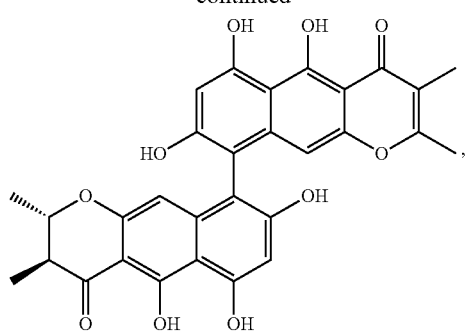
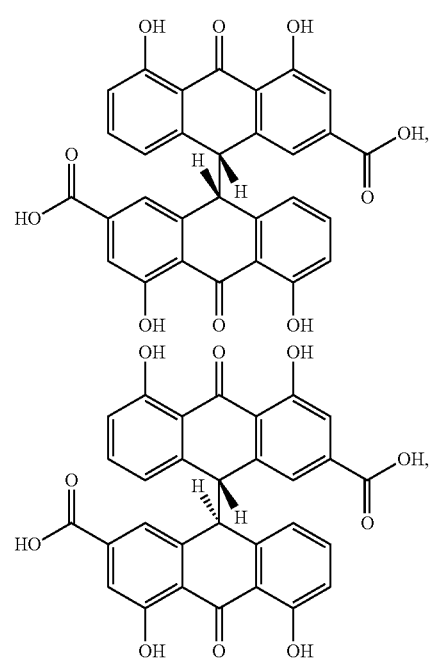
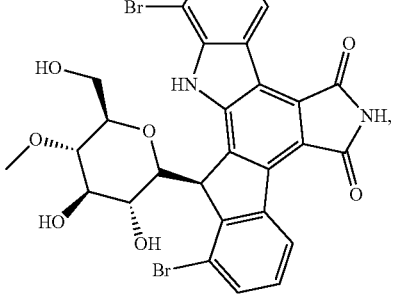
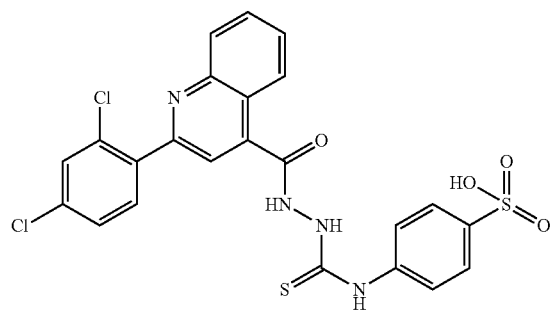

49
-continued
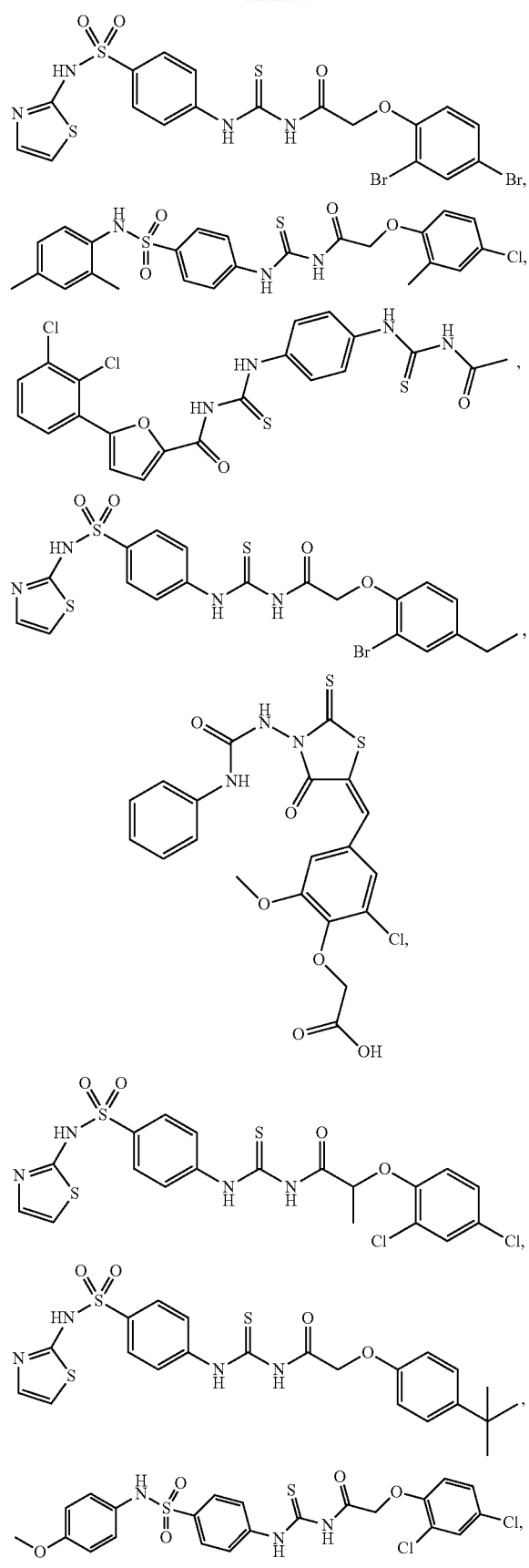
50
-continued
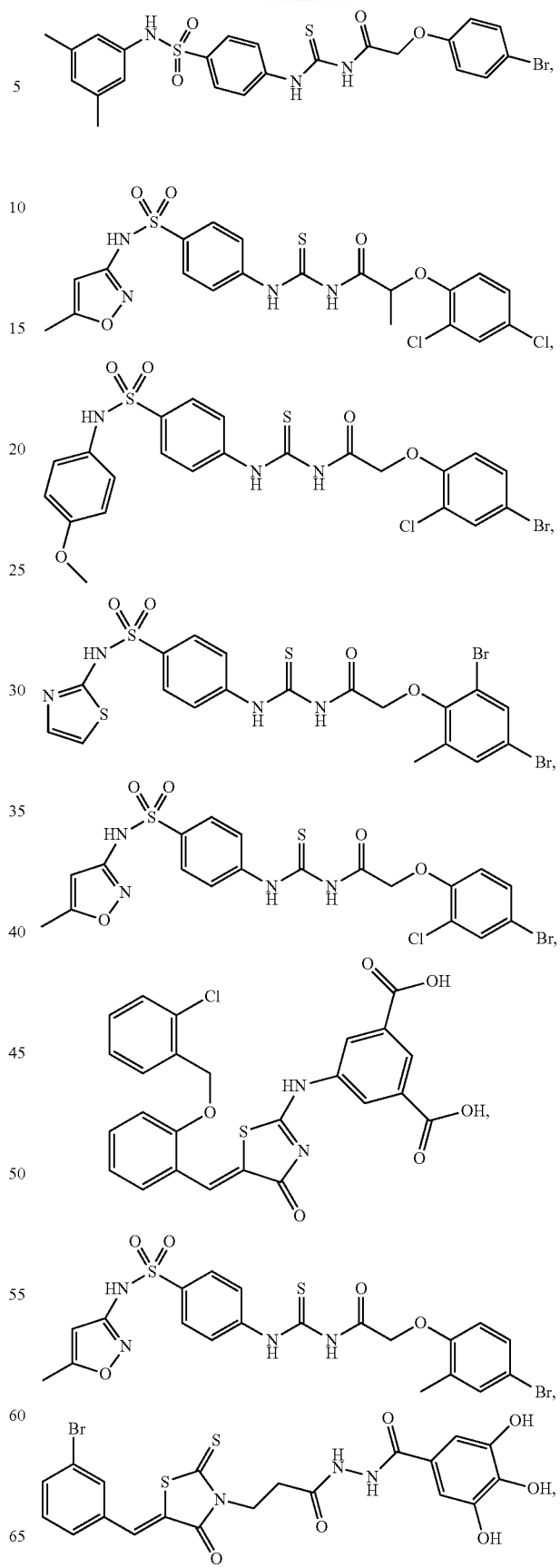

51
-continued
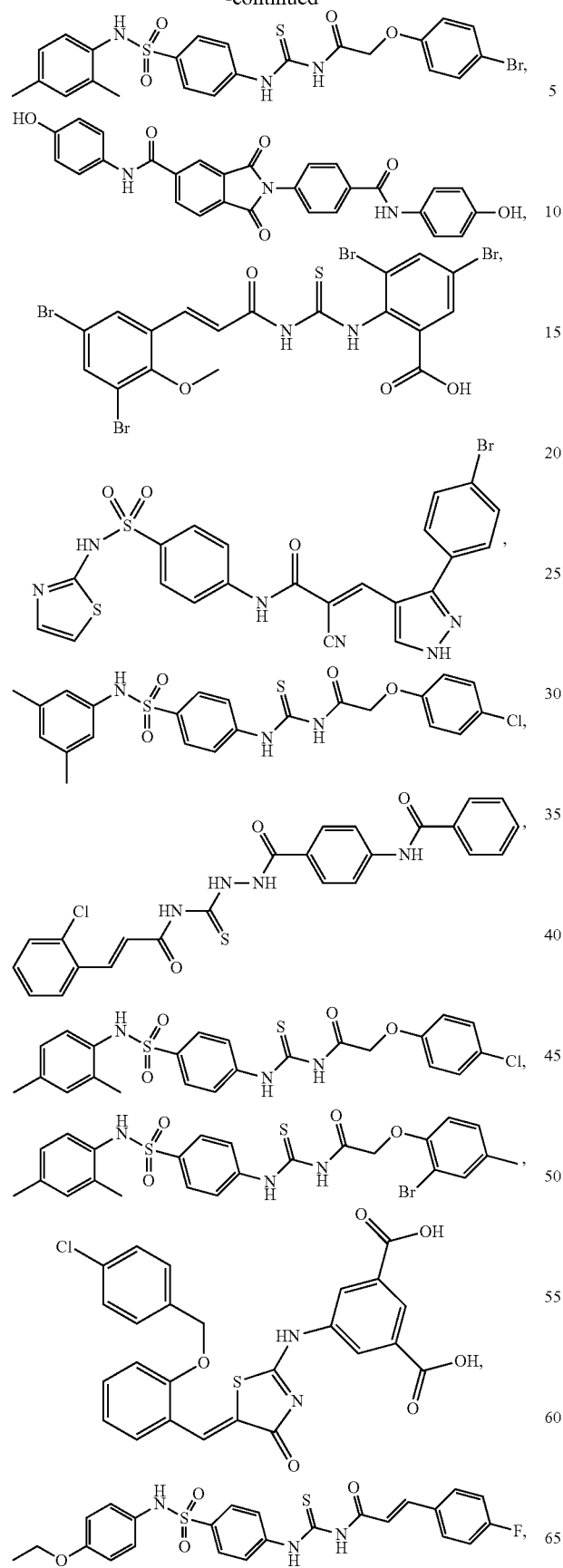
52
-continued
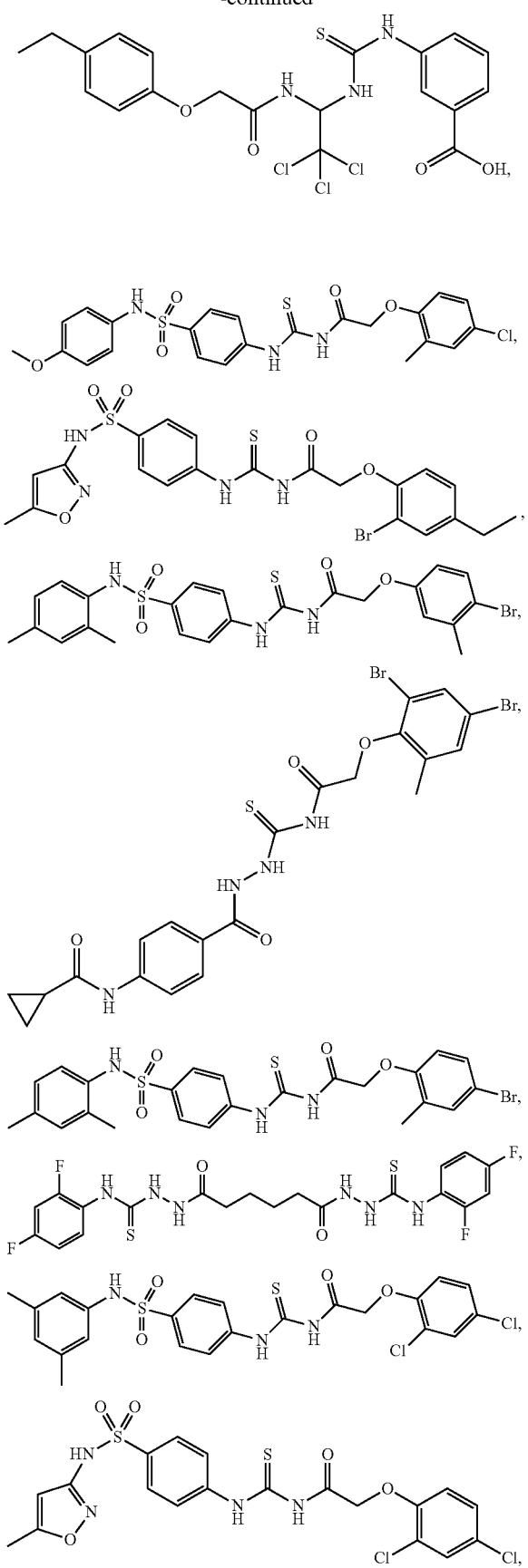

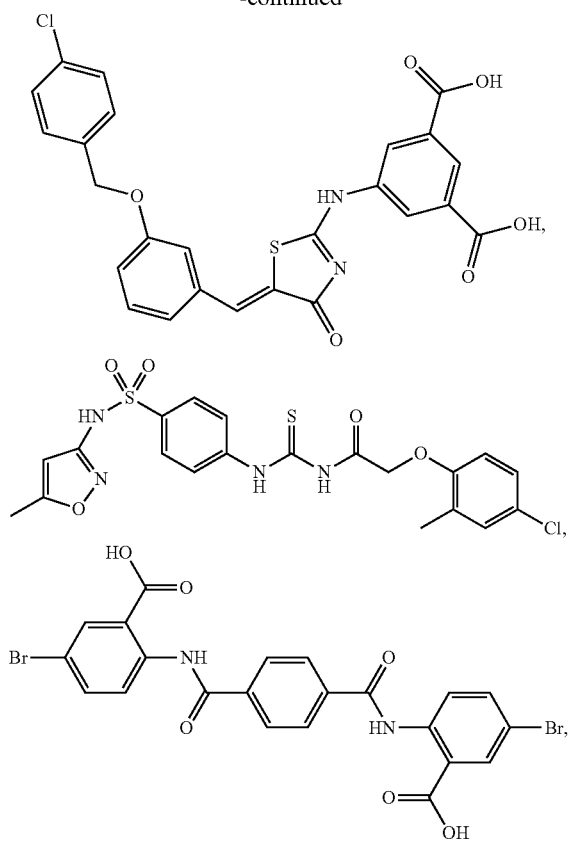
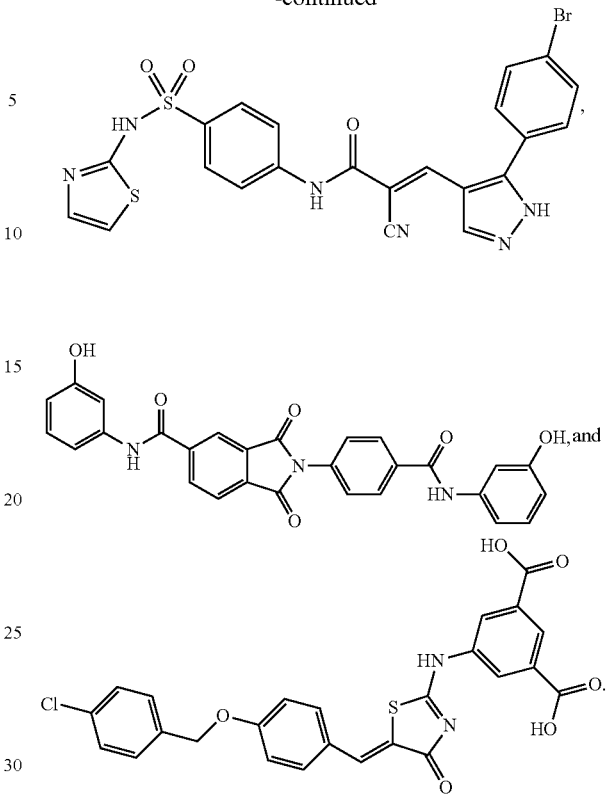
* * * * *